US006750194B1

(12) United States Patent
Isfort et al.

(10) Patent No.: US 6,750,194 B1
(45) Date of Patent: Jun. 15, 2004

(54) METHODS OF IDENTIFYING COMPOUNDS FOR REGULATING MUSCLE MASS OR FUNCTION USING VASOACTIVE INTESTINAL PEPTIDE RECEPTORS

(75) Inventors: Robert Joseph Isfort, Fairfield, OH (US); Russell James Sheldon, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/694,519

(22) Filed: Oct. 23, 2000

(51) Int. Cl.$^7$ .................. A01N 61/00; A61K 31/00; G01N 33/53
(52) U.S. Cl. ........................... 514/1; 435/7.1
(58) Field of Search .................. 514/1; 435/7.1; 431/7.1

(56) References Cited

U.S. PATENT DOCUMENTS

| 4,835,252 | A | * | 5/1989 | Musso et al. | ............... 530/324 |
| 5,882,899 | A | | 3/1999 | Mojsov et al. | ............... 435/7.1 |
| 6,114,127 | A | | 9/2000 | Bergsma et al. | |

FOREIGN PATENT DOCUMENTS

| WO | WO 95/06724 | 3/1995 |
| WO | WO 96/37223 | 11/1996 |
| WO | WO 98/02453 | * 1/1998 |

OTHER PUBLICATIONS

Said, S.I., "Vasoactive Intestinal Peptide", J. Endocrinol. Invest. 1986, vol. 9, pp. 191–200.*
Laburthe M. et al., "Molecular Analysis of Vasoactive Intestinal Peptide Receptors", Ann. NY Acad. Sci. 1988, vol. 527, pp. 296–313.*
Emami S. et al., "Functional Receptors for VIP, GIP, Glucagon–29 and –37 in the HGT–1 Human Gastric Cancer Cell Line", Peptides 1986, vol. 7, pp. 121–127.*
Laburthe M. et al., "Interaction of PHM, PHI, and 24–Glutamine PHI with Human VIP Receptors from Colonic Epithelium: Comparison with Rat Intestinal Receptors", Life Sci. 1985, vol. 36, pp. 991–995.*
Vittone et al., "Effects of Single Nightly Injections of Growth Hormone–Releasing Hormone (GHRH 1–29) in Healthy Elderly Men", Metabolism 1997, vol. 46, pp. 89–96.*
Ulrich C.D. et al., "Secretin and Vasoactive Intestinal Peptide Receptors: Members of a Unique Family of G Protein–Coupled Receptors", Gastroenterology 1998, vol. 114, pp. 382–397.*
Gozes, I., et al., "Pharmaceutical VIP: Prospects and Problems", Current Medical Chemistry, vol. 6, pp. 1019–1034, (1999).
Maltin, C.A., et al., "Clenbuterol, a β–adrenoceptor agonist, increases relative muscle strength in orthopaedic patients", Clinical Science, vol. 84, pp. 651–654, (1993).
Signorile, J.F., et al., "Increased Muscle Strength in Paralyzed Patients after Spinal Cord Injury: Effect of Beta–2 Adrenergic Agonist", Arch Phys Med Rehabil, vol. 76, pp. 55–58, (1995).
Martineau, L., et al., "Salbutamol, a $β_2$–adrenoceptor agonist, increases skeletal muscle strength in young men", Clinical Science, vol. 83, pp. 615–621, (1992).
Gourlet, P. et al., "The Long–Acting Vasoactive Intestinal Polypeptide Agonist RO 25–1553 Is Highly Selective of the $VIP_2$ Receptor Subclass", Peptides, 1996, vol. 18, pp. 403–408.
Wei, Y. et al., "Tissue Specific Expression of Different Human Receptor Types for Pituitary Adenylate Cyclase Activating Polypeptide and Vasoactive Intestinal Polypeptide: Implications for their Role in Human Physiology", J. of Neuroendocrinology, 1996, vol. 8, pp. 811–817.
Adamou, J.E. et al., "Cloning and functional Characterization of the Human Vasoactive Intestinal Peptide (VIP)–2 Receptor", Biochemical and Biophysical Research Communications, 1995, vol. 209, No. 2, pp. 385–392.
Gourlet, P. et al., "Development of High Affinity Selective $VIP_1$ Receptor Agonists", Peptides, 1997, vol. 18, No. 10, pp. 1539–1545.
Iguchi, G. et al., "Cloning and characterization of the 5'–Flanking Region of the Human Growth Hormone–releasing Hormone Receptor Gene", J. of Biological Chem., 1999, vol. 274, No. 17, pp. 12108–12114.

* cited by examiner

Primary Examiner—Jeffrey Fredman
Assistant Examiner—Teresa Strzelecka
(74) Attorney, Agent, or Firm—Naishadh N. Desai; Mary Pat McMahon; Cynthia M. Bott

(57) ABSTRACT

Screening methods for identifying compounds that regulate skeletal muscle atrophy or hypertrophy, regulate the activity or expression of the vasoactive intestinal peptide receptors (VPAC) or regulate expression of vasoactive intestinal peptide (VIP) or VIP analogs are provided. Methods for the prophylactic or therapeutic treatment of skeletal muscle atrophy utilizing VPAC as the target for intervention are described.

3 Claims, 10 Drawing Sheets

METHODS OF IDENTIFYING COMPOUNDS FOR REGULATING MUSCLE MASS OR FUNCTION USING VASOACTIVE INTESTINAL PEPTIDE RECEPTORS

TECHNICAL FIELD

The present invention relates to methods of identifying candidate compounds for regulating skeletal muscle mass or function, regulating the activity or expression of a vasoactive intestinal peptide receptors (VPAC) or regulating expression of vasoactive intestinal peptide (VIP) or VIP analogs. The invention also relates to methods for the treatment of skeletal muscle atrophy or methods for inducing skeletal muscle hypertrophy utilizing VPAC receptors as the target for intervention.

SEQUENCE LISTING DESCRIPTION

Each of the VPAC receptor protein sequences included in the sequence listing, along with the corresponding Genbank accession number and animal species from which it is cloned, is shown in Table 1.

TABLE I

| VPAC Receptor subtype | SEQ ID NO: | SPECIES | CORRESPONDING GENBANK ACCESSION NOS. |
|---|---|---|---|
| VPAC$_1$ Receptor | 1 | human | L13288, U11087 |
| VPAC$_1$ Receptor | 2 | human | X75299 |
| VPAC$_1$ Receptor | 3 | Rattus norvegicus | M86835 |
| VPAC$_1$ Receptor | 4 | Mus musculus | NM_011703 |
| VPAC$_1$ Receptor | 5 | Sus scrofa | U49434 |
| VPAC$_1$ Receptor | 6 | Rana ridibunda | AF100644 |
| VPAC$_1$ Receptor | 7 | Porcine | I28734 |
| VPAC$_1$ Receptor | 8 | Rattus sp | E05551 |
| VPAC$_1$ Receptor | 9 | Carassius auratus | US6391 |
| VPAC$_2$ Receptor | 10 | human | X95097, Y18423 |
| VPAC$_2$ Receptor | 11 | human | L40764, L36566 |
| VPAC$_2$ Receptor | 12 | human | U18810 |
| VPAC$_2$ Receptor | 13 | Mus musculus | D28132 |
| VPAC$_2$ Receptor | 14 | Rattus norvegicus | Z25885 |
| VPAC$_2$ Receptor | 15 | Rattus norvegicus | U09631 |
| VPAC$_2$ Receptor | 16 | Rat | A43808 |

BACKGROUND

VPAC and Ligands

Vasoactive intestinal peptide (VIP) and its functionally and structurally related analogs (VIP analogs), are known to have many physiological functions including smooth muscle relaxation (bronchodilation, intestinal motility), regulation of microvascular tone (vasodepression) and permeability, regulation of mucus secretion, modulation of various inmmune functions (anti-inflammation, immune cell protection), neurological effects (memory improvement, hypnogenesis, food intake, circadian rhythm control, sexual behavior), maintenance of salivary gland function, developmental growth regulation and stimulation of hormone secretion (prolactin, growth hormone, insulin). VIP and VIP analogs mediate their effects through vasoactive intestinal peptide receptors via both neuronal (as putative neurotransmitters) and neuroendocrine pathways. There are two VPAC receptors identified to date (VPAC$_1$ and VPAC$_2$). The VPAC$_1$ receptor has been cloned from human, mouse (Mus musculus), rat (Rattus norvegicus and Rattus sp.), pig (Sus scrofa), frog (Rana ridibunda), goldfish (Carassius auratus), and turkey (Meleagris gallopavo). The VPAC$_2$ receptor has been cloned from human, mouse (Mus musculus), and rat (Rattus norvegicus).

VPAC$_1$ and VPAC$_2$ receptors are classified in the pituitary adenylate cyclase-activating polypeptide (PACAP) receptor family based on sequence homology to other members of the PACAP family. Receptors in the PACAP family are further subdivided into two subclasses based on ligand affinity. The PACAP type I receptors have a much greater affinity for PACAP than for VIP, while the PACAP type II receptors have an approximately equal affinity for PACAP and VIP. Because VPAC$_1$ and VPAC$_2$ receptors have similar affinities for PACAP and VIP, these receptors are classified as PACAP type II receptors. Selective agonists and antagonists can differentiate VPAC$_1$ and VPAC$_2$ receptors from each other, both molecularly and pharmacologically, as well as from the PACAP type I receptors. These agonist and antagonists have been useful in matching biological activity to a particular VPAC receptor subclass.

VPAC$_1$ and VPAC$_2$ receptors both belong to the G-protein coupled receptor (GPCR) class. The specificity of coupling of VPAC$_1$ and VPAC$_2$ receptors to a particular G-protein, appears to depend upon the tissue examined. In tissues such as muscle, agonist activation of VPAC$_1$ or VPAC$_2$ receptors leads to $G_{\alpha s}$ activation of adenylate cyclase. Adenylate cyclase catalyzes the formation of cAMP which in turn has multiple effects including the activation of protein kinase A, intracellular calcium release and mitogen-activated protein kinase (MAP kinase) activation. In other studies, the enhancement of intracellular inositol triphosphate synthesis after agonist activation of VPAC receptors suggests VPAC receptor coupling to either $G_{\alpha i}$ or $G_{\alpha q}$.

Expression of VPAC$_1$ and VPAC$_2$ receptors is tissue specific and the pattern of expression of each receptor differs. In humans, the VPAC$_1$ receptor has been shown to be expressed in brain, adipose, liver, and heart, while the VPAC$_2$ receptor has been shown to be expressed in lung, pancreas, brain, kidney, skeletal muscle, stomach, heart, and placenta. In the rat, expression of the VPAC$_1$ receptor has been found in the pineal gland, small intestine, liver, spleen, pancreas, lung, aorta, vas deferens and brain, while expression of the VPAC$_2$ receptor has been shown in the stomach, intestine, skeletal muscle, spleen, pancreas, thymus, adrenal gland, heart, lung, aorta, brain, pituitary, and olfactory bulb.

Skeletal Muscle Atrophy and Hypertrophy

Skeletal muscle is a plastic tissue which readily adapts to changes in either physiological demand for work or metabolic need. Hypertrophy refers to an increase in skeletal muscle mass while skeletal muscle atrophy refers to a decrease in skeletal muscle mass. Acute skeletal muscle atrophy is traceable to a variety of causes including, but not limited to: disuse due to surgery, bed rest, or broken bones; denervation/nerve damage due to spinal cord injury, autoimmune disease, or infectious disease; glucocorticoid use for unrelated conditions; sepsis due to infection or other causes; nutrient limitation due to illness or starvation; and space travel. Skeletal muscle atrophy occurs through normal biological processes, however, in certain medical situations this normal biological process results in a debilitating level of muscle atrophy. For example, acute skeletal muscle atrophy presents a significant limitation in the rehabilitation of patients from immobilizations, including, but not limited to, those accompanying an orthopedic procedure. In such cases, the rehabilitation period required to reverse the skeletal muscle atrophy is often far longer than the period of time required to repair the original injury. Such acute disuse atrophy is a particular problem in the elderly, who may already suffer from substantial age-related deficits in muscle function and mass, because such atrophy can lead to permanent disability and premature mortality.

Skeletal muscle atrophy can also result from chronic conditions such as cancer cachexia, chronic inflammation, AIDS cachexia, chronic obstructive pulmonary disease (COPD), congestive heart failure, genetic disorders, e.g. muscular dystrophies, neurodegenerative diseases and sarcopenia (age associated muscle loss). In these chronic conditions, skeletal muscle atrophy can lead to premature loss of mobility, thereby adding to the disease related morbidity.

Little is known regarding the molecular processes which control atrophy or hypertrophy of skeletal muscle. While the initiating trigger of the skeletal muscle atrophy is different for the various atrophy initiating events, several common biochemical changes occur in the affected skeletal muscle fiber, including a decrease in protein synthesis and an increase in protein degradation and changes in both contractile and metabolic enzyme protein isozymes characteristic of a slow (highly oxidative metabolism/slow contractile protein isoforms) to fast (highly glycolytic metabolism/fast contractile protein isoforms) fiber switch. Additional changes in skeletal muscle which occur include the loss of vasculature and remodeling of the extracellular matrix. Both fast and slow twitch muscle demonstrate atrophy under the appropriate conditions, with the relative muscle loss depending on the specific atrophy stimuli or condition. Importantly, all these changes are coordinately regulated and are switched on or off depending on changes in physiological and metabolic need.

The processes by which atrophy and hypertrophy occur are conserved across mammalian species. Multiple studies have demonstrated that the same basic molecular, cellular, and physiological processes occur during atrophy in both rodents and humans. Thus, rodent models of skeletal muscle atrophy have been successfully utilized to understand and predict human atrophy responses. For example, atrophy induced by a variety of means in both rodents and humans results in similar changes in muscle anatomy, cross-sectional area, function, fiber type switching, contractile protein expression, and histology. In addition, several agents have been demonstrated to regulate skeletal muscle atrophy in both rodents and in humans. These agents include anabolic steroids, growth hormone, insulin-like growth factor I, and beta adrenergic agonists. Together, these data demonstrate that skeletal muscle atrophy results from common mechanisms in both rodents and humans.

While some agents have been shown to regulate skeletal muscle atrophy and are approved for use in humans for this indication, these agents have undesirable side effects such as hypertrophy of cardiac muscle, neoplasia, hirsutism, androgenization of females, increased morbidity and mortality, liver damage, hypoglycemia, musculoskeletal pain, increased tissue turgor, tachycardia, and edema (54th Edition of the Physicians Desk Reference, 2000). Currently, there are no highly effective and selective treatments for either acute or chronic skeletal muscle atrophy. Thus, there is a need to identify other therapeutic agents which regulate skeletal muscle atrophy.

One problem associated with identification of compounds for use in the treatment of skeletal muscle atrophy has been the lack of good screening methods for the identification of such compounds. Applicants have now found that $VPAC_1$ and $VPAC_2$ receptors are involved in the regulation of skeletal muscle mass or function and that agonists of $VPAC_1$ and $VPAC_2$ receptors are able to block skeletal muscle atrophy and/or induce hypertrophy of skeletal muscle.

SUMMARY OF THE INVENTION

The present invention relates to the use of VPAC receptors to identify candidate compounds that are potentially useful in the treatment of skeletal muscle atrophy and/or useful to induce skeletal muscle hypertrophy. In particular, the invention provides in vitro methods for identifying candidate compounds for regulating skeletal muscle mass or function. In one embodiment of the invention the method comprises: contacting a test compound with a VPAC receptor, and determining whether the test compound binds to the VPAC receptor, wherein test compounds that bind to the VPAC receptor are identified as candidate compounds for regulating skeletal muscle mass or function. In another embodiment of the invention the method comprises: contacting a test compound with a cell expressing a VPAC receptor, and determining whether the test compound activates the VPAC receptor, wherein test compounds that activate the VPAC receptor are identified as candidate compounds for regulating skeletal muscle mass or function. In yet another embodiment of the invention the method further comprises generating a list of candidate compounds.

In another aspect, the present invention relates to the use of VPAC receptors to identify candidate therapeutic compounds which regulate skeletal muscle mass or function in vivo. In particular, the invention provides a method comprising: contacting a test compound with a VPAC receptor, determining whether the test compound binds to the VPAC receptor, administering a test compound determined in the previous step to bind to the VPAC receptor, or previously known to bind to the VPAC receptor, to a non-human animal and determining whether the test compound regulates skeletal muscle mass or muscle function in the treated animal. Those test compounds that regulate skeletal muscle mass or function are identified as candidate therapeutic compounds for regulating skeletal muscle mass or function in vivo. In another embodiment of the invention the method comprises: contacting a test compound with a cell expressing VPAC receptors, determining whether the test compound activates the VPAC receptor, administering a test compound determined in the previous step to activate the VPAC receptor, or previously known to activate the VPAC receptor, to a non-human animal and determining whether the test compound regulates skeletal muscle mass or muscle function in the treated animal. Those test compounds that regulate skeletal muscle mass or function in vivo are identified as candidate therapeutic compounds for regulating skeletal muscle mass or function in vivo.

The invention further provides methods for identifying candidate compounds that prolong or augment the activation of VPAC receptors or of a VPAC receptor signal transduction pathway. These methods comprise, (i) contacting a cell which expresses functional VPAC receptors with a VPAC receptor agonist at a concentration of agonist and for a period of agonist-receptor exposure sufficient to allow desensitization of the receptor; (ii) contacting the cells with a test compound; and (iii) determining the level of activation of the VPAC receptor. In the above-described embodiment of the invention, step (ii) may be performed before or after step (i). In a particular embodiment, the present invention relates to a method of determining whether those candidate compounds that prolong or augment the agonist-induced activation of VPAC receptors or a VPAC receptor signal transduction pathway, can be used to regulate skeletal muscle mass or function in vivo by administering a candidate compound, alone or in conjunction with a VPAC receptor agonist, to a non-human animal and determining whether the candidate compound regulates skeletal muscle mass or function in the treated animal. Those candidate compounds that regulate skeletal muscle mass or function in vivo are identified as candidate therapeutic compounds for regulating skeletal muscle mass or function in vivo.

The invention further provides methods for identifying candidate compounds that increase VPAC receptor expression comprising contacting a test compound with a cell or cell lysate containing a reporter gene operatively associated with a VPAC receptor gene regulatory element and detecting expression of the reporter gene. Test compounds that increase expression of the reporter gene are identified as candidate compounds for increasing VPAC receptor expression. In a particular embodiment, the present invention relates to a method of determining whether those candidate compounds which increase VPAC receptor expression can be used to regulate skeletal muscle mass or function in vivo by administering a candidate compound to a non-human animal and determining whether the candidate compound regulates skeletal muscle mass or function in the treated animals. Those candidate compounds that regulate skeletal muscle mass or function in vivo are identified as candidate therapeutic compounds for regulating skeletal muscle mass or function in vivo.

In another embodiment the invention provides for antibodies specific for VPAC receptors. In particular the invention provides for chimeric or human antibodies specific for VPAC receptors.

The invention additionally provides methods for identifying compounds that increase VIP or VIP analog expression which include the steps of contacting a test compound with a cell or cell lysate containing a reporter gene operatively associated with a VIP or VIP analog gene regulatory element and detecting expression of the reporter gene. Test compounds that increase reporter gene expression are identified as candidate compounds which increase VIP or VIP analog expression. In a particular embodiment, the present invention relates to a method of determining whether those candidate compounds which increase VIP or VIP analog expression regulate skeletal muscle mass or function in vivo by administering a candidate compound to a non-human animal and determining whether the candidate compound regulates skeletal muscle mass or function in the treated animal. Those candidate compounds that regulate skeletal muscle mass or function in vivo are identified as candidate therapeutic compounds for regulating skeletal muscle mass or function in vivo.

The present invention also relates to use of a VPAC receptor as a therapeutic target to increase skeletal muscle mass or function. This use includes, the use of a VPAC receptor agonist, a compound that prolongs or augments the activation of VPAC receptors or the activation of a VPAC receptor signal transduction pathway, an expression vector encoding a functional VPAC receptor, an expression vector encoding a constitutively active VPAC receptor, a compound that increases expression of VPAC receptors, a compound that increases expression of VIP or a compound that increases expression of a VIP analog to increase skeletal muscle mass or function and/or to treat skeletal muscle atrophy. In particular, the invention provides a method for increasing skeletal muscle mass or function in a subject in which such an increase is desirable, comprising: identifying a subject in which an increase in skeletal muscle mass or function is desirable and administering to the subject a safe and effective amount of a VPAC receptor agonist, a compound that prolongs or augments the activation of VPAC receptors or the activation of a VPAC receptor signal transduction pathway, an expression vector encoding a functional VPAC receptor, an expression vector encoding a constitutively active VPAC receptor, a compound that increases expression of VPAC receptors, a compound that increases expression of VIP or a compound that increases expression of a VIP analog. In another embodiment, the invention provides methods of treating skeletal muscle atrophy, in a subject in need of such treatment, comprising administering to the subject an effective amount of a VPAC receptor agonist, a compound that prolongs or augments the activation of VPAC receptors or the activation of a VPAC receptor signal transduction pathway, an expression vector encoding a functional VPAC receptor, an expression vector encoding a constitutively active VPAC receptor, a compound that increases expression of VPAC receptors, a compound that increases expression of VIP or a compound that increases expression of VIP analog.

The present invention also relates to the use of a compound that prolongs or augmemts the activation of VPAC receptors, or of a VPAC receptor signal transduction pathway, to increase skeletal muscle mass or function and/or to treat skeletal muscle atrophy. In particular, the invention provides methods of treating skeletal muscle atrophy, in a subject in need of such treatment, comprising administering, alone or in conjunction with a VPAC receptor agonist, a safe and effective amount of a compound that prolongs or augments the activation of VPAC receptors, or of a VPAC receptor signal transduction pathway.

DESCRIPTION OF THE FIGURES

Abbreviations used in FIGS. 1–5:

$VPAC_1R$ agonist—$[K^{15}, R^{16}, L^{27}VIP(1-7), GRF(8-27)-NH_2]$ $VPAC_2R$ agonist—Ro 25-1553

PACAP-38—$VPAC_1/VPAC_2$ receptor non-selective agonist

Saline—physiological saline (vehicle control)

T—theophylline (30 mg/kg—administered 2× daily g—gram

*—statistically significant response versus saline

Figure 1A:
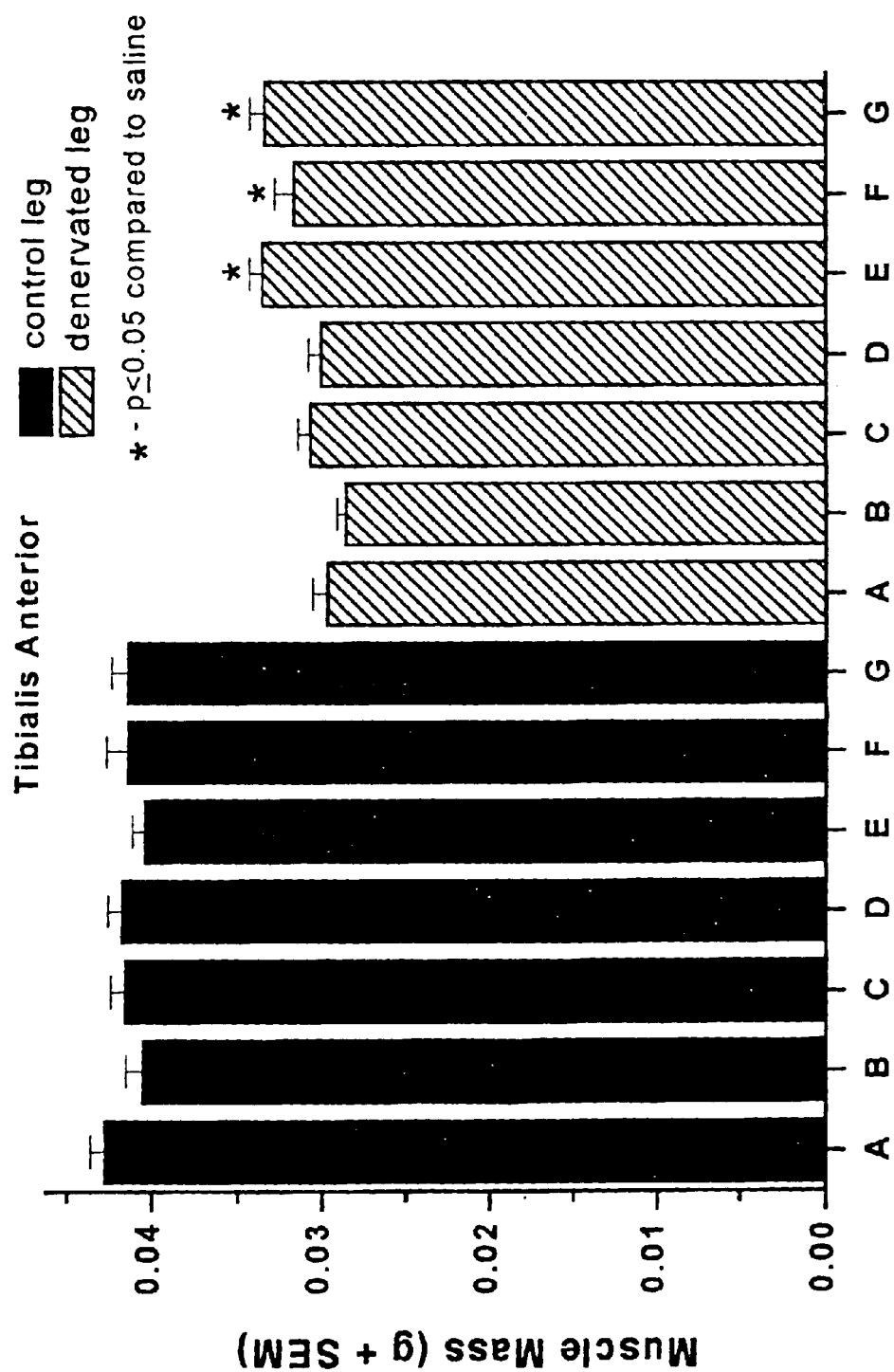
Figure 1B:
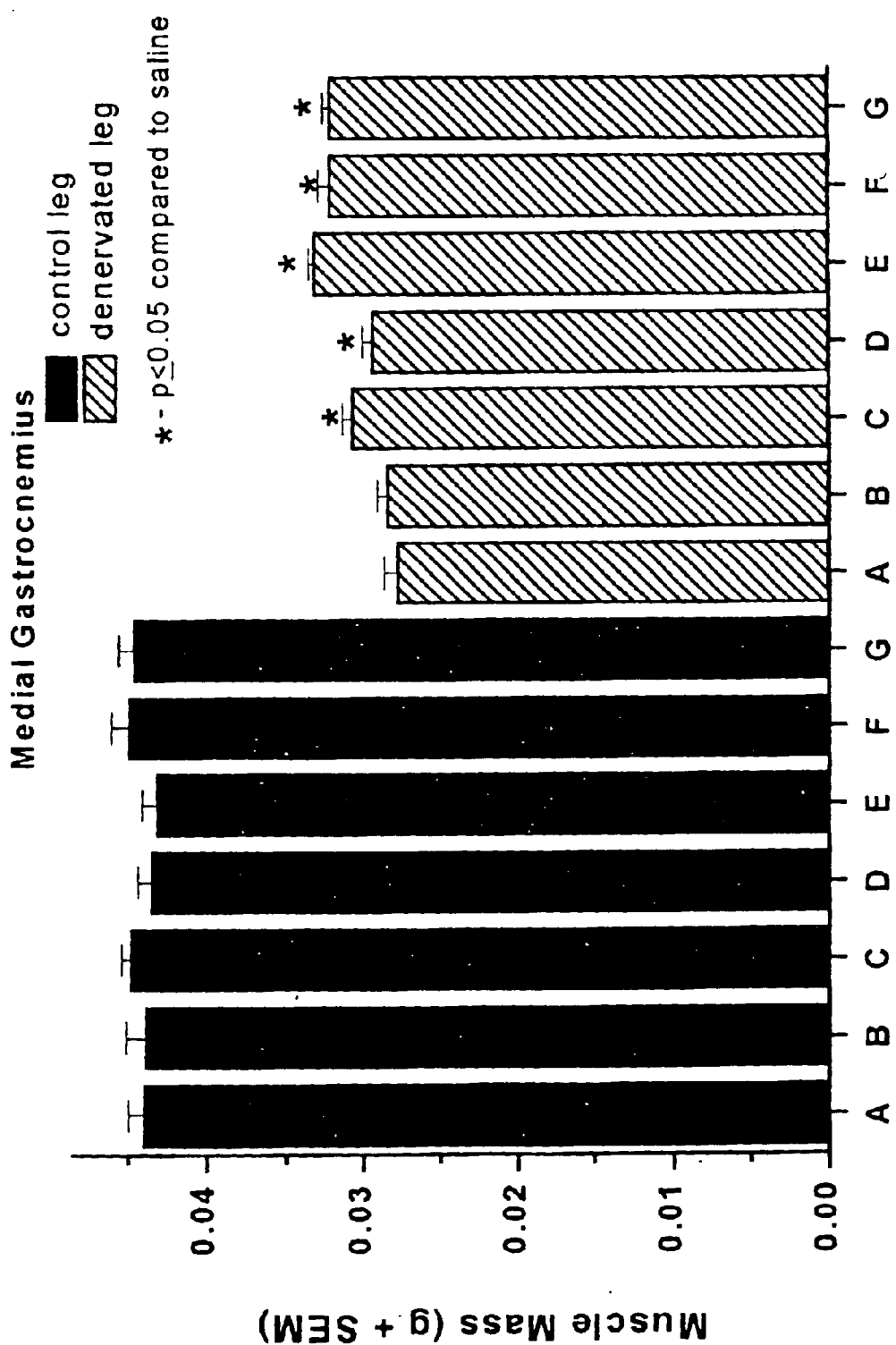

FIGS. 1A and 1B demonstrate the anti-atrophy effects of $VPAC_1$ and $VPAC_2$ receptor agonists (administered subcutaneously, 2× daily) in the mouse denervation atrophy model. FIG. 1A shows the anti-atrophy effects of $VPAC_1$ and $VPAC_2$ receptor selective agonists in denervated tibialis anterior muscle. FIG. 1B shows the anti-atrophy effects of $VPAC_1$ and $VPAC_2$ receptor selective agonists in denervated medial gastrocnemius muscle. Legend for the X-axis: A: Saline, B: $VPAC_1R$ agonist (0.1 mg/kg)+T, C: $VPAC_1R$ agonist (0.3 mg/kg)+T, D: $VPAC_2R$ agonist (0.1 mg/kg)+T, E: $VPAC_2R$ agonist (0.3 mg/kg)+T, F: PACAP-38 (0.1 mg/kg)+T, G: PACAP-38 (0.3 mg/kg)+T.

Figure 2A:
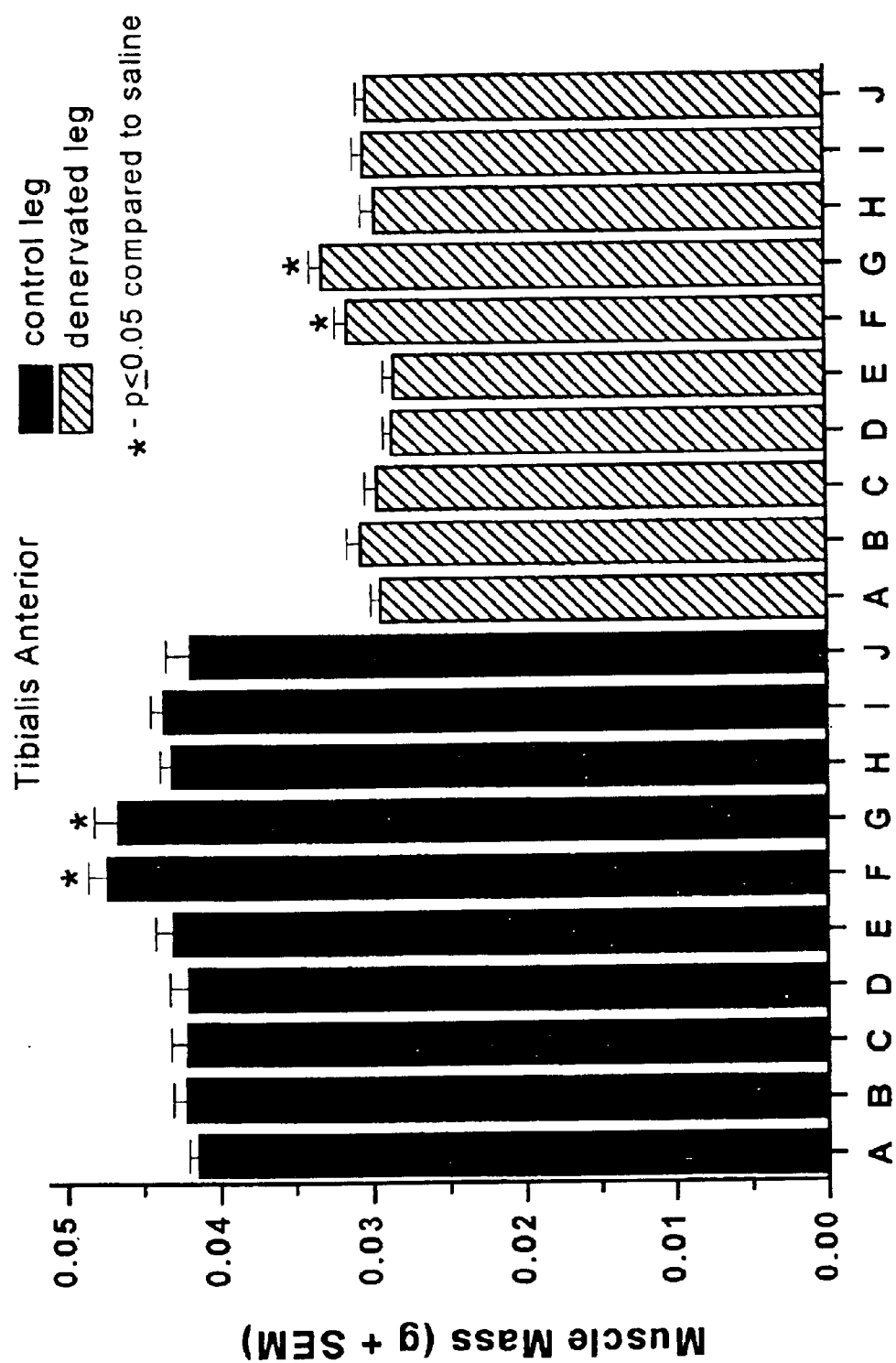
Figure 2B:
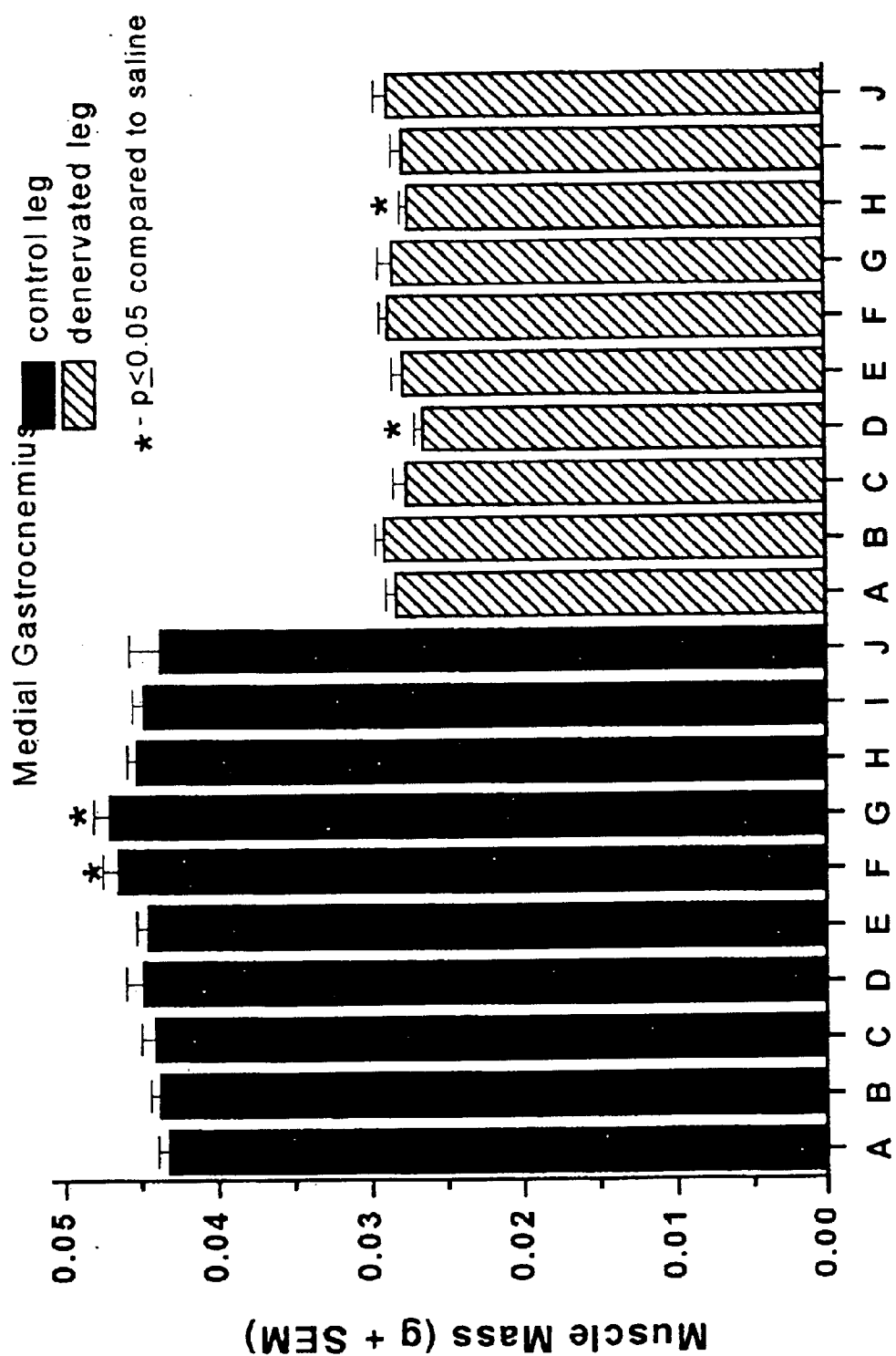

FIGS. 2A and 2B demonstrate the anti-atrophy and hypertrophy-inducing effects of $VPAC_1$ and $VPAC_2$ receptor selective agonists (administered continuously by osmotic minipump) in the mouse denervation atrophy model. FIG. 2A shows the anti-atrophy and hypertrophy-inducing effects of the $VPAC_2$ receptor selective agonist in denervated and normal tibialis anterior muscle. FIG. 2B shows the hypertrophy-inducing effects of the $VPAC_2$ receptor selective agonist in normal medial gastrocnemius muscle. Legend for the X-axis: A: water infused, B: $VPAC_1R$ agonist (0.3 mg/kg), C: $VPAC_1R$ agonist (1 mg/kg), D: $VPAC_1R$ agonist (3 mg/kg), E: $VPAC_2R$ agonist (0.3 mg/kg), F: $VPAC_2R$ agonist (1 mg/kg), G: $VPAC_2R$ agonist (3 mg/kg), H: PACAP-38 (0.3 mg/kg), I: PACAP-38 (1 mg/kg), PACAP-38 (3 mg/kg).

Figure 3A:
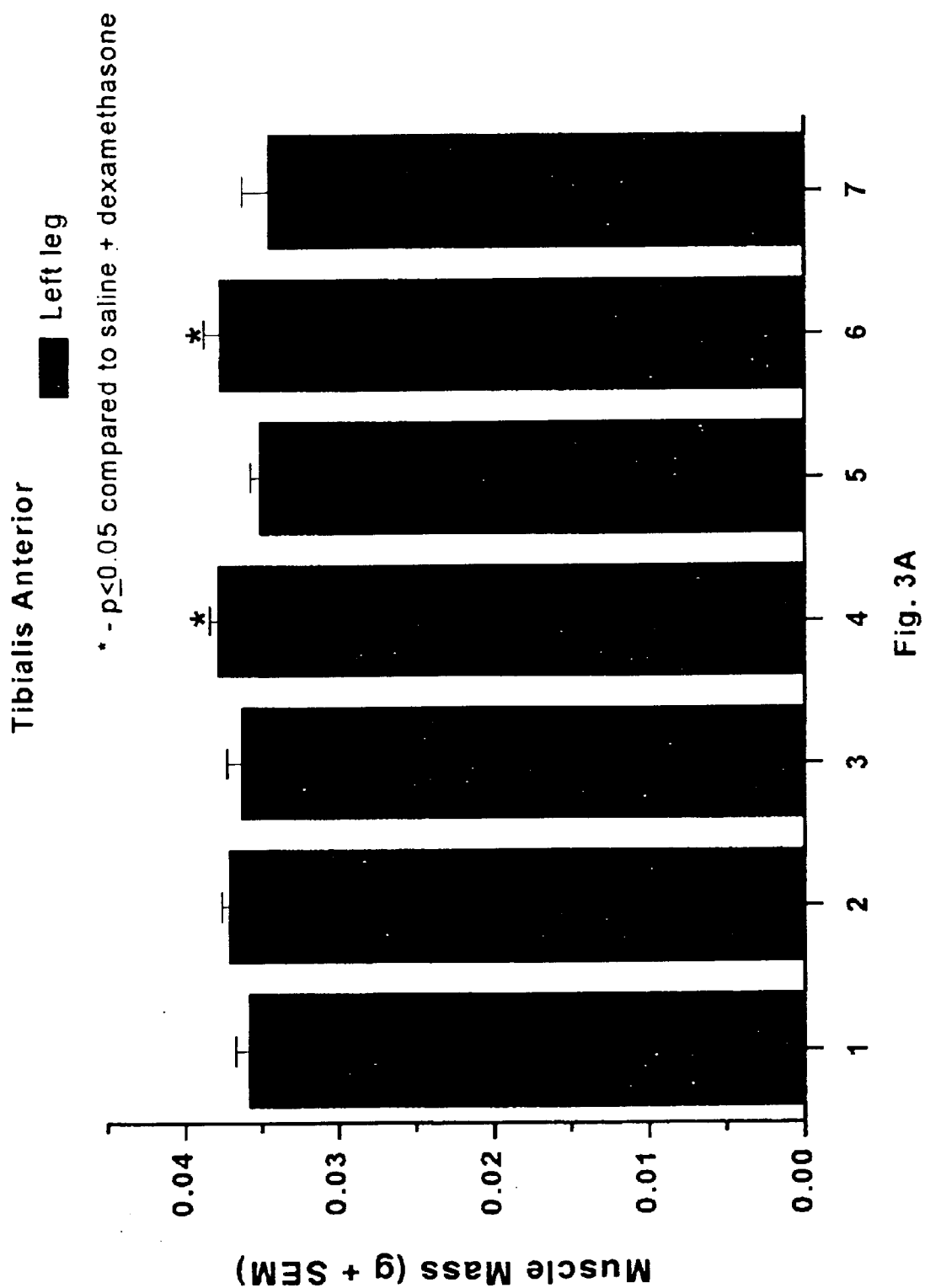
Figure 3B:
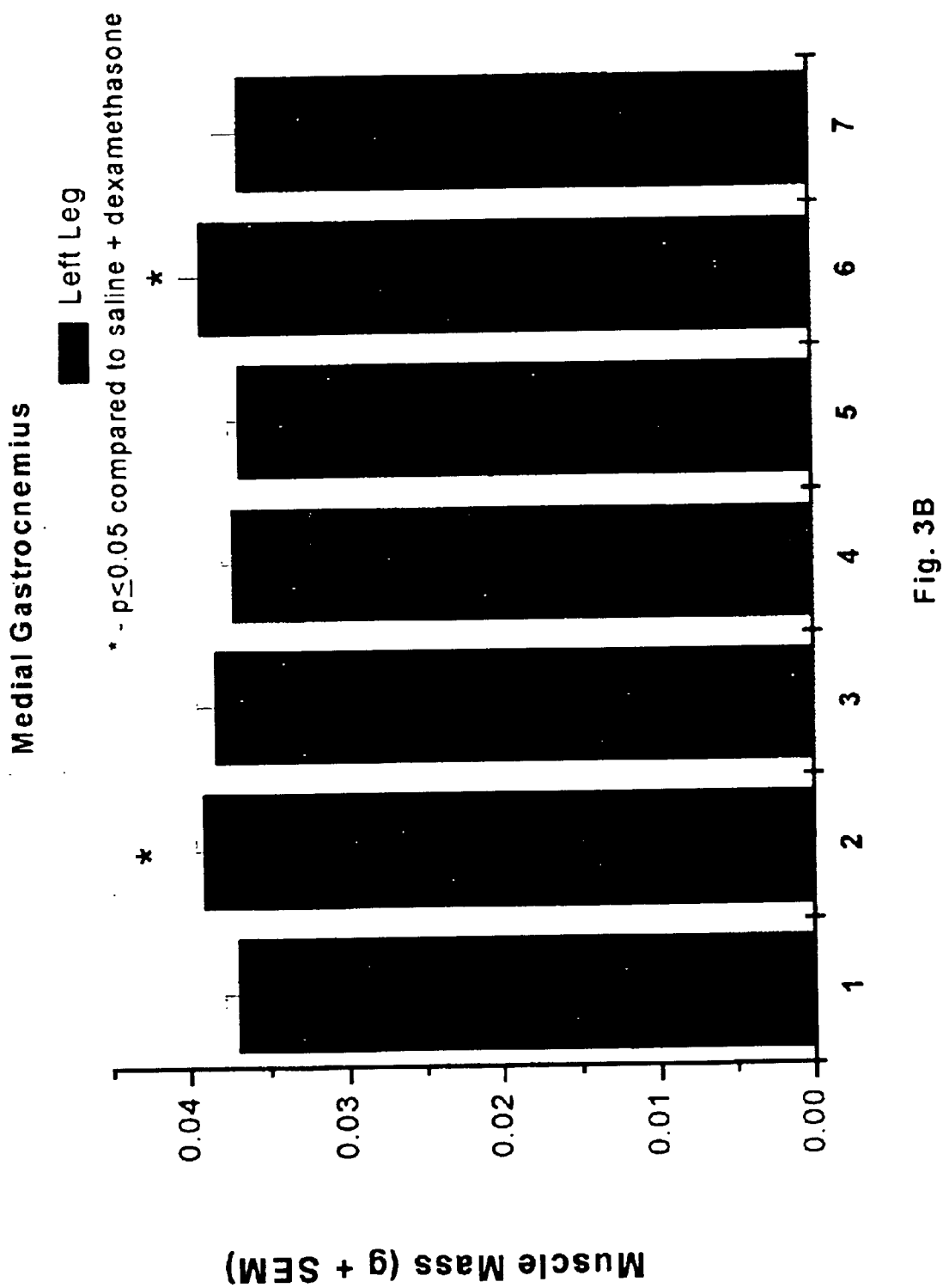

FIGS. 3A and 3B demonstrate the anti-atrophy effects of $VPAC_1$ and $VPAC_2$ receptor selective agonists (administered subcutaneously, 2× daily) in the mouse glucocorticoid (dexamethasone)-induced atrophy model. FIG. 3A shows the anti-atrophy effects of $VPAC_1$ and $VPAC_2$ receptor selective agonists in glucocorticoid-induced atrophied tibialis anterior muscle. FIG. 3B shows the anti-atrophy effects of $VPAC_1$ and $VPAC_2$ receptor selective agonists in glucocorticoid-induced atrophied medial gastrocnemius muscle. Legend for the X-axis: 1: Saline+Dexamethasone (1.2 mg/kg/day included in the drinking water), 2: PACAP-38 (0.1 mg/kg)+Dexamethasone+T, 3: PACAP-38 (0.3 mg/kg)+Dexamethasone+T, 4: $VPAC_1R$ agonist (0.1 mg/kg)+Dexamethasone+T, 5: $VPAC_1R$ agonist (0.3 mg/kg)+Dexamethasone+T, 6: $VPAC_2R$ agonist (0.1 mg/kg)+Dexamethasone+T, 7: $VPAC_2R$ agonist (0.3 mg/kg)+Dexamethasone+T.

Figure 4A:
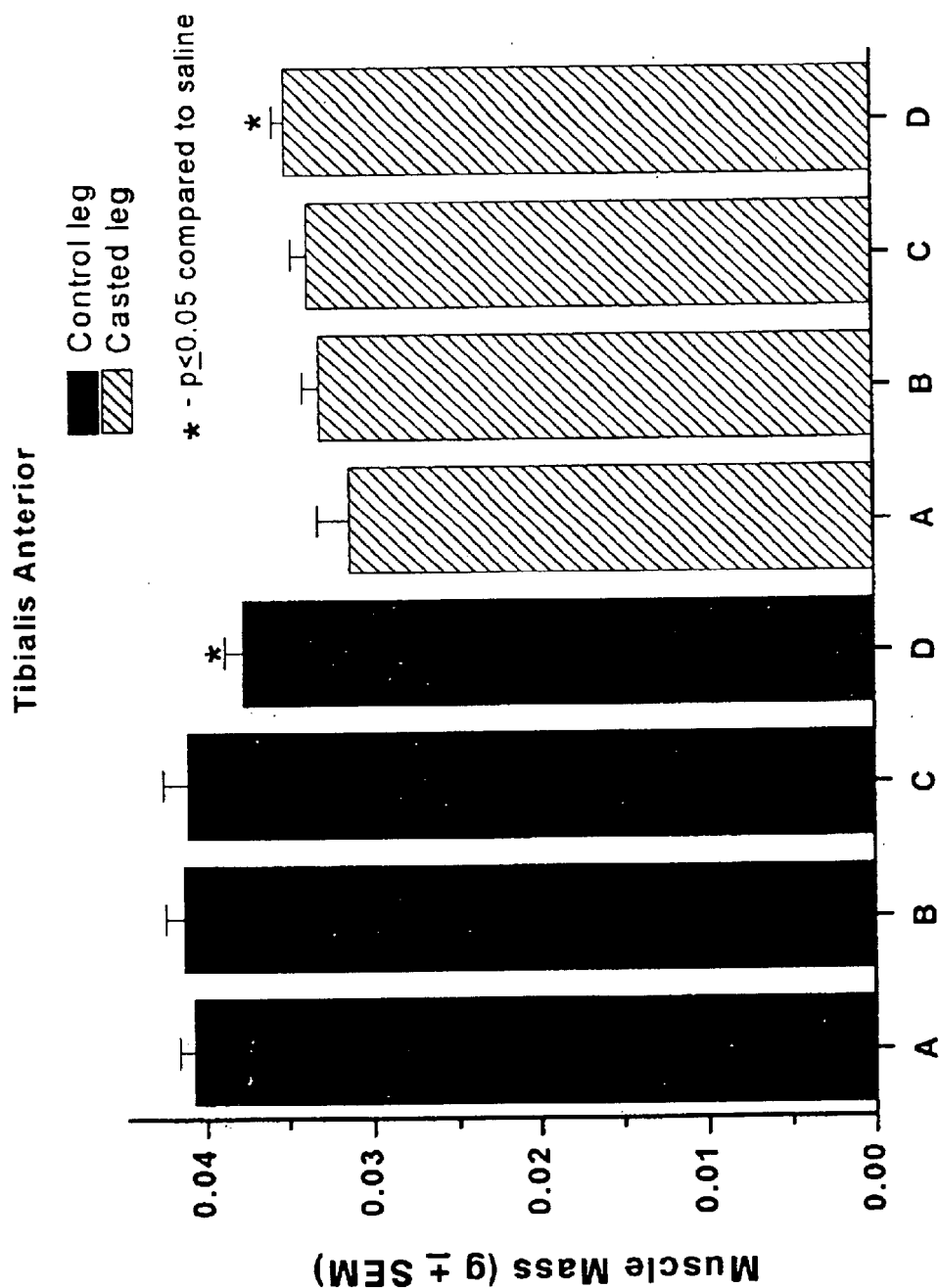
Figure 4B:
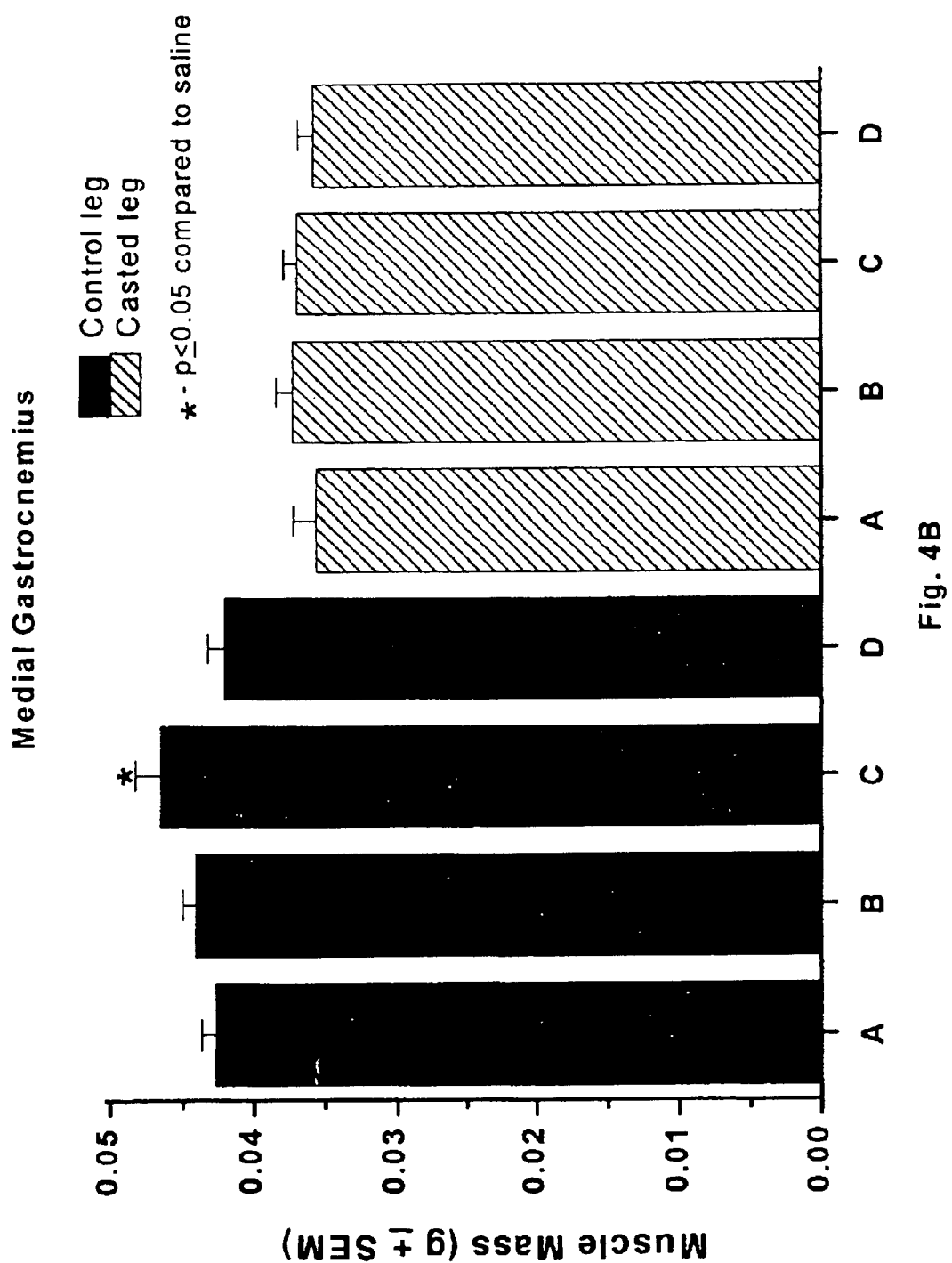

FIGS. 4A and 4B demonstrate the anti-atrophy and hypertrophy-inducing effects of a $VPAC_2$ receptor selective agonist (administered subcutaneously, 2× daily) in the mouse disuse (casting) atrophy model. FIG. 4A shows the anti-atrophy effects of the $VPAC_2$ receptor selective agonist, Ro 25-1553, in casting-induced atrophied tibialis anterior muscle. FIG. 4B shows the hypertrophy-inducing effects of $VPAC_2$ receptor selective agonist, Ro 25-1553 in normal medial gastrocnemius muscle. Legend for the X-axis: A: Saline, B: $VPAC_2R$ agonist (0.03 mg/kg)+T, C: $VPAC_2R$ agonist (0.1 mg/kg)+T, D: $VPAC_2R$ agonist (0.3 mg/kg)+T.

Figure 5A:
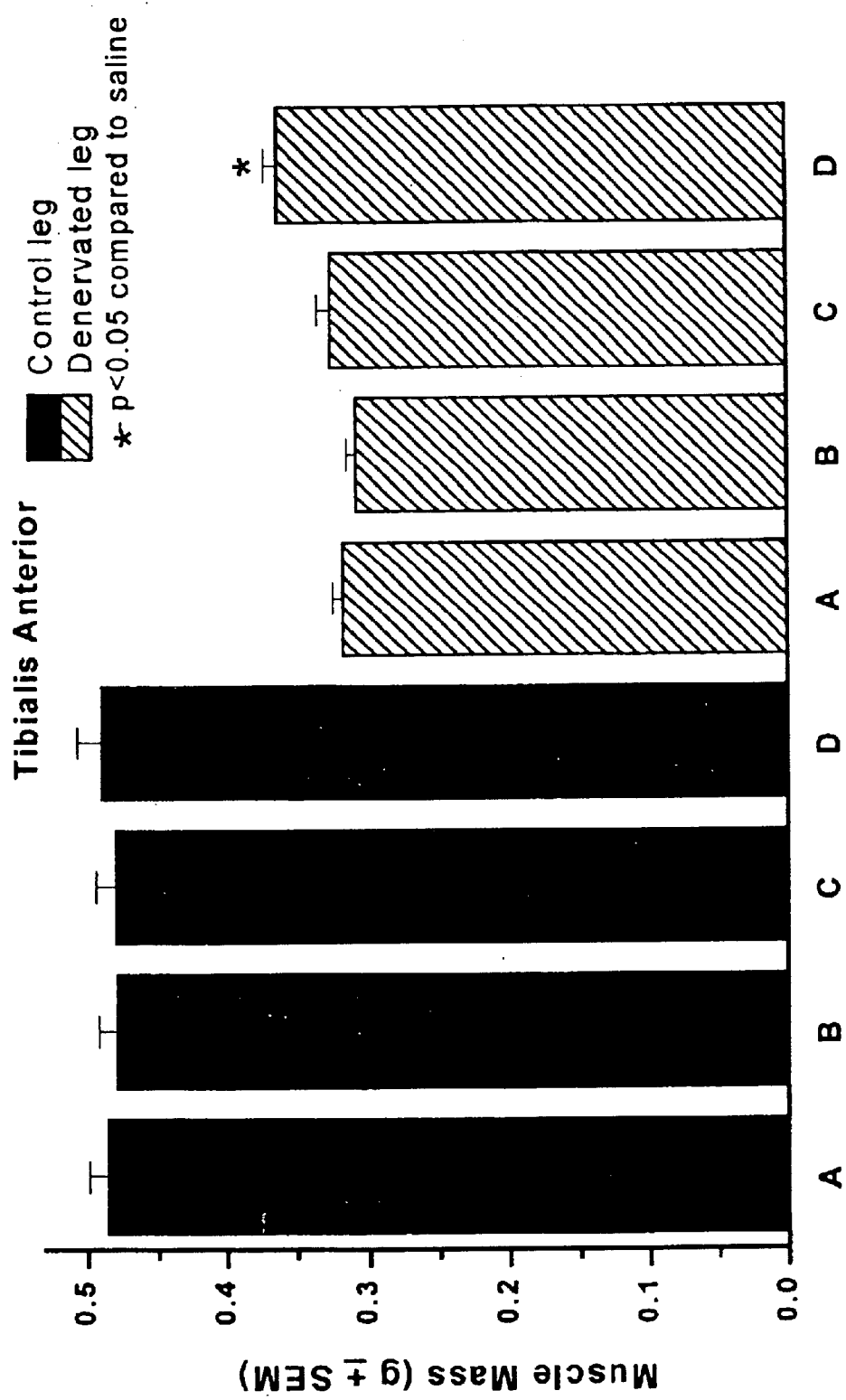
Figure 5B:
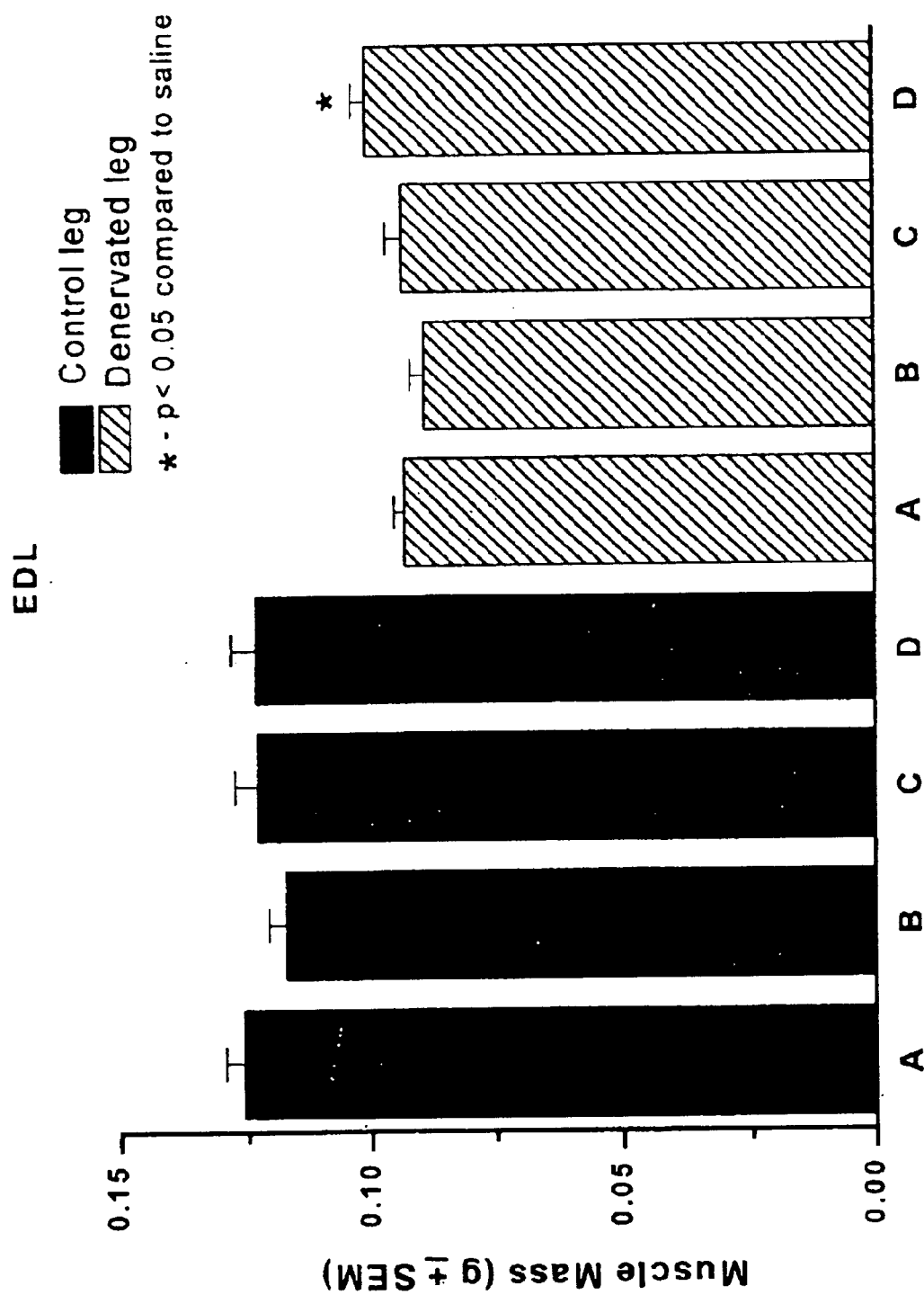

FIGS. 5A and 5B demonstrate the anti-atrophy effects of a $VPAC_2$ receptor selective agonist (administered subcutaneously, 2× daily) in the rat denervation atrophy model. FIG. 5A shows the anti-atrophy effects of the $VPAC_2$ receptor selective agonist, Ro 25-1553, in denervation-induced atrophied tibialis anterior muscle. FIG. 5B shows the anti-atrophy effects of $VPAC_2R$ agonist, Ro 25-1553 in denervation-induced atrophied extensor digitorum longus (EDL) muscle. Legend for the X-axis: A: Saline, B: $VPAC_2R$ agonist (0.03 mg/kg)+T, C: $VPAC_2R$ agonist (0.1 mg/kg)+T, D: $VPAC_2R$ agonist (0.3 mg/kg)+T.

DETAILED DESCRIPTION OF THE INVENTION

I. Terms and Definitions

The following is a list of definitions for terms used herein.

"Agonist" means any compound that activates a receptor.

"Allelic variant" means a variant form of a given gene or gene product. One of skill in the art recognizes that a large number of genes are present in two or more allelic forms in a population and some genes have numerous alleles.

"Antibody", in its various grammatical forms, means immunoglobulin molecules and immunologically active portions of immunoglobulin molecules, i.e., molecules that contain an antigen binding site which specifically binds an antigen. "Purified antibody" means an antibody which has been partially or completely separated from the proteins and naturally-occurring organic molecules with which it is naturally associated. Preferably, the preparation is at least 60% antibody, more preferably at least 75% antibody, more preferably at least 90% antibody, and most preferably at least 99%, by dry) weight, antibody.

"Binding affinity" means the propensity for a ligand to interact with a receptor and is inversely related to the dissociation constant for a specific VIP ligand-VPAC interaction. The dissociation constant can be measured directly via standard saturation, competition, or kinetics binding techniques or indirectly via pharmacological techniques involving functional assays and endpoints.

"Chimeric antibody" means an antibody that contains structural elements from two or more different antibody molecules, i.e. from different animal species. Chimeric antibodies include, but are not limited to, antibodies known as "humanized antibodies" which include, but are not limited to, chimeric antibodies generated by the technique known as complementarity determining region grafting.

"Fusion" means two or more DNA coding sequences operably associated so as to encode one hybrid protein. A "fusion protein" therefore refers to such a hybrid protein.

"Inhibit" means to partially or completely block a particular process or activity. For example, a compound inhibits skeletal muscle atrophy if it either completely or partially prevents muscle atrophy.

As used herein, two DNA sequences are said to be "operably associated" if the nature of the linkage between the two DNA sequences does not (1) result in the introduction of a frame-shift mutation, (2) interfere with the ability of a promoter region to direct the transcription of the coding sequences, or (3) interfere with the ability of the corresponding RNA transcript to be translated into a protein. For example, a coding sequence and regulatory sequences are operably associated when they are covalently linked in such a way as to place the transcription of the coding sequence under the influence or control of the regulatory sequences. Thus, a promoter region is operably associated with a coding sequence when the promoter region is capable of effecting transcription of that DNA sequence such that the resulting transcript is capable of being translated into the desired protein or polypeptide.

"PACAP" means pituitary adenylate cyclase-activating polypeptide.

"Percent identity" means the percentage of nucleotides or amino acids that two sequences have in common as calculated as follows. To calculate the percent identity for a specific sequence (the query), the relevant part of the query sequence is compared to a reference sequence using the BestFit comparison computer program, Wisconsin Package, Ver. 10.1, available from the Genetics Computer Group, Inc. This program uses the algorithm of Smith and Waterman, *Advances in Applied Mathematics,* Issue 2: 482–489 (1981). Percent identity is calculated with the following default parameters for the BestFit program: the scoring matrix is blosum62.cmp, the gap creation penalty is 8 and the Gap extension penalty is 2. When comparing a sequence to the reference sequence, the relevant part of the query sequence is that which is derived from a VPAC sequence. For example, where the query is a VPAC/purification tag fusion protein, only the VPAC polypeptide portion of the sequence is aligned to calculate the percent identity score.

"Polypeptide" means any chain of amino acids, regardless of length or post-translational modification (e.g., phosphorylation or glycosylation).

"Promoter" means a DNA sequence which controls the initiation of transcription and the rate of transcription from a gene or coding region.

"Prophylactic treatment" means preventive treatment of a subject, not currently exhibiting signs of skeletal muscle atrophy, in order to completely or partially block the occurrence of skeletal muscle atrophy. One of skill in the art would recognize that certain individuals are at risk for skeletal muscle atrophy as discussed in the background section herein. Furthermore, one of skill in the art would recognize that if the biochemical changes leading to skeletal muscle atrophy are appropriately regulated, that the occurrence of atrophy would be prevented or reduced in at-risk individuals.

"Regulate" in all its grammatical forms, means to increase, decrease or maintain, e.g. to regulate skeletal muscle mass or function means to increase, decrease or maintain the level of skeletal muscle mass or function.

"Regulation of skeletal muscle mass or function" includes regulation of skeletal muscle mass, skeletal muscle function or both.

"Regulatory element" means a DNA sequence that is capable of controlling the level of transcription from an operably associated DNA sequence. Included within this definition of regulatory element are promoters and enhancers. E.g., a VPAC receptor gene regulatory element is a DNA sequence capable of controlling the level of transcription from the VPAC receptor gene.

"Reporter gene" means a coding sequence whose product can be detected, preferably quantitatively, wherein the reporter gene is operably associated with a heterologous promoter or enhancer element which is responsive to a signal which is to be measured. The promoter or enhancer element in this context is referred to herein as a "responsive element".

"Selective agonist" means that the agonist has significantly greater activity toward a certain receptor(s) compared with other receptors, not that it is completely inactive with regard to other receptors.

"Skeletal muscle hypertrophy" means an increase in skeletal muscle mass or skeletal muscle function or both.

"Skeletal muscle atrophy" means the same as "muscle wasting" and means a decrease in skeletal muscle mass or skeletal muscle function or both.

"Splice variant" means a mRNA or protein which results from alternative exon usage. One of skill in the art recognizes that, depending on cell type, or even within a single cell type, a mRNA may be expressed in a slightly different form, as a splice variant, and thus the translated protein will be different depending upon the mRNA that is expressed.

A "therapeutically effective amount" of a substance is an amount capable of producing a medically desirable result in a treated subject, e.g., decreases skeletal muscle atrophy, increases skeletal muscle mass or increases skeletal muscle function, with an acceptable benefit: risk ratio; in a human or non-human mammal.

"Therapeutic treatment" means treatment of a subject in which an increase in muscle mass or muscle function is desirable. For example, treatment of a subject currently exhibiting signs of skeletal muscle atrophy in order to partially or completely reverse the skeletal muscle atrophy that has occurred or to completely or partially block the occurrence of further skeletal muscle atrophy would be therapeutic treatment of that subject. The term "therapeutic treatment" also includes, for example, treatment of a subject not exhibiting signs of skeletal muscle atrophy to induce skeletal muscle hypertrophy, e.g. treatment of a livestock animal to increase muscle mass The term "treatment" means prophylactic or therapeutic treatment.

"VIP" means vasoactive intestinal peptide.

"VIP analog" means polypeptides which act as ligands of VPAC receptors. Preferred VIP analogs are PACAP-27, PACAP-38, helodermin, peptide histidine isoleucine amide (PHI), peptide histidine methionine amide, peptide histidine valine amide (PHV), growth hormone releasing hormone, secretin, glucagons, (Arg15, Arg21) VIP, [(Arg15,20, 21Leu17)-VIP-Gly-Lys-Arg-NH2], [$K^{15}$, $R^{16}$, $L^{27}$,VIP (1–7), GRF(8–27)-$NH_2$], multimeric VIP fusion proteins, Ro25-1553, Ro 25-1392 or PACAP(6–38). More preferred VIP analogs are VIP, PACAP-27, PACAP-38, PHI, PHV, Ro25-1553, Ro 25-1392 and [$K^{15}$, $R^{16}$, $L^{27}$,VIP(1–7), GRF (8–27)-$NH_2$].

"VPAC receptor agonist" means a compound or molecule which has the ability to activate the $VPAC_1$ or the $VPAC_2$ receptor, or both. Activation of VPAC receptors can be measured as described hereinafter.

The nomenclature regarding the VPAC receptors used herein follows the convention proposed by Harmar, et al. in *Pharmacological Reviews* (1998) 50(2): 265–270.

"VPAC receptor" means the $VPAC_1$ receptor or $VPAC_2$ receptor.

"$VPAC_1$ receptor" means the $VPAC_1$ receptor from any animal species. The $VPAC_1$ receptor has previously been referred to as the "VIP receptor", "$VIP_1$ receptor" (Lutz et al., *FEBS Lett* (1993) 334:3–8, "VIP/PACAP Type II Receptor" (Ciccarelli et al., *Regul Pept* (1994) 54:397–407, "HIVR" or "human intestinal VIP receptor" (Couvineau, A. et. al., *Biochem. Biophys. Res. Commun.*(1994) 200(2), 769–776, and "PVR2" (Rawlings et al., *Endocrinology* (1995) 136:2088–2098.

The definition of $VPAC_1$ receptor includes, but is not limited to, those receptors for which the cDNA or genomic sequence encoding the receptor has been deposited in a sequence database. These sequences include Accession Nos.: L13288, X75299, M86835, NM_011703, U49434, AF100644, 128734, U31991 (partial cDNA sequence), U56391, E05551 and 806702. The protein sequence of these $VPAC_1$ receptors is obtained by translation of the coding region of these DNA sequences and is generally available as part of the database entry.

"$VPAC_2$ receptor" means the $VPAC_2$ receptor from any animal species. The $VPAC_2$ receptor has also been referred to as "VIP2" (Lutz et al., 1993), "PACAPR-3" (Inagaki et al., (1994) *Proc Natl Academy Sci USA* 91:2679–2683 and "PVR3" (Rawlings et al., (1995) *Endocrinology* 136:2088–2098.

The definition of $VPAC_2$ receptor includes, but is not limited to, those receptors for which the DNA sequence encoding the receptor has been deposited in a sequence database. These sequences include Accession Nos.: X95097, L40764, L36566, Y18423, U18810, D28132, Z25885, U09631 and A43808. The protein sequence of these $VPAC_2$ receptors is obtained by translation of the coding region of these DNA sequences and is generally available as part of the database entry.

The term "VPAC receptor" includes truncated and/or mutated proteins wherein regions of the receptor molecule not required for ligand binding or signaling have been deleted or modified. For example one of skill in the art will recognize that a VPAC receptor with one or more conservative changes in the primary amino acid sequence would be useful in the present invention. It is known in the art that substitution of certain amino acids with different amino acids with similar structure or properties (conservative substitutions) can result in a silent change, i.e. a change that does not significantly alter function. Conservative substitutes are well known in the art. For example, it is known that GPCRs can tolerate substitutions of amino acid residues in the transmembrane alpha-helices, which are oriented toward lipid, with other hydrophobic amino acids, and remain functional. $VPAC_1$ receptors differing from a naturally occurring sequence by truncations and/or mutations such as conservative amino acid substitutions are included in the to definition of $VPAC_1$ receptor. $VPAC_2$ receptors differing from a naturally occurring sequence by truncations and/or mutations such as conservative amino acid substitutions are included in the definition of $VPAC_2$ receptor.

One of skill in the art would also recognize that VPAC receptors from a species other than those listed above, particularly mammalian species, would be useful in the present invention. One of skill in the art would further recognize that by using probes from the known VPAC species' sequences, cDNA or genomic sequences homologous to the known sequence could be obtained from the same or alternate species by known cloning methods. Such $VPAC_1$ receptors are included in the definition of $VPAC_1$ and such $VPAC_2$ receptors are included in the definition of $VPAC_2$.

In addition, one of skill in the art would recognize that allelic variants or splice variants of VPAC receptors might be present in a particular species and that these variants would have utility in the present invention. Such $VPAC_1$ receptor variants are included in the definition of $VPAC_1$ and such $VPAC_2$ receptor variants are included in the definition of $VPAC_2$.

Fusions of a $VPAC_1$ or $VPAC_2$ receptor polypeptide, or a $VPAC_1$ or $VPAC_2$ receptor polypeptide fragment to a non-VPAC polypeptide are referred to as VPAC receptor fusion proteins. Using known methods, one of skill in the art would be able to make fusion proteins of a $VPAC_1$ receptor or a $VPAC_2$ receptor that, while different from native $VPAC_1$ and $VPAC_2$ receptors, would remain useful in the present invention $VPAC_1$ receptor fusion proteins are included within the definition of $VPAC_1$ receptor and $VPAC_2$ receptor fusion proteins are included within the definition of $VPAC_2$ receptor.

"Functional VPAC receptors" refers to VPAC receptors that bind VIP or a VIP analog in vivo or in vitro and are activated as a result of ligand binding.

Unless otherwise defined, all technical and scientific terms used herein have the same meaning as commonly understood by one of ordinary skill in the arts of protein chemistry, pharmacology, or molecular biology. The methods, materials and examples described herein are not intended to be limiting. Other methods and materials similar or equivalent to those described herein can be used in the practice or testing of the present invention.

II. The Role of VPAC Receptors in Regulation of Skeletal Muscle Mass

One of skill in the art would recognize the utility of the present invention given the information in the prior art and the teachings below. The results herein show that agonists of VPAC receptors induce skeletal muscle hypertrophy and/or inhibit skeletal muscle atrophy induced by denervation, disuse and corticosteroids, thus demonstrating the modulatory role and function of the VPAC receptors in the process of skeletal muscle atrophy. Not wishing to be bound by theory, it is thought that the effect of VPAC receptor agonists on skeletal muscle atrophy and hypertrophy is due to a direct effect on the muscle cells. However, it is also possible that this effect is mediated, in whole, or in part, through a secretagogue effect of the agonist on a non-muscle tissue.

The specific role of VPAC receptors in vivo was investigated using pharmacological agents, which are selective agonists for either PACAP receptors, the $VAPC_1$ receptor or the $VPAC_2$ receptor, in various models of skeletal muscle atrophy, described hereinafter. Selective agonists used include: PACAP-38 (non-selective for the $VAPC_1/VPAC_2/PAC1$ receptors) (Bachem Biosciences Inc., King of Prussia, Pa.); $[K^{15}, R^{16}, L^{27}, VIP(1-7), GRF(8-27)-NH_2]$ ($VPAC_1$ receptor selective agonist with potency similar to PACAP38) which was synthesized according to the method of Gourlet, Vertongen et al., Peptides 18 (1997) 403–408; and Ro 25-1553 ($VPAC_2$ receptor selective agonist with potency similar to PACAP38) which was purchased from Synpep Inc. (Dublin, Calif.). Before use, the agents were checked for purity by HPLC and for composition by mass spectrometry. These agents have been well characterized and are described in the scientific literature (Gourlet, Vandermeers et al., Peptides 18 (1997) 1539–1545; Gourlet, Vertongen et al., Peptides 18 (1997) 403–408; Gozes et al., Curr. Med. Chem. 6 (1999) 1019–1034).

FIGS. 1–5 show the results of experiments demonstrating that administration of agonists for $VPAC_1$ or $VPAC_2$ receptors result in statistically significant inhibition of skeletal muscle atrophy and or induction of hypertrophy. $VPAC_1$ or $VPAC_2$ receptor agonists administered twice daily in combination with theophylline resulted in inhibition of skeletal muscle atrophy in animal models of skeletal muscle atrophy. Theophylline was added to potentiate the duration and magnitude of action of the $VPAC_1$ and $VPAC_2$ receptor agonists therefore resulting in increased efficacy of these compounds. Theophylline administered by itself in these atrophy models had no effect, demonstrating that the anti-atrophy effect of the $VPAC_1$ and $VPAC_2$ receptor agonists in combination with theophylline was due to the effect of the VPAC receptor agonists. Furthermore, continuous dosing of the $VPAC_1$ and $VPAC_2$ receptor agonists in the absence of theophylline, via osmotic mini-pump, also resulted in inhibition of skeletal muscle atrophy and or in skeletal muscle hypertrophy.

Specifically, FIG. 1 (FIG. 1.) shows the results of a mouse denervation atrophy study utilizing the $VPAC_1$ receptor selective agonist, $[K^{15}, R^{16}, L^{27}VIP(1-7), GRF(8-27)-NH_2]$ (VPAC1R agonist), the $VPAC_2$ receptor selective agonist, Ro 25-1553 (VPAC2R agonist), or the $VPAC_1/VPAC_2$ receptor nonselective agonist, PACAP-38. Following denervation of the right sciatic nerve, male mice were injected subcutaneously in the midscapular region twice daily, with either the above indicated agents at the doses indicated in FIGS. 1A and 1B or vehicle control (physiological saline) for nine days. These agonists were co-administered with twice daily intra-peritoneal dosing of the phosphodiesterase inhibitor theophylline (T-30 mg/kg) (included to increase the magnitude and the duration of action of cAMP signals induced by the VPAC receptor agonists). On day nine, the medial gastrocnemius and tibialis anterior muscles were removed and weighed to determine the degree of atrophy. This experiment demonstrated that the non-specific VPAC receptor agonist, PACAP-38 inhibited atrophy of the denervated tibialis anterior (FIG. 1A) and medial gastrocnemius muscles (FIG. 1B). The $VPAC_1$ receptor selective agonist $[K^{15}, R^{16}, L^{27}VIP(1-7), GRF(8-27)-NH_2]$ inhibited atrophy of the denervated medial gastrocnemius muscle (FIG. 1B). The $VPAC_2$ receptor selective agonist Ro 25-1553 inhibited atrophy of the denervated tibialis anterior (FIG. 1A) and medial gastrocnemius (FIG. 1B) muscles. Statistical significance of the results were determined using ANCOVA (Douglas C. Montgomery, Design and Analysis of Experiments, John Wiley and Sons, New York ($2^{nd}$ ed. 1984)).

FIG. 2 (FIG. 2.) shows the results of a mouse denervation atrophy study utilizing the $VPAC_1$ receptor selective agonist, $[K^{15}, R^{16}, L^{27}VIP(1-7), GRF(8-27)-NH_2]$ ($VPAC_1R$ agonist), the $VPAC_2$ receptor selective agonist, Ro 25-1553 (VPAC2R agonist), or the $VPAC_1/VPAC_2$ receptor nonselective agonist, PACAP-38. Following denervation of the right sciatic nerve, male mice were dosed with the above indicated agents or vehicle control (physiological saline) by continuous infusion using an ALZeT osmotic minipump at 5 μl/hr until the end of the experimental period. The daily delivered dose of the agents are as indicated on FIGS. 2A and 2B. Minipump implantation was performed at the same time as the sciatic nerve denervation. On day nine the medial gastrocnemius and tibialis anterior muscles were removed and weighed to determine the degree of atrophy. The $VPAC_2$ receptor selective agonist Ro 25-1553 inhibited atrophy of the denervated tibialis anterior (FIG. 2A) muscle. In addition, the VPAC2 receptor selective agonist, Ro 25-1553, induced hypertrophy of the non-denervated (control) tibialis anterior (FIG. 2A) and medial gastrocnemius (FIG. 2B) muscles. Statistical significance of the results were determined using ANCOVA.

FIG. 3 (FIG. 3.) shows the results of a mouse glucocorticoid-induced atrophy study utilizing the $VPAC_1$ receptor selective agonist, [$K^{15}$, $R^{16}$, $L^{27}$VIP(1–7), GRF(8–27)-$NH_2$] (VPAC1R agonist), the $VPAC_2$ receptor selective agonist, Ro 25-1553 (VPAC2R agonist), or the $VPAC_1$/VPAC2 receptor nonselective agonist, PACAP-38. Following the addition of the glucocorticoid, dexamethasone to the drinking water (1.2 mg/kg/d), male mice were injected subcutaneously in the midscapular region twice daily, with either the above indicated agents at the doses indicated in FIGS. 3A and 3B or vehicle control (physiological saline) for nine days. These agonists were co-administered with twice daily intra-peritoneal dosing of the phosphodiesterase inhibitor theophylline (T—30 mg/kg). Nine days following the initiation of dosing of the VPAC receptor agonists and dexamethasone, the medial gastrocnemius and tibialis anterior muscles were removed and weighed to determine the degree of atrophy. This experiment demonstrates that the non-specific VPAC receptor agonist, PACAP-38, inhibits muscle atrophy of the medial gastrocnemius atrophy induced by glucocorticoid administration (FIG. 3B). The $VPAC_1$ receptor selective agonist [$K^{15,}$ $R^{16}$, $L^{27}$ VIP(1–7), GRF(8–27)-$NH_2$] inhibited muscle atrophy of the tibialis anterior induced by glucocorticoid administration (FIG. 3A). The $VPAC_2$ receptor selective agonist Ro 25-1553 inhibited muscle atrophy of the tibialis anterior (FIG. 3A) and medial gastrocnemius (FIG. 3B) induced by glucocorticoid administration. Statistical significance of the results were determined using ANCOVA.

FIG. 4 (FIG. 4.) shows the results of a mouse disuse (casting) atrophy study utilizing the $VPAC_2$ receptor selective agonist, Ro 25-1553 (VPAC2R agonist). Following casting of the right hind leg, male mice were injected subcutaneously in the midscapular region twice daily, with either the above indicated agent at the doses indicated in FIGS. 4A and 4B or vehicle control (physiological saline) for nine days. The VPAC2R agonist was co-administered with twice daily intra-peritoneal dosing of the phosphodiesterase inhibitor theophylline (T—30 mg/kg). On day nine, the medial gastrocnemius and tibialis anterior muscles were removed and weighed to determine the degree of atrophy. The $VPAC_2$ receptor selective agonist Ro 25-1553 inhibited disuse-induced atrophy of the tibialis anterior muscle (FIG. 4A). In addition, Ro251553 induced hypertrophy of the medial gastrocnemius muscle. Statistical significance of the results were determined using ANCOVA.

FIG. 5 (FIG. 5.) shows the results of a rat denervation atrophy study utilizing the $VPAC_2$ receptor selective agonist, Ro 25-1553 ($VPAC_2R$ receptor). Following denervation of the right sciatic nerve, male rats were injected subcutaneously in the midscapular region twice daily, with either the $VPAC_2R$ receptor agonist at the doses indicated in FIGS. 5A and 5B or vehicle control (physiological saline) for nine days. The $VPAC_2R$ receptor agonist was co-administered with twice daily intra-peritoneal dosing of the phosphodiesterase inhibitor theophylline (T—30 mg/kg). On day nine, the tibialis anterior and extensor digitorum longus (EDL) muscles were removed and weighed to determine the degree of atrophy. This experiment demonstrated that the $VPAC_2$ receptor selective agonist Ro 25-1553 inhibited atrophy of the denervated tibialis anterior (FIG. 5A) and EDL (FIG. 5B) muscles. Statistical significance of the results were determined using ANCOVA.

III. Preparation of VPAC Receptors, VIP or VIP Analogs, or Cell Lines Expressing VPAC Receptors $VPAC_1$ receptors, $VPAC_2$ receptors, VIP and VIP analogs can be prepared for a variety of uses, including, but not limited to, the generation of antibodies, use as reagents in the screening assays of the present invention, and use as pharmaceutical reagents for the treatment of skeletal muscle atrophy. It will be clear to one of skill in the art, that for certain embodiments of the invention, purified polypeptides will be most useful, while for other embodiments cell lines expressing the polypeptides will be most useful. For example, in situations where it is important to retain the structural and functional characteristics of the VPAC receptor, e.g. in a screening method to identify candidate compounds which activate VPAC receptors, it is desirable to use cells which express functional VPAC receptors.

Because VIP and VIP analogs are short polypeptides, the skilled artisan will recognize that these polypeptides will be most conveniently provided by direct synthesis, rather than by recombinant means, using techniques well known in the art. In addition, many of these molecules are commercially available.

Where the source of VPAC receptors is a cell line expressing the polypeptide, the cells may, for example, endogenously express VPAC receptor, have been stimulated to increase endogenous VPAC receptor expression or have been genetically engineered to express a VPAC receptor. Methods for determining whether a cell line expresses a polypeptide of interest are known in the art, for example, detection of the polypeptide with an appropriate antibody, use of a DNA probe to detect mRNA encoding the protein (e.g. northern blot or PCR techniques), or measuring binding of an agent selective for the polypeptide of interest (e.g. a radiolabeled selective agonist).

The use of recombinant DNA technology in the preparation of $VPAC_1$, $VPAC_2$, or of cell lines expressing these polypeptides is particularly contemplated. Such recombinant methods are well known in the art. To express recombinant $VPAC_1$ or $VPAC_2$ receptors, an expression vector that comprises a nucleic acid which encodes the polypeptide of interest under the control of one or more regulatory elements, is prepared. Genomic or cDNA sequences encoding $VPAC_1$ and $VPAC_2$ receptors from several species have been described and are readily available from the GenBank database (available at <http://www.ncbi.nlm.nih.gov/>). The accession numbers for $VPAC_1$ receptor sequences include: L13288 (human); U11079, U11080, U11081, U11082, U11083, U11084, U11085, U11086, U11087 which together make up the complete gene sequence for human $VPAC_1$ receptor (the assembled listing is under 806702); X75299 (human), M86835 (*Rattus norvegicus*); NM_011703 (*Mus musculus*), U49434 (*Sus scrofa*), AF100644 (*Rana ridibunda*), I28734 (Porcine), E05551 (Rattus sp.) and U56391 (*Carassius auratus*). The accession numbers for $VPAC_2$ receptor sequences include: X95097 (human), L40764 (human), L36566 (human), Y18423 (human), U18810 (human), D28132 (*Mus musculus*), Z25885 (*Rattus norvegicus*), U09631 (*Rattus norvegicus*), and A43808 (Rat). Using this publicly available sequence information, one means of isolating a nucleic acid molecule encoding a $VPAC_1$ or $VPAC_2$ receptor is to screen a genomic DNA or cDNA library with a natural or artificially synthesized DNA probe, using methods well known in the art, e.g. by PCR amplification of the sequence from an appropriate library. Another method is to use oligonucleotide primers specific for the receptor of interest to PCR amplify the cDNA directly from mRNA isolated from a particular tissue (such as skeletal muscle). Such isolated mRNA is commercially available. One of skill in the art would also recognize that by using nucleic acid probes corresponding to portions of the known VPAC receptor sequences the homologous cDNAs or genomic sequences from other species can be obtained using known methods. Particularly useful in the methods of the present invention are VPAC receptors from the species including, but not limited to, human, mouse, rat, pig, monkey, chimpanzee, marmoset, dog, cow, sheep, cat, chicken and turkey. By methods well known in the art, the isolated nucleic acid molecule encoding the VPAC receptor of interest is then ligated into a suitable expression vector. The expression vector, thus prepared, is expressed in a host cell and the host cells expressing the receptor are used directly in a screening assay or the receptor is isolated from the host cells expressing the receptor and the isolated receptor is used in a screening assay.

The host-expression vector systems that may be used for purposes of the invention include, but are not limited to: microorganisms such as bacteria (e.g., E. coli, B. subtilis) transformed with recombinant bacteriophage DNA, plasmid DNA, or cosmid DNA expression vectors containing VPAC receptor nucleotide sequences; yeast (e.g., Saccharomyces, Pichia) transformed with recombinant yeast expression vectors containing VPAC receptor nucleotide sequences; insect cell systems infected with recombinant virus expression vectors (e.g., baculovirus) containing VPAC receptor nucleotide sequences; plant cell systems infected with recombinant virus expression vectors (e.g., cauliflower mosaic virus, tobacco mosaic virus) or transformed wvith recombinant plasmid expression vectors (e.g., Ti plasmid) containing VPAC receptor nucleotide sequences; or mammalian cell systems (e.g., COS, CHO, HEK293, NIH3T3) harboring recombinant expression constructs containing promoters derived from the genome of mammalian cells (e.g., metallothionein promoter) or from mammalian viruses (e.g. retrovirus LTR) and also containing VPAC receptor nucleotide sequences.

The host cell is used to produce the polypeptide of interest. Because the VPAC receptor is a membrane bound molecule, it is purified from the host cell membranes or the VPAC receptor is utilized while anchored in the cell membrane, i.e. whole cells or membrane fractions of cells are used. Purification or enrichment of the VPAC receptors from such expression systems is accomplished using appropriate detergents and lipid micelles by methods well known to those skilled in the art.

In bacterial systems, a number of expression vectors may be advantageously selected depending upon the use intended for the gene product being expressed. For example, when a large quantity of such proteins is produced for the generation of antibodies to VPAC receptors, vectors which direct the expression of high levels of protein products, are desirable. One skilled in the art is able to generate such vector constructs and purify the proteins by a variety of methodologies including selective purification technologies such as fusion protein selective columns and antibody columns, and non-selective purification technologies.

In an insect protein expression system, the baculovirus A. californica nuclear polyhedrosis virus (AcNPV), is used as a vector to express foreign genes in S. frugiperda cells. In this case, VPAC receptor nucleotide sequences are cloned into non-essential regions of the virus and placed under the control of an AcNPV promoter. The recombinant viruses are then used to infect cells in which the inserted gene is expressed and the protein is purified by one of many techniques known to one skilled in the art.

In mammalian host cells, a number of viral-based expression systems may be utilized. Utilization of these expression systems often requires the creation of specific initiation signals in the vectors for efficient translation of the inserted nucleotide sequences. This is particularly important if a portion of the VPAC receptor gene is used which does not contain the endogenous initiation signal. The placement of this initiation signal, in frame with the coding region of the inserted nucleotide sequence, as well as the addition of transcription and translation enhancing elements and the purification of the recombinant protein are achieved by one of many methodologies known to one skilled in the art. Also important in mammalian host cells is the selection of an appropriate cell type which is capable of the necessary post translational modifications of the recombinant protein. Such modifications, for example, cleavage, phosphorylation, glycosylation, etc., require the selection of the appropriate host cell which contains the modifying enzymes. Such host cells include, but are not limited to, CHO, HEK293, NIH3T3, COS, etc. and are known by those skilled in the art.

For long term, high expression of recombinant proteins, stable expression is preferred. For example, cell lines which stably express VPAC receptors may be engineered. One of skill in the art, following known methods such as electroporation, calcium phosphate transfection, or liposome mediated transfection, can generate a cell line which stably expresses VPAC receptors. This is usually accomplished by transfecting cells using expression vectors which contain appropriate expression control elements (e.g., promoter sequences, enhancer sequences, transcriptional termination sequences, polyadenylation sites, translational start sites, etc.), a selectable marker, and the gene of interest. The selectable marker may either be contained within the same vector, as the gene of interest, or on a separate vector which is co-transfected with the VPAC sequence containing vector. The selectable marker in the expression vector may confer resistance to the selection and allows cells to stably integrate the vector into their chromosomes and to grow to form foci which in turn can be cloned and expanded into cell lines. Alternatively the expression vector may allow selection of the cell expressing the selectable marker utilizing a physical attribute of the marker, i.e. expression of Green Fluorescent Protein (GFP) allows for selection of cells expressing the marker using fluorescence activated cell sorting (FACS) analysis.

One of skill in the art is able to select an appropriate cell type for transfection in order to allow for selection of cells into which the gene of interest has been successfully integrated. For example, where the selectable marker is herpes simplex virus thymidine kinase, hypoxanthine-guanine phosphoribosyltransferase or adenine phosphoribosyltransferase, the appropriate cell type would be tk-, hgprt- or aprt-cells, respectively. Or, wild type cells can be used where the selectable marker is dhfr, gpt, neo or hygro which confer resistance to methotrexate, mycophenolic acid, G-418 or hygromycin, respectively. Such recombinant cell lines are useful for identification of candidate compounds that affect the VPAC receptor activity.

IV Preparation of VPAC Receptor Antibodies

Antibodies that selectively recognize one or more epitopes of a VPAC receptor are also encompassed by the invention. Such antibodies include, e.g., polyclonal antibodies, monoclonal antibodies, chimeric antibodies, human antibodies, single chain antibodies, Fab fragments, F(ab')$_2$ fragments, molecules produced using a Fab expression library, human antibodies (polyclonal or monoclonal) produced in transgenic mice and epitope binding fragments of any of the above. For therapeutic uses, chimeric or human antibodies are preferred; human antibodies are most preferred.

The antibodies can be utilized in conjunction with the compound screening schemes described herein for the evaluation of test compounds, e.g. for immobilization of VPAC receptor polypeptides or such antibodies can be used in conjunction with gene therapy techniques to evaluate, for example, the expression of VPAC receptors either in cells or directly in patient tissues in which these genes have been introduced. In addition, antibodies of the present invention are useful in the treatment of skeletal muscle atrophy. Antibodies selective for the VPAC receptor can be screened by the methods of the present invention to identify a subset of the antibodies which are VPAC receptor agonists. In addition, anti-idiotype antibodies generated against antibodies specific for VIP or a VIP analog may be useful as VPAC receptor agonists and like anti-VPAC antibodies may be screened for their ability to activate the VPAC receptor by methods of the present invention.

For the production of antibodies, a variety of host animals may be immunized by injection with VPAC, VIP or a VIP analog, anti-VIP antibody, anti-VIP analog antibody, or immunogenic fragments thereof by methods well known in the art. For preparation of an anti-idiotype antibody the immunogen is an anti-VIP antibody or anti-VIP analog antibody. Production of anti-idiotype antibodies is described, for example, in U.S. Pat. No. 4,699,880, incorporated herein by reference. Suitable host animals include, but are not limited to, rabbits, mice, goats, sheep and horses. Immunization techniques are well known in the art. Polyclonal antibodies can be purified from the serum of the immunized animals, or monoclonal antibodies can be generated by methods which are well known in the art. These techniques include, but are not limited to, the well-known hybridoma techniques of Kohler and Milstein, human B-cell hybridoma techniques, and the EBV hybridoma technology. Monoclonal antibodies may be of any immunoglobulin class, including IgG, IgE, IgM, IgA, and IgD containing either kappa or lambda light chains.

Because of the immunogenicity of non-human antibodies in humans, chimeric antibodies are preferred to non-human antibodies when used for therapeutic treatment of human patients. Techniques of producing and using chimeric antibodies are known in the art, and are described in, for example, Vaswani et al., *Ann. Allergy Asthma Immunol.,* 1998;81:105–119, Farah et al., *Critical Reviews in Eukaryotic Gene Expression,* 1998;8(3–4):321–56, U.S. Pat. Nos. 5,807,715; 4,816,397; 4,816,567; and 5,824,307, all incorporated herein by reference.

Completely human antibodies are particularly desirable for therapeutic treatment of human patients because they are less immunogenic than non-human antibodies. Such antibodies can be produced using transgenic mice which are substantially incapable of expressing endogenous immunoglobulin heavy and light chain genes, but which can express human heavy and light chain genes. The transgenic mice are immunized in the normal fashion with a selected antigen, e.g., all or a portion of VPAC. Monoclonal antibodies directed against the antigen are obtained using conventional hybridoma technology from these immunized transgenic mice. This technology is described in detail in U.S. Pat. Nos. 5,874,299; 5,877,397; 5,569,825; 5,661,016; 5,770,429; and 6,075,181, all incorporated herein by reference. As an alternative to obtaining human immunoglobulins directly from the culture of the hybridoma cells, the hybridoma cells can be used as a source of rearranged heavy chain and light chain loci for subsequent expression or genetic manipulation. Isolation of genes from such antibody-producing cells is straightforward since high levels of the appropriate mRNAs are available. The recovered rearranged loci can be manipulated as desired. For example, the constant region can be eliminated or exchanged for that of a different isotype or the variable regions can be linked to encode single chain Fv regions. Such techniques are described in WO 96/33735 and WO 96/34096, all incorporated herein by reference.

V. Selection of Test Compounds

Compounds that can be screened in accordance with the assays of the invention include but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular library made of D- or L-configuration amino acids, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')$_2$ and Fab expression library fragments, and epitope-binding fragments thereof), organic and inorganic molecules.

In addition to the more traditional sources of test compounds, computer modeling and searching technologies permit the rational selection of test compounds by utilizing structural information from the ligand binding site of VPAC or from already identified agonists of VPAC receptors. Such rational selection of test compounds can decrease the number of test compounds that must be screened in order to identify a candidate therapeutic compound. VPAC receptors are GPCRs and thus knowledge of the VPAC protein sequence allows for the generation of a model of the binding site that can be used to screen for potential ligands. This process can be accomplished in several manners. The most robust approach involves generating a sequence alignment of the VPAC receptor sequence to a template (derived from the bacterio-rhodopsin or rhodopsin crystal structures or other GPCR model), conversion of the amino acid structures and refining the model by molecular mechanics and visual examination. If a strong sequence alignment cannot be obtained then a model may also be generated by building models of the hydrophobic helices. These are then fitted together by rotating and translating each helix relative to the others starting from the general layout of the known rhodopsin structures. Mutational data that points towards residue-residue contacts may also be used to position the helices relative to each other so that these contacts are achieved. During this process, docking of the known ligands into the binding site cavity within the helices may also be used to help position the helices by developing interactions that would stabilize the binding of the ligand. The model may be completed by refinement using molecular mechanics and loop building of the intracellular and extracellular loops using standard homology modeling techniques. General information regarding GPCR structure and modeling can be found in Schoneberg, T. et. al., *Molecular and Cellular Endocrinology,* 151 (1999), 181–193, Flower, D., *Biochimica et Biophysica Acta,* 1422 (1999), 207–234, and Sexton, P. M., *Current Opinion in Drug Discovery and Development,* 2(5), 1999, 440–448, incorporated herein by reference.

Once the model is completed, it can be used for screening for potential ligands for example by using one of several existing computer programs. The most general of these is the DOCK program (UCSF Molecular Design Institute, 533 Parnassus Ave, U64, Box 0446, San Francisco, Calif. 94143-0446). In several of its variants it can screen databases of commercial and/or proprietary compounds for steric fit and rough electrostatic complementarity to the binding site. It has frequently been found that molecules that score well within DOCK have a better chance of being ligands. Another program that can be used is FLEXX (Tripos Inc., 1699 South Hanley Rd., St. Louis, Mo., 6314-42913 <www.tripos.com>). This program, being significantly slower, is usually restricted to searches through smaller databases of compounds. The scoring scheme within FLEXX is more detailed and usually gives a better estimate of binding ability than does DOCK. FLEXX is best used to confirm DOCK suggestions, or to examine libraries of compounds that are generated combinatorially from known ligands or templates.

VI. Screening Assays to Identify Candidate Compounds for the Regulation of Skeletal Muscle Mass or Function The finding that VPAC receptors play a role in regulating skeletal muscle atrophy, enables various methods of screening one or more test compounds to identify candidate compounds that ultimately may be used for prophylactic or therapeutic treatment of skeletal muscle atrophy. This invention provides methods for screening test compounds for their ability to bind to VPAC receptors, activate VPAC receptors, prolong or augment the agonist-induced activation of VPAC receptors or of a VPAC receptor signal transduction pathway, increase expression of VPAC receptor genes, or increase expression of VIP or a VIP analog gene.

For screening for compounds which ultimately will be used to regulate skeletal muscle mass or function through $VPAC_1$ receptors in humans, it is preferred that the initial in vitro screen be carried out using a $VPAC_1$ receptor with an amino acid sequence that is greater than 60% identical to the sequence of the human $VPAC_1$ receptor, Accession No. L13288, (SEQ ID NO:1). More preferably the sequence of the $VPAC_1$ receptor is greater than 70% identical to SEQ ID NO:1, more preferably greater than 80% identical to SEQ ID NO:1 and more preferably greater than 90% identical to SEQ ID NO:1. Most preferably the test compounds will be screened against a human $VPAC_1$ receptor. For screening for compounds which ultimately will be used to regulate skeletal muscle mass or function through $VPAC_1$ in a non-human species, it is preferable to use the $VPAC_1$ receptor from the species in which treatment is contemplated.

For screening for compounds which ultimately will be used to regulate skeletal muscle mass or function through $VPAC_2$ receptors in humans, it is preferred that the initial in vitro screen be carried out using a $VPAC_2$ receptor with an amino acid sequence that is greater than 60% identical to the sequence of the human $VPAC_2$ receptor, Accession No. X95097, (SEQ ID NO:10). More preferably the sequence of the $VPAC_2$ receptor is greater than 70% identical to SEQ ID NO:10, more preferably greater than 80% identical to SEQ ID NO:10 and more preferably greater than 90% identical to SEQ ID NO:10. Most preferably the test compounds will be screened against a human $VPAC_2$ receptor. For screening for compounds which ultimately will be used to regulate skeletal muscle mass or function through $VPAC_2$ receptors in a non-human species, it is preferable to use the $VPAC_2$ receptor from the species in which treatment is contemplated.

The methods of the present invention are amenable to high throughput applications, however, the use of as few as one test compound in the method is encompassed by the term screening. Test compounds which activate VPAC receptors, prolong or augment the agonist-induced activation of VPAC receptors or of a VPAC receptor signal transduction pathway, increase expression of VPAC receptor genes, or increase expression of VIP or a VIP analog gene, as determined by a method of the present invention are referred to herein as "candidate compounds". Such candidate compounds can be used to regulate skeletal muscle mass or function. However, more typically, this first level of in vitro screen provides a means by which to select a narrower range of compounds, i.e., the candidate compounds, which merit further investigation in additional levels of screening. The skilled artisan will recognize that a utility of the present invention is to identify, from a group of one or more test compounds, a subset of compounds which merit further investigation. One of skill in the art will also recognize that the assays of the present invention are useful in ranking the probable usefulness of a particular candidate compound relative to other candidate compounds. For instance, a candidate compound which activates VPAC at 1000 nM (but not at 10 nM) is of less interest than one which activates VPAC at 10 nM. Using such information the skilled artisan may select a subset of the candidate compounds, identified in the first level of screening, for further investigation. By the way of example only, compounds which activate VPAC at concentrations of less than 200 nM might be further tested in an animal model of skeletal muscle atrophy, whereas those above that threshold would not be further tested. The skilled artisan will also recognize that depending on how the group of test compounds is selected, and how the positives are selected, only a certain proportion of test compounds will be identified as candidate compounds, and that this proportion may be very small.

The assay systems described below may be formulated into kits comprising VPAC receptors or cells expressing the VPAC receptors which can be packaged in a variety of containers, e.g., vials, tubes microtitre well plates, bottles and the like. Other reagents can be included in separate containers and provided with the kit, e.g., positive control samples, negative control samples, buffers and cell culture media.

In one embodiment, the invention provides a method for screening one or more test compounds to identify candidate compounds that bind to VPAC receptors. Methods of determining binding of a compound to a receptor are well known in the art. Typically, the assays include the steps of incubating a source of the VPAC receptor with a labeled compound, known to bind to the receptor, in the presence or absence of a test compound and determining the amount of bound labeled compound. The source of VPAC receptor may either be cells expressing VPAC receptors or some form of isolated VPAC receptor, as described herein. The labeled compound can be VIP or any VIP analog labeled such that it can be measured, preferably quantitatively (e.g., $^{125}I$-labeled, europium labeled, fluorescein labeled, GFP labeled, $^{35}S$-methionine labeled). Such methods of labeling are well known in the art. Test compounds that bind to the VPAC receptor cause a reduction in the amount of labeled ligand bound to the receptor, thereby reducing the signal level compared to that from control samples (absence of test compound). Variations of this technique have been described in which receptor binding in the presence and absence of G-protein uncoupling agents can discriminate agonists from antagonists (e.g. binding in the absence and presence of a guanine nucleotide analog i.e: GpppNHp). See Keen, M., *Radioligand Binding Methods for Membrane Preparations and Intact cells* in *Receptor Signal Transduction Protocols*, R. A. J. Challis, (ed), Humana Press Inc., Totoway N.J. (1997).

When it is desired to discriminate between compounds which bind specifically to $VPAC_1$ or $VPAC_2$ (i.e. to one receptor type but not the other) the assays described above should be conducted using a cell, or membrane from a cell, which expresses only one of the VPAC receptors, or the assays can be conducted with a recombinant source of a particular receptor. Cells expressing more than one form of VPAC may be modified using homologous recombination to inactivate or otherwise disable the VPAC receptor gene that is not of interest. Alternatively, if the source of VPAC contains more than one VPAC receptor type, the background signal produced by the receptor which is not of interest must be subtracted from the signal obtained in the assay. The background response can be determined by a number of methods, including elimination of the signal from the VPAC receptor which is not of interest by use of antisense, antibodies or selective antagonists.

In another embodiment, the invention provides methods for screening test compounds to identify candidate compounds which activate VPAC receptors. Typically, the assays are cell-based however, cell-free assays are known which are able to differentiate agonist and antagonist binding as described above. Cell-based assays include the steps of contacting cells which express the $VPAC_1$ or $VPAC_2$ receptor with a test compound or control and measuring activation of the VPAC receptor by measuring the expression or activity of components of the VPAC receptor signal transduction pathways.

As described in the background section above, VPAC receptors appear to couple through several different pathways including $G_{\alpha s}$, $G_{\alpha q}$, or $G_{\alpha i}$, depending upon the cell type. It is thought that agonist activation of VPAC allows the receptor to signal via any of these pathways, provided that the necessary pathway components are present in the particular cell type. Thus, to screen for VPAC activation, an assay can use any of the signal transduction pathways as the readout even if the relevant cell type for treatment, in vivo, couples VPAC to skeletal muscle atrophy via a different pathway. One of ordinary skill in the art would recognize that a screening assay would be effective for identifying useful VPAC agonists independent of the pathway by which receptor activation was measured. Assays for measuring activation of these signaling pathways are known in the art.

For example, after contact with the test compound, lysates of the cells can be prepared and assayed for induction of cAMP. cAMP is induced in response to $G_{\alpha s}$ activation. Because $G_{\alpha s}$ is activated by receptors other than VPAC and because a test compound may be exerting its effect through VPAC receptors or by another mechanism, two control comparisons are relevant for determining whether a text compound increases levels of cAMP via activation of a VPAC receptor. One control compares the cAMP level of cells contacted with a test compound and the cAMP level of cells contacted with a control compound (i.e. the vehicle in which the test compound is dissolved). If the test compound increases cAMP levels relative to the control compound this indicates that the test compound is increasing cAMP by some mechanism. The other control compares the cAMP levels of a VPAC expressing cell line and a cell line, that is essentially the same except that it does not express the VPAC receptor where both of the cell lines have been treated with test compound. If the test compound elevates cAMP levels in the VPAC receptor expressing cell line relative to the cell line that does not express VPAC receptors, this is an indication that the test compound elevates cAMP via activation of the VPAC receptors.

In a specific embodiment of the invention, constructs containing the cAMP responsive element linked to any of a variety of reporter genes can be introduced into cells expressing VPAC receptors. Such reporter genes include, but are not limited to, chloramphenicol acetyltransferase (CAT), luciferase, glucuronide synthetase, growth hormone, fluorescent proteins (e.g., Green Fluorescent Protein), or alkaline phosphatase. Following exposure of the cells to the test compound, the level of reporter gene expression can be quantitated to determine the test compound's ability to activate the VPAC receptor.

The cells useful in this assay are the same as for the VPAC receptor binding assay described above, except that cells utilized in the activation assays preferably express a functional receptor which gives a statistically significant response to VIP or one or more VIP analog. In addition to using cells expressing full length VPAC receptors, cells can be engineered which express VPAC receptors containing the ligand binding domain of the receptor coupled to, or physically modified to contain, reporter elements or to interact with signaling proteins. For example, a wild-type VPAC or VPAC fragment can be fused to a G-protein resulting in activation of the fused G-protein upon agonist binding to the VPAC portion of the fusion protein. Siefert, R. et al., *Trends Pharmacol. Sci.*, 1999; 20: 383–389. The cells should also preferably possess a number of characteristics, depending on the readout, to maximize the inductive response by VIP or the VIP analog, for example, for detecting a strong induction of a CRE reporter gene; (a) a low natural level of cAMP; (b) G proteins capable of interacting with VPAC receptors; (c) a high level of adenylyl cyclase; (d) a high level of protein kinase A; (e) a low level of phosphodiesterases; and (f) a high level of cAMP response element binding protein would be advantageous. To increase the response to VIP or a VIP analog, host cells could be engineered to express a greater amount of favorable factors or a lesser amount of unfavorable factors. In addition, alternative pathways for induction of the CRE reporter could be eliminated to reduce basal levels.

In some instances, G protein-coupled receptor responses subside, or become desensitized, after prolonged exposure to an agonist. Another embodiment of the invention provides methods for identifying compounds that prolong or augment the agonist-induced activation of VPAC receptors, or the VPAC receptor signal transduction pathway, in response to a VPAC receptor agonist. Such compounds may be used, for example, either alone or in conjunction with a VPAC receptor agonist, for the treatment of skeletal muscle atrophy. Typically the method uses a cell based assay comprising (i) treating cells expressing functional VPAC receptors with a VPAC receptor agonist at a concentration of agonist and for a period of agonist-receptor exposure sufficient to allow desensitization of the receptor, (ii) contacting the cells with a test compound and (iii) determining the level of activation of the VPAC receptor. One of skill in the art will recognize that several mechanisms contribute to receptor desensitization including, but not limited to, receptor phosphorylation, receptor internalization or degradation and VPAC receptor signal transduction pathway down-modulation. One of skill in the art can determine the appropriate time (i.e. before, during or after agonist treatment) for contacting the cells with the test compounds depending upon which mechanism of desensitization is targeted. For example, contacting the cells with test compounds following agonist treatment, can detect test compounds which block receptor desensitization which occurs as a result of phosphorylation of the receptor.

In another embodiment, the invention provides a method of screening one or more test compound to identify candidate compounds which regulate transcription of VPAC genes or VPAC receptor expression. Candidate compounds which regulate transcriptional activity of VPAC genes may be identified using a reporter gene operably associated with a VPAC receptor regulatory region (reporter gene construct). Such methods are known in the art. In one such method, the reporter gene construct is contacted with a test compound in the presence of a source of cellular factors and the level of reporter gene expression is determined. A test compound which causes an increase in the level of expression, compared to a control sample, is indicative of a candidate compound which increases transcription of the VPAC gene. To provide the cellular factors required for in vitro or in vivo transcription, appropriate cells or cell extracts are prepared from any cell type that normally expresses VPAC receptors.

Candidate compounds which regulate VPAC receptor expression can also be identified in a method wherein a cell is contacted with a test compound and the expression of VPAC is determined. The level of expression of VPAC receptor in the presence of the test compound is compared with the level of expression in the absence of the test compound. Test compounds which increase the expression of VPAC are identified as candidate compounds for increasing muscle mass or muscle function. Such a method detects candidate compounds which increase the transcription or translation of the VPAC receptor or which increase the stability of the mRNA or VPAC receptors.

In another embodiment, this invention provides methods for screening one or more test compounds to identify candidate compounds which regulate the expression of the VIP or a VIP analog. Such assays are performed essentially as described above for the assays to identify candidate compounds which regulate expression of VPAC receptors with the following modifications. To identify candidate compound which regulate transcription from the VIP gene or a VIP analog gene, the reporter gene is operably associated with the regulatory region of the VIP gene or VIP analog gene of interest and the source of cellular factors should be from a cell type that expresses the gene of interest.

VII. Screening of Candidate Compounds using Models of Skeletal Muscle Atrophy

Candidate compounds selected from one or more test compounds by an in vitro assay, as described above, can be further tested for their ability to regulate skeletal muscle mass or function in model systems of skeletal muscle atrophy and/or hypertrophy. Such models of skeletal muscle atrophy or hypertrophy include both in vitro cell culture models and in vivo animal models of skeletal muscle atrophy. Such additional levels of screening are useful to further narrow the range of candidate compounds that merit additional investigation, e.g. clinical trials.

Cell Culture Models of Muscle Atrophy

In vitro models of skeletal muscle atrophy are known in the art. Such models are described, for example, in ; Vandenburgh, H. H., In Vitro 24: 609–619, 1988; Vandenburgh, H. H. et al., *J of Biomechanics*, 24 Suppl 1: 91–9, 1991; Vandenburgh, H. H et al., *In Vitro Cell. Dev. Biol.,* 24(3): 166–74, 1988; Chromiak, J. A., et al., *In Vitro Cell. Dev. Biol. Anim.,* 34(9): 694–703, 1998; Shansky, J., et al., *In Vitro Cell. Dev. Biol. Anim.,* 33(9): 659–61, 1997; Perrone, C. E. et al., *J. Biol. Chem.* 270(5): 2099–106, 1995; Chromiac, J. A. and Vandenburgh, H. H., *J. Cell. Physiol.* 159(3): 407–14, 1994; and Vandenburgh, H. H. and Karlisch, P., *In Vitro Cell. Dev. Biol.,* 25(7): 607–16, 1989. Such models are useful, but not required, following the in vitro screening described above in order to further narrow the range of candidate compounds that merit testing in an animal model. Cell culture models are treated with candidate compounds and the response of the model to the treatment is measured by assessing changes in muscle markers such as: muscle protein synthesis or degradation, changes in skeletal muscle mass or contractile function. Those compounds which induce significant changes in the muscle markers are typically screened further in an animal model of skeletal muscle atrophy.

Animal Models of Skeletal Muscle Atrophy

The candidate compounds are administered to non-human animals and the response of the animals is monitored, for example, by assessing changes in markers of atrophy or hypertrophy such as: skeletal muscle mass, skeletal muscle function, muscle or myofiber cross-sectional area, contractile protein content, non-contractile protein content or a biochemical or genetic marker that correlates with skeletal muscle mass or function changes. Candidate compounds which induce skeletal muscle hypertrophy or prevent any aspect of skeletal muscle atrophy should be considered as prospective therapeutic candidates for treatment of human skeletal muscle atrophy, and are referred to herein as candidate therapeutic compounds. In addition to assessing the ability of a candidate compound to regulate skeletal muscle atrophy, undesirable side effects such as toxicity may also be detected in such a screen. The absence of unacceptably high levels of side effects may be used as a further criterion for the selection of candidate therapeutic compounds.

A variety of animal models for skeletal muscle atrophy are known in the art, such as those described in the following references: Herbison, G. J., et al. (1979) *Arch. Phys. Med. Rehabil.* 60:401–404, Appell, H-J. (1990) *Sports Medicine* 10:42–58, Hasselgren, P-O. and Fischer, J. E. (1998) *World J. Surg.* 22:203–208, Agbenyega, E. T. and Wareham, A. C. (1992) *Comp. Biochem. Physiol.* 102A:141–145, Thomason, D. B. and Booth, F. W. (1990) *J. Appl. Physiol.* 68:1–12, Fitts, R. H., et al. (1986) *J. Appl. Physiol.* 60:1946–1953, Bramanti, P., et al. (1998) *Int. J. Anat. Embryol.* 103:45–64, Cartee, G. D. (1995) *J. Gerontol. A Biol. Sci. Med. Sci.* 50:137–141, Cork, L. C., et al. (1987) *Prog. Clin. Biol. Res.* 229:241–269, Booth, F. W. and Goltnick, P. D. (1983) *Med. Sci. Sports Exerc.* 15:415–420, Bloomfield, S. A. (1997)*Med. Sci. Sports Exerc.* 29:197–206. Preferred animals for these models are mice and rats. These models include, for example, models of disuse-induced atrophy such as casting or otherwise immobilizing limbs, hind limb suspension, complete animal immobilization, and reduced gravity situations. Models of nerve damage induced atrophy include, for example, nerve crush, removal of sections of nerves which innervate specific muscles, toxin application to nerves and infection of nerves with viral, bacterial or eukaryotic infectious agents. Models of glucocorticoid-induced atrophy include application of atrophy-inducing doses of exogenous glucocorticoid to animals, and stimulation of endogenous corticosteroid production, for example, by application of hormones which activate the hypothalamus-pituitary-adrenal (HPA) axis. Models of sepsis-induced atrophy include, for example, inoculation with sepsis-inducing organisms such as bacteria, treatment of the animal with immune-activating compounds such as bacterial cell wall extract or endotoxin, and puncture of intestinal walls. Models of cachexia-induced atrophy include, for example, inoculation of an animal with tumorigenic cells with cachexia forming potential, infection of an animal with infectious agents (such as viruses which cause AIDS) which result in cachexia and treatment of an animal with hormones or cytokines such as CNTF, TNF, IL6, IL-1, etc. which induce cachexia. Models of heart failure-induced atrophy include the manipulation of an animal so that heart failure occurs with concomitant skeletal muscle atrophy. Neurodegenerative disease-induced atrophy models include autoimnuune animal models such as those resulting from immunization of an animal with neuronal components. Muscular dystrophy-induced models of atrophy include natural or man-made genetically-induced models of muscular dystrophy such as the mutation of the dystrophin gene which occurs in the Mdx mouse.

Animal models of skeletal muscle hypertrophy include, for example, models of increased limb muscle use due to inactivation of the opposing limb, reweighting following a disuse atrophy inducing event, reutilization of a muscle which atrophied because of transient nerve damage, increased use of selective muscles due to inactivation of a synergistic muscle (e.g. compensatory hypertrophy), increased muscle utilization due to increased load placed on the muscle and hypertrophy resulting from removal of the glucocorticoid after glucocorticoid-induced atrophy. Preferred animal atrophy models include the sciatic nerve denervation atrophy model, glucocorticoid-induced atrophy model, and the leg casting disuse atrophy model which are described in further detail below.

The sciatic nerve denervation atrophy model involves anesthetizing the animal followed by the surgical removal of a short segment of either the right or left sciatic nerve, e.g. in mice the sciatic nerve is isolated approximately at the midpoint along the femur and a 3–5 mm segment is removed. This denervates the lower hind limb musculature resulting in atrophy of these muscles. Typically, innervation to the biceps femoris is left intact to provide satisfactory motion of the knee for virtually normal ambulation. Typically, in untreated animals, muscle mass of the denervated muscles is reduced 30–50% ten days following denervation. Following denervation, test compounds are administered e.g., by injection or by continuous infusion, e.g. via implantation of an osmotic minipump (e.g. Alza, Palo Alto, Calif.), to determine their effect on denervation induced skeletal muscle atrophy. At various times following denervation, the animals are euthanized and lower leg muscles are dissected rapidly from both the denervated and nondenervated legs, the muscles, cleaned of tendons and connective tissue, are weighed. The extent of atrophy in the affected muscles is analyzed, for example, by measuring muscle mass, muscle cross-sectional area, myofiber cross-sectional area or contractile protein content.

The glucocorticoid induced atrophy model involves the administration of a glucocorticoid to the test animal, e.g. 1.2 mg/kg/day of dexamethasone in the drinking water. Typically, in untreated animals, skeletal muscle mass is reduced 30–50% following ten days of dexamethasone administration. Concomitantly with, or following glucocorticoid administration, test compounds are administered e.g., by injection or by continuous infusion to determine their effect on glucocorticoid induced skeletal muscle atrophy. At various times following glucocorticoid administration, the extent of atrophy in the affected muscles is analyzed as described above for the denervation model.

The leg casting disuse atrophy model involves casting one hind leg of an animal from the knee down through the foot. Typically, muscle mass is reduced 20–40% after ten days of casting. Following casting, test compounds are administered by injection or by continuous infusion via implantation of an osmotic minipump (e.g. Alza, Palo Alto, Calif.) to determine their effect on leg casting induced skeletal muscle atrophy. At various times following leg casting, the extent of atrophy in the affected muscles is analyzed as described above for the denervation model.

One of skill in the art would recognize that in screening for compounds for human use, because there are differences between the human VPAC receptor and the VPAC receptor from other animal species, there may be some false positive or negative results which arise when the screen is carried out using non-human VPAC receptor. Thus, it is preferable to do the initial in vitro screen using human VPAC receptors. In certain circumstances, identified candidate compounds may be active toward only the human receptor and not toward a non-human receptor. In such circumstances, it may still be desirable to determine whether these candidate compounds are able to regulate skeletal muscle mass or function in a second level of screening. Because these candidates do not activate non-human VPAC, a standard in vivo screen with non-human animal is not advised. In such circumstances, the second level of screening for these candidates may be performed in transgenic animals that express human VPAC receptors.

Animals of any species, including, but not limited to, mice, rats, rabbits, guinea pigs, pigs, goats, dogs and non-human primates may be used to generate VPAC receptor transgenic animals. Mice and rats are preferred, mice are most preferred. A variety of techniques are known in the art and may be used to introduce the human VPAC transgenes into animals to produce the founder lines of transgenic animals. Such techniques include, but are not limited to, pronuclear microinjection, retrovirus-mediated gene transfer into germ lines, gene targeting in embryonic stem cells, electroporation of embryos and sperm-mediated gene transfer.

VIII. Gene Therapy Methods for the Treatment of Skeletal Muscle Atrophy

The expression of VPAC, VIP and VIP analogs can be controlled in vivo using gene therapy approaches. VPAC, VIP and VIP analog gene expression and/or activity can be increased by introducing a VPAC receptor, a constitutively active VPAC, VIP or VIP analog gene, into the appropriate tissue. Overexpression of these genes will increase the total cellular VPAC activity, thus, regulating skeletal muscle atrophy. The gene or genes of interest are inserted into a vector suitable for expression in the subject. These vectors include, but are not limited to, adenovirus, adenovirus associated virus, retrovirus and herpes virus vectors in addition to other particles that introduced DNA into cells (e.g. liposome, gold particles, etc.) or by direct injection of the DNA expression vector, containing the gene of interest, into human tissue (e.g. muscle).

Additional methods which may be utilized to increase the overall level of VIP or VIP analog gene expression include the introduction of VIP or VIP analog-expressing cells, preferably autologous cells, into the patient. These cells may be either recombinant (e.g. engineered to express VIP or VIP analogs) or non-recombinant (e.g. cells which endogenously express VIP or VIP analogs). The cells can be delivered to multiple sites in the body (e.g. muscle) for treatment of skeletal muscle atrophy. The technologies of cell-based gene therapy are known to those skilled in the art.

IX. Pharmaceutical Formulations and Methods for Use

Candidate compounds or candidate therapeutic compounds identified by screening methods described herein, can be administered to individuals to treat skeletal muscle atrophy. To this end, the present invention encompasses methods and compositions for modulating skeletal muscle atrophy, including, but not limited to, skeletal muscle atrophy induced by disuse due to surgery, bed rest, broken bones; denervation/nerve damage due to spinal cord injury; autoimmune disease; infectious disease; glucocorticoid use for unrelated conditions; sepsis due to infection or other causes; nutrient limitation due to illness or starvation; cancer cachexia; chronic inflammation; AIDS cachexia; COPD; congestive heart failure; sarcopenia and genetic disorders; e.g. muscular dystrophies, neurodegenerative diseases. Agonists of VPAC can be used to inhibit skeletal muscle atrophy. It is not necessary that effective compounds demonstrate absolute specificity for VPAC or for the VPAC receptor subtype of interest. It is contemplated that specific antagonist of other affected receptors can be co-administered with an effective, but nonspecific, agonist. Alternately, this lack of specificity may be addressed by modulation of dose alone, or the dosing regimen.

The candidate compounds or candidate therapeutic compounds identified by the screening methods of the present invention may be administered in conjunction with compounds which prolong or augment the activation of a VPAC receptor or of a VPAC receptor signal transduction pathway. These may be known compounds, for example, theophylline, or these compounds may be identified by the screening methods of this invention to prolong or augment the activation of a VPAC receptor or of a VPAC receptor signal transduction pathway.

Dose Determinations

Safety and therapeutic efficacy of compounds which agonize VPAC can be determined by standard procedures using either in vitro or in vivo technologies. Compounds which exhibit large therapeutic indices are preferred, although compounds with lower therapeutic indices are useful if the level of side effects is acceptable. The data obtained from the in vitro and in vivo toxicological and pharmacological techniques can be used to formulate the human range of doses which may be useful. The preferred dose lies in the range in which the circulating concentration of the compound is therapeutically maximal with acceptable safety. The circulating concentration of the compound may vary depending on the dose form, time after dosing, route of administration, etc. Doses outside this range are also useful provided the side effects are acceptable. Such matters as age and weight of the patient, and the like, can be used to determine such matters in the conventional manner. Pharmacogenetic approaches may be useful in optimizing compound selection, doses and dosing regimen in clinical populations.

Formulation and Use

Pharmaceutical compositions for use in the modulation of skeletal muscle atrophy in accordance with the present invention may be formulated using conventional methodologies using pharmaceutically acceptable carriers and excipients. The compositions of this invention are preferably provided in unit dosage form. As used herein, a "unit dosage form" is a composition of this invention containing an amount of a VPAC receptor agonist that is suitable for administration to an animal, preferably a mammal, more preferably a human subject, in a single dose, according to good medical practice. Pharmaceutical compositions may be formulated for delivery by, for example, intranasal, transdermal, inhalation, parenteral, cutaneous, oral or rectal administration. For oral administration, the pharmaceutical composition may take the form of tablets or capsules containing the pharmacologically active compound and additives including, but not limited to, binding agents, fillers, lubricants, disintegrants, or wetting agents. The tablets may be coated. Liquid preparations for oral administration include, but are not limited to, syrups, suspensions or dry products which are reconstituted with liquid vehicle before use, containing the pharmacologically active compound and additives including, but not limited to, suspending agents, emulsifying agents, non-aqueous vehicles, preservatives, buffer salts, flavoring, coloring, sweetening agents, etc. Pharmaceutical compositions for oral administration may be formulated for controlled release of the pharmacologically active compounds either in the mouth, stomach or intestinal tract.

For inhalation administration, the compounds for use according to the present invention may be delivered by, but not limited to, the following forms: liquid, powder, gel or in the form of an aerosol spray utilizing either pressurized or non-pressurized propellants in either premeasured or non-premeasured doses. The pharmacologically active compound may be formulated with appropriate fillers, vehicles, preservatives, buffers, etc. For parenteral administration, the pharmacologically active compound may be formulated with acceptable physiological carriers, preservatives, etc. and be prepared as suspensions, solutions, emulsion, powders ready for constitution, etc. for either bolus injection or infusion. Doses of these compounds may be administered by a variety of technologies including hypodermic needles, high pressure devices, etc. For rectal administration, the pharmacologically active compound may be formulated with acceptable physiological carriers, preservatives, etc. for delivery as suppositories, enemas, etc. For cutaneous administration, the pharmacologically active compound may be formulated with acceptable physiological carriers including lotions, emollients, etc. or incorporated into a patch type device. For long term administration, the pharmacologically active compound and appropriate additives such as, but limited to, polymers, hydrophobic materials, resins, etc. may be formulated as a depot preparation for either injection or implantation at multiple sites including but not limited to intramuscular and subcutaneous locations. In addition, the pharmacologically active compound may be administered by a dispensing device.

Monitoring of Effects During Clinical Trials

Monitoring the influence of compounds (e.g. drugs) on the expression or activity of VPAC can be employed not only in basic drug screening, but also in clinical trials. For example, the effectiveness of a compound determined by a screening assay to increase VPAC receptor activity or VPAC receptor expression can be assessed in clinical trials of patients with, or at risk for, skeletal muscle atrophy. At various times following administration of the test compound or placebo, the effect of the compound on the patient can be determined, for example, by observing the change in skeletal muscle mass, skeletal muscle function, biochemical markers of muscle breakdown or quality of life measures. Methods of measuring skeletal muscle mass in human subjects are known in the art and include, for example: measuring the girth of a limb; measuring muscle thickness with for instance, computer tomography, MRI or supersonics; or muscle biopsy to examine morphological and biochemical parameters (e.g. cross-section fiber area, fiber diameter or enzyme activities). Furthermore, because skeletal muscle mass is correlated with skeletal muscle function, muscle function can be used as a surrogate marker of mass and muscle mass changes can be assessed using functional measurements, e.g. strength, the force of a group of synergist muscles, or contraction characteristics found in electromyographic recordings. In addition, muscle protein loss as a result of muscle atrophy can be measured by quantitating levels of amino acids or amino acids derivatives, i.e. 3-methyl histidine, in the urine or blood of a subject. For a review of such methods see Appell, *Sports Med.* 10:42–58 (1990). Quality of life measures include, but are not limited to, the ease of getting out of a chair, number of steps taken before tiring or ability to climb stairs.

EXAMPLES

Example 1

Construction of Vectors for Human VPAC2 Receptor Expression

The human $VPAC_2$ receptor ($hVPAC_2R$) DNA sequence (Accession No. X95097) is retrieved and two oligonucleotides including one containing the 5' end of the gene beginning at the initiation codon (5' oligonucleotide) and one containing the 3' end of the gene containing the stop codon (3' oligonucleotide) are synthesized. These oligonucleotides are designed to contain restriction endonuclease sites which are not present in the $hVPAC_2$ gene with one unique site in the 5' oligonucleotide and a different unique restriction endonuclease site in the 3' oligonucleotide In addition, the 3' oligonucleotide contains a polyadenylation addition signal sequence. Double stranded cDNA from human skeletal muscle is purchased from the Universal QUICK-Clone cDNA collection (Clonetech Inc., Palo Alto, Calif., USA). Using the above 5' and 3' oligonucleotides, the $hVPAC_2R$ cDNA is amplified by PCR of the human skeletal muscle cDNA using the AdvanTaq PCR kit (Clonetech Inc., Palo Alto, Calif., USA). The $hVPAC_2$ gene PCR product is purified from PCR artifacts by agarose gel electrophoresis and the $hVPAC_2$ gene DNA fragment is purified from the agarose gel using a purification product such as NucleoTrap (Clonetech Inc., Palo Alto, Calif., USA).

Cloning of the $hVPAC_2R$ PCR product into the pIRESneo vector (Clonetech Inc., Palo Alto, Calif., USA) is accomplished by first cutting the $hVPAC_2R$ PCR product and the pIRESneo vector with the appropriate restriction endonucleases so that the 5' and 3' restriction endonuclease sites are ready for ligation. The pIRESneo vector DNA is ligated to the $hVPAC_2R$ PCR product DNA using DNA ligase, from the AdvantAge™PCR Cloning Kit (Clonetech Inc., Palo Alto, Calif., USA), according to the manufacturer's recommendations. The ligated vector and insert construct (pIRESneo/$hVPAC_2R$)is then used to transform TOP10F' competent *E. coli* cells (Clonetech Inc., Palo Alto, Calif., USA). Transformed cells are plated on LB/X-gal/IPTG plus ampicillin containing agar. White colonies (positive clones) are selected and individually cultured in LB medium. Plasmid DNA is isolated using NucleoBond DNA Purification System (Clonetech Inc., Palo Alto, Calif., USA). The insert from at least one clone is sequenced to ensure that the $hVPAC_2R$ sequence is correct. HEK293 cells containing a stably integrated Mercury CRE-LUC plasmid (Clonetech Inc., Palo Alto, Calif., USA) are transfected with purified pIRESneo/$hVPAC_2R$ DNA, having the correct sequence insert, utilizing the CalPhos™ Mammalian Transfection Kit (Clonetech Inc., Palo Alto, Calif., USA. Cells stably transfected with pIRESneo/$hVPAC_2R$ DNA are selected by culturing the cells in G418. The stably transfected cells (HEK293/CRE-LUC/pIRESneo/$hVPAC_2R$ cells) are propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), and nonessential amino acid (Life Technologies, Rockville, Md.) at 37° C. in a 5% carbon dioxide/95% air atmosphere. The clones are characterized for both VIP binding and CRE-LUC activation following exposure to VIP as described in Example 2 and Example 3. Cells expressing the $hVPAC_2$ receptor at an appropriate level and which are appropriately coupled to the CRE-LUC reporter system are then utilized for further analysis.

Example 2

Receptor Binding Assays

Receptor binding analysis of compounds is performed in whole cells by plating the HEK293/CRE-LUC/pIRESneo/$hVPAC_2R$ cells from Example 1 in a 96 well polylysine coated plate. Cells are seeded in DMEM medium containing 10% fetal bovine serum, penicillin/streptomycin solution, L-glutamine, and non-essential amino acid at 37° C. in a 5% carbon dioxide/95% air atmosphere and incubated overnight. The culture medium is removed and the appropriate amount of VIP covalently labeled with Europium (Eu-VIP) in MEM (Life Technologies, Rockville, Md.)+10% Seablock (Clonetech Inc., Palo Alto, Calif., USA) is added. The cells are incubated with the Eu-VIP for 90 minutes at room temperature then washed 4 times with phosphate buffered saline lacking magnesium and calcium (Life Technologies, Rockville, Md.). Following the final wash, enhancement solution is added (Wallac Inc., Gaithersburg, Md.) and the plate is read on a Wallac plate reader (Wallac Inc., Gaithersburg, Md.) using the BioWorks Europium program. For saturation binding analysis, log doses of Eu-VIP ranging from $10(-12)$ to $10(-3)$ M are added to the cells and binding analyzed both in the absence and presence of a saturating concentration of unlabeled VIP for evaluation of non-specific binding. For competitive binding, a concentration of Eu-VIP is added which is half maximal, in terms of binding, in addition to varying concentrations of the compound of interest.

Example 3

Receptor Activation Assay

Receptor activation analysis is performed by seeding the HEK293/CRE-LUC/pIRESneo/$hVPAC_2R$ cells of Example 1 into Packard View Plate-96 (Packard Inc., CA). Cells are seeded in DMEM medium containing 10% fetal bovine serum, penicillin/streptomycin solution, L-glutamine, and non-essential amino acid at 37° C. in a 5% carbon dioxide/95% air atmosphere and incubated overnight. The medium is then removed and replaced with DMEM (Life Technologies, Rockville, Md.) containing 0.01% bovine albumin fraction V (SIGMA, St. Louis, Mo.) containing the compound of interest. The cells are then incubated for four hours at 37° C. in a 5% carbon dioxide/95% air atmosphere after which the medium is removed and the cells are washed twice with Hanks Balanced Salt Solution (Life Technologies, Rockville, Md.). Lysis Reagent (Promega Inc., Madison, Wis.) is then added to the washed cells and the cells are incubated for 20 minutes at 37° C. in a 5% carbon dioxide/95% air atmosphere. The cells are then placed at −80° C. for 20 minutes followed by a 20 minute incubation at 37° C. in a 5% carbon dioxide/95% air atmosphere. After this incubation, Luciferase Assay Buffer and Luciferase Assay Substrate (Promega Inc., Madison, Wis.) are added to the cell lysates and luciferase activity quantitated using a luminometer. Relative activity of a compound is evaluated by comparing the increase following exposure to compound to the level of luciferase in HEK cells which contain the CRE-LUC construct without the hVPAC2 receptor following exposure to compound. Specificity of response is also checked by evaluating luciferase response of hVPAC2 receptor/CRE-LUC HEK cells to compound in the presence and absence of a 10-fold excess of hVPAC2 receptor antagonist.

Example 4
Screen to Identify Candidate Compounds that Prolong or Augment the Activation of $hVPAC_2$ Receptors or of a $VPAC_2$ Receptor Signal Transduction Pathway Identification of compounds that prolong or augment the agonist-induced activation of $VPAC_2$ receptors, or of a $VPAC_2$ receptor signal transduction pathway, involves a variation of the Receptor Activation Assay described in Example 3. Specifically, this assay is performed by seeding the HEK293/CRE-LUC/pIRESneo/$hVPAC_2$R receptor cells into Packard View Plate-96 (Packard Inc., CA). Cells are seeded in DMEM medium containing 10% fetal bovine serum, penicillin/streptomycin solution, L-glutamine, non-essential amino acid, and saturating amounts of VIP at 37° C. in a 5% carbon dioxide/95% air atmosphere and incubated for 48 hours. The medium is then removed and replaced with DMEM (Life Technologies, Rockville, Md.) containing 0.01% bovine albumin fraction V (SIGMA, St. Louis, Mo.) and VIP in addition to the compound of interest. The cells are then incubated for four hours at 37° C. in a 5% carbon dioxide/95% air atmosphere after which the medium is removed and the cells are washed twice with Hanks Balanced Salt Solution (Life Technologies, Rockville, Md.). Lysis Reagent (Promega Inc., Madison, Wis.) is then added to the washed cells and the cells are incubated for 20 minutes at 37° C. in a 5% carbon dioxide/95% air atmosphere. The cells are then placed at −80° C. for 20 minutes followed by a 20 minute incubation at 37° C. in a 5% carbon dioxide/95% air atmosphere. After this incubation, Luciferase Assay Buffer and Luciferase Assay Substrate (Promega Inc., Madison, Wis.) are added to the cell lysates and luciferase activity is quantitated using a luminometer. Test compounds which stimulate fluorescence significantly above the levels of control untreated cells, after correction for variations in cell density, are considered candidate compounds for regulating skeletal muscle mass or function. The compounds of most interest are those which induce relatively higher levels of fluorescence.

Example 5
Screens to Identify Candidate Compounds that Increase $hVPAC_2$ Receptor Expression The sequence containing the promoter region of the $hVPAC_2$ receptor gene, beginning far enough upstream of the transcriptional initiation site to contain all the regulatory elements necessary for physiological expression of the $hVPAC_2$ receptor gene in the appropriate tissue is retrieved from the human genome database. Two oligonucleotides, one containing the 5' end of the promoter region (5' oligonucleotide) and one containing the 3' end of the promoter region including the transcriptional start site (3' oligonucleotide) are synthesized. These oligonucleotides also contain restriction endonuclease sites which are not present in the $hVPAC_2$ gene regulatory region with one unique site in the 5' oligonucleotide and a different unique restriction endonuclease site in the 3' oligonucleotide. The 5' and 3' oligonucleotides are used for PCR amplification of the $hVPAC_2$ gene regulatory region from human DNA (Clonetech Inc., Palo Alto, Calif., USA) using the PCR kit, Advantage®Genomic PCR kit (Clonetech Inc., Palo Alto, Calif., USA). The $hVPAC_2$ gene regulatory region PCR product is purified from PCR artifacts by agarose gel electrophoresis and the $hVPAC_2$ gene regulatory region DNA fragment is purified from the agarose gel using a purification product such as NucleoTrap (Clonetech Inc., Palo Alto, Calif., USA). Cloning of the $hVPAC_2$ gene regulatory region PCR product into the pECFP-1 vector (Clonetech Inc., Palo Alto, Calif., USA) is accomplished by first cutting the $hVPAC_2$ gene regulatory region PCR product and the pECFP-1 vector with the appropriate restriction endonucleases so that the 5' and 3' restriction endonuclease sites are ready for ligation. Ligation of the pECFP-1 vector DNA to the $hVPAC_2$ gene regulatory region PCR product DNA is accomplished using DNA ligase from the AdvantAge™PCR Cloning Kit (Clonetech Inc., Palo Alto, Calif., USA) according to the manufacturer's recommendations. The ligated vector and insert construct is then used to transform TOP10F' competent *E. coli* cells (Clonetech Inc., Palo Alto, Calif., USA). The cells are plated on LB plus kanamycin containing agar and kanamycin resistant colonies are selected for further analysis. Kanamycin resistant clones are cultured in LB containing kanamycin medium and plasmid DNA is isolated using NucleoBond DNA Purification System (Clonetech Inc., Palo Alto, Calif., USA) and the construct containing the $hVPAC_2$ gene regulatory region is analyzed by DNA sequencing to ensure construct correctness and integrity. Purified construct plasmid DNA containing the $hVPAC_2$ gene regulatory region is then transfected into the HEK293 cells utilizing calcium phosphate-mediated transfection utilizing the CalPhos™ Mammalian Transfection Kit (Clonetech Inc., Palo Alto, Calif., USA). Transfected cell clones are selected using G418, isolated and propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), non-essential amino acid (Life Technologies, Rockville, Md.) and G418 (Life Technologies, Rockville, Md.) at 37° C. in a 5% carbon dioxide/95% air atmosphere. G418 resistant clones are characterized by Southern blotting to ensure that they contain the $hVPAC_2$ gene promoter sequence; in addition activation of the $hVPAC_2$ gene regulatory region is analyzed using an appropriate stimulating agent. Cells expressing the $hVPAC_2$ gene regulatory region-ECFP at an appropriate level are then used in assays designed to evaluate compounds which can modulate the activity of the $hVPAC_2$ gene regulatory region as follows. The regulatory region activation analysis is performed by seeding the $hVPAC_2$ gene regulatory region-ECFP containing HEK293 cells at an appropriate density into black with clear bottom 96 well microtiter plates and allowed to grow overnight. The following day, the medium is removed and the test compound added in fresh growth medium. The cells are incubated for 16 hours at 37° C. in a 5% carbon dioxide/95% air atmosphere followed by measurement of fluorescence (excitation at 433 (453) nm by detecting emission at 475(501) nm using a fluorometer (biolumin™ 960, Molecular Dynamics/Amersham Pharmacia Biotech, Piscataway, N.J.). Test compounds which stimulate fluorescence significantly above the levels of control untreated cells, after correction for variations in cell density, are considered candidate compounds for regulating skeletal muscle mass or function. The compounds of most interest are those which induce relatively higher levels of fluorescence.

Example 6
Screens to Identify Compounds that Increase Human VIP Expression

The methods for identifying compounds that increase human VIP (hVIP) expression are essentially identical to those for identifying compounds which increase $hVPAC_2$ receptor expression except the regulatory region used is that for the hVIP gene. The sequence containing the regulatory region of the hVIP gene, beginning far enough upstream of the transcriptional initiation site to contain all the regulatory elements necessary for physiological expression of the hVIP gene in the appropriate tissue is retrieved from the human genome database. Two oligonucleotides, one containing the 5' end of the regulatory region (5' oligonucleotide) and one containing the 3' end of the regulatory region including the transcriptional start site (3' oligonucleotide) are synthesized. These oligonucleotides also contain restriction endonuclease sites which are not present in the hVIP gene regulatory region with one unique site in the 5' oligonucleotide and a different unique restriction endonuclease site in the 3' oligonucleotide. The 5' and 3' oligonucleotides are used for PCR amplification of the hVIP gene regulatory region from human DNA (Clonetech Inc., Palo Alto, Calif., USA) using the Advantage®Genomic PCR kit (Clonetech Inc., Palo Alto, Calif., USA). The hVIP gene regulatory region PCR product is purified from PCR artifacts by agarose gel electrophoresis and the hVIP gene regulatory region DNA fragment is purified from the agarose gel using the purification product, NucleoTrap (Clonetech Inc., Palo Alto, Calif., USA). Cloning of the hVIP gene regulatory region PCR product into the pECFP-1 vector (Clonetech Inc., Palo Alto, Calif., USA) is accomplished by first cutting the hVIP gene regulatory region PCR product and the pECFP-1 vector with the appropriate restriction endonucleases so that the 5' and 3' restriction endonuclease sites are ready for ligation. Ligation of the pECFP-1 vector DNA to the hVIP gene regulatory region PCR product DNA is accomplished using DNA ligase from AdvantAge™PCR Cloning Kit (Clonetech Inc., Palo Alto, Calif., USA) according to the manufacturer's recommendations. The ligated vector and insert construct is then used to transform TOP10F' competent $E.\ coli$ cells (Clonetech Inc., Palo Alto, Calif., USA). The cells are plated on LB plus kanamycin containing agar and kanamycin resistant colonies are selected for further analysis. Kanamycin resistant clones are cultured in LB containing kanamycin medium and plasmid DNA is isolated using NucleoBond DNA Purification System (Clonetech Inc., Palo Alto, Calif., USA) and the construct containing the hVIP gene regulatory region is analyzed by DNA sequencing to ensure construct correctness and integrity. Purified construct plasmid DNA containing the hVIP gene regulatory region is then transfected into the HEK293 cells utilizing calcium phosphate-mediated transfection utilizing the CalPhos™ Mammalian Transfection Kit (Clonetech Inc., Palo Alto, Calif., USA). Transfected cell clones are selected using G418, isolated and propagated in DMEM (Life Technologies, Rockville, Md.) containing 10% fetal bovine serum (Clonetech Inc., Palo Alto, Calif., USA), penicillin/streptomycin solution (Life Technologies, Rockville, Md.), L-glutamine (Life Technologies, Rockville, Md.), non-essential amino acid (Life Technologies, Rockville, Md.) and G418 (Life Technologies, Rockville, Md.) at 37° C. in a 5% carbon dioxide/95% air atmosphere. G418 resistant clones are characterized by Southern blotting to ensure that they contain the hVIP gene regulatory region sequence; in addition activation of the hVIP gene regulatory region is analyzed using an appropriate stimulating agent. Cells expressing the hVIP gene regulatory region-ECFP at an appropriate level are then used in assays designed to evaluate compounds which can modulate the activity of the hVIP gene regulatory region as follows. The regulatory region activation analysis is performed as in Example 5 except that clones containing the hVIP gene regulatory region construct are used.

Example 7

Method of Making Human Antibodies Which Activate the hVPAC$_2$ Receptor

Fully human monoclonal antibodies which activate the hVPAC$_2$ receptor are produced by first generating recombinant hVPAC$_2$ receptor protein as follows. The procedure from Example 1 is followed to obtain the hVPAC$_2$ PCR product. This hVPAC$_2$ PCR product is then cloned into the pHAT20 vector (Clonetech Inc., Palo Alto, Calif., USA) by first cutting the hVPAC2 gene PCR product and the pHAT20 vector with the appropriate restriction endonucleases so that the 5' and 3' restriction endonuclease sites are ready for ligation. Ligation of the pHAT20 vector DNA to the hVPAC$_2$ gene PCR product DNA is accomplished using DNA ligase from the AdvantAge™PCR Cloning Kit (Clonetech Inc., Palo Alto, Calif., USA) according to the manufacturer's recommendations. The ligated vector/insert construct is then used to transform TOP10F' competent $E.\ coli$ cells (Clonetech Inc., Palo Alto, Calif., USA). Transformed cells are plated on LB plus ampicillin containing agar and ampicillin resistant colonies are selected for further analysis. Positive clones are cultured in LB medium containing ampicillin and plasmid DNA is isolated using NucleoBond DNA Purification System (Clonetech Inc., Palo Alto, Calif., USA) and the construct containing the hVPAC$_2$ gene is analyzed by DNA sequencing the ensure construct correctness and integrity. The hVPAC$_2$-pHAT20 vector DNA is then used for additional PCR cloning by utilizing a 5' oligonucleotide containing the beginning of the HAT sequence and a unique restriction endonuclease site not present in the hVPAC2-pHAT20 construct and the 3' hVPAC2 oligonucleotide utilized previously. The oligonucleotide primers are used to PCR amplify the HAT-hVPAC2 fusion gene from the hVPAC$_2$-pHAT20 construct and the PCR product is purified as described above. The HAT-hVPAC$_2$ fusion gene PCR product is then utilized for cloning into the pBacPAK8 vector using the BacPAK Baculovirus Expression System from Clonetech (Clonetech Inc., Palo Alto, Calif., USA). The ligation of the HAT-hVPAC$_2$ fusion gene into the pBacPAK8 vector is essentially as described above. The hVPAC2/HAT-pBacPAK8 construct is then transfected into TOP10'F competent $E.\ coli$ cells, ampicillin resistant cells are selected and plasmid DNA is isolated and checked for construct integrity as described above. This construct is then cotransfected with linearized BacPAK6 DNA into Sf21 insect host cells utilizing the CalPhos™ Mammalian Transfection Kit (Clonetech Inc., Palo Alto, Calif., USA). The insect cells are then incubated for 2–3 days followed by harvest of virus from individual clear plaques. The virus is then amplified in Sf21 cells, the harvested virus titered, and the titered virus used for large scale infection of Sf21 cells utilizing BacPAK Insect Cell Media—all according to the manufacturers recommendations (Clonetech Inc., Palo Alto, Calif., USA). Recombinant HAT-VPAC2 fusion protein is then purified using the TALON® CellThru Purification Kit from Clonetech (Clonetech Inc., Palo Alto, Calif., USA) using conditions recommended by the manufacturer. Briefly, infected Sf21 cells are harvested 48 hours after infection and sonicated in extraction/loading buffer. The cell lysate is then put through a TALON® CellThru column. The column is washed twice with extraction/loading buffer and the bound HAT-hVPAC$_2$ protein is eluted with elution buffer. The eluted protein is analyzed by SDS-PAGE for integrity and protein concentration is quantitated using the Bio-Rad SDS-PAGE system and protein quantitation systems according to the manufacturer's recommendations (BioRad Laboratories, Hercules, Calif.). Purified HAT-hVPAC$_2$ fusion protein is then used for immunizing XenoMouse animals (Abgenix Inc., Fremont, Calif.) for human monoclonal antibody production as follows. 10 μg of purified recombinant HAT-hVPAC$_2$ fusion protein in combination with 25 μg of adjuvant monophosphoryl lipid A (Sigma, St. Louis, Mo.) is used to vaccinate 10 XenoMouse animals multiple times over an eight week period. Serum is obtained from vaccinated animals and utilized in an antigen capture ELISA utilizing purified HAT-hVPAC2 fusion protein to detect antibodies to the HAT-hVPAC2 protein by coating polystyrene ELISA plates (Corning Glass Works, Corning, N.Y.) with HAT-hVPAC2 fusion protein, blocked with PBS-1% BSA, washed and incubated at 37° C. for 1 hour with a 1:50 dilution of the serum samples. After washing 5 times with PBS, the plates are incubated at 37° C. for 1 hour with alkaline phosphatase-conjugated goat antibodies to human immunoglobulin G. The plates are then washed 5× with PBS and antibodies detected with p-nitrophenyl phosphate substrate (Sigma, St. Louis, Mo.) in buffer. Optical densities at 405 nm were measured using a plate reader and signal quantitated. Mice with demonstrated high antibody production are used for hybridoma formation. Hybridomas are generated by fusion of splenic cells from the XenoMouse animals with nonsecreting myeloma cell line NSA-bcl 2 using a 4:1 ratio of spleen cells to NSA-bcl2 cells in the presence of 30% polyethylene glycol PEG1450. Fused cells are individually cloned by limiting dilution into 96 well plates and cultured in RPMI-1640 medium containing 10% fetal bovine serum, nonessential amino acids, sodium pyruvate, L-glutamine, 100 u/ml penicillin-streptomycin and hypoxanthine-aminopterin-thymidine (all from Life Technologies, Rockville, Md.). Supernatants from the hypoxanthine-aminopterin-thymidine selected hybridomas were screened for human antibody production by ELISA as described previously. Hybridomas which produce human antibodies to the HAT-hVPAC2 fusion protein are selected for large scale antibody production. Monoclonal antibodies are purified by Protein G-Sepharose chromatography. Briefly, the supernatant from cultured hybridoma clones is loaded onto a Protein G-Sepharose column (SIGMA, St. Louis, Mo.) in loading buffer, washed 3 times and the IgG is eluted with elution buffer. These antibodies are then used for screening to evaluate hVPAC$_2$ activation (agonism) potential. This is accomplished using the methodology as outlined in Example 3. Those human monoclonal antibodies which demonstrate agonist activity toward the hVPAC2 receptor are designated candidate compounds.

Example 8
Therapeutic Treatment of Skeletal Muscle Atrophy Using a Human Antibody that is an Agonist of the VPAC$_2$ Receptor A human male subject weighing 50 kg and having significant muscular atrophy of the arms and legs due to prolonged bed rest, is treated to reverse the skeletal muscle atrophy. Once each week for a period of 3 months, 15 mls of an aqueous solution of pH 6.comprising the anti-VPAC$_2$ receptor is administered to the subject via intravenous injection. The solution comprises the following:

| Component | Concentration (mg/ml) |
|---|---|
| VPAC$_2$ receptor agonist antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 mL |

At the end of the treatment period, the subject exhibits measurable increases of muscle mass, strength and mobility of the arms and legs.

Example 9
Prophylactic Treatment of Skeletal Muscle Atrophy using a Human Antibody that is an Agonist of the VPAC$_2$ Receptor A human female subject weighing 55 kg is scheduled for hip joint replacement surgery in one month. The subject is treated to enhance skeletal muscle mass prior to and following surgery to ultimately reduce the level of skeletal muscle atrophy due to muscle disuse during post-surgery recovery. Specifically, once each week for a period of 1 month prior to surgery and for 2 months post-surgery, 18 ml of an aqueous solution of pH 6.0 comprising the anti-VPAC$_2$ receptor is administered to the subject via intravenous injection. The solution comprises the following:

| Component | Concentration (mg/ml) |
|---|---|
| VPAC activating antibody | 20 |
| L-histidine HCl | 0.47 |
| L-histidine | 0.3 |
| α, α-trehalose dihydrate | 20 |
| Polysorbate 20 | 0.1 |
| Bacteriostatic Sterile water | qs to 1 ml |

At the end of the treatment period, the subject exhibits measurable preservation of muscle mass, strength and mobility of the arms and legs as compared to the subject's expected status without antibody therapy.

Example 10
Prophylactic Treatment of Skeletal Muscle Atrophy using a Human Antibody that is an Agonist of the VPAC$_1$ Receptor.

A human female subject weighing 45 kg undergoes a casting procedure to treat a simple fracture of the humerus after a fall. The subject is treated to prevent atrophy of the skeletal muscle of the affected arm and shoulder due to disuse and limited use during fracture healing. Specifically, once each week starting on the day of casting, 13 ml of pH 6.0 comprising the anti-VPAC$_1$ receptor is administered to the subject via intravenous injection. The solution comprises the following:

| Component | Concentration (mg/ml) |
|---|---|
| VPAC$_1$ activating antibody | 20 |
| L-histidine HCl | 0.47 |
| L-histidine | 0.3 |
| α, α-trehalose dihydrate | 20 |
| Polysorbae 20 | 0.1 |
| Bacteriostatic Sterile water | qs to 1 mL |

At the end of the treatment period, the subject exhibits measurable preservation of muscle mass, strength and mobility of the affected arm and shoulder and a reduced course of physical therapy as compared to the subject's expected status and follow-up treatment without antibody therapy.

Example 11
Prophylactic Treatment of Skeletal Muscle Atrophy Using an Agonist of the VPAC$_2$ Receptor, Ro 25-1553

A human female subject weighing 50 kg is admitted to the hospital in a comatose state. The subject is treated to prevent atrophy of the skeletal muscle of the entire body due to disuse while in the comatose state. Specifically, once each month while in the coma, the subject is administered, via intramuscular injection, 3 ml of an aqueous solution of pH 6.0 comprising the following:

| Component | Concentration (mg/ml) |
| --- | --- |
| Ro 25-1553 (VPAC agonist) | 500 |
| D,L lactic and glycolic acid copolymer | 5 |

As a result of treatment, the subject exhibits measurable preservation of skeletal muscle mass and reduced physical therapy needs during the coma and after regaining consciousness, as compared to the subject's expected status without drug therapy.

The present invention is not to be limited in scope by the specific embodiments described which are intended solely as illustrations of individual aspects of the invention, and functionally equivalent methods and components are within the scope of the invention. These include, but are not limited to, species of test animal, nature and type of VPAC agonists, sex of the animal, model of atrophy, method of activating VPAC including genetic methodologies, etc. Various modifications of the invention, in addition to those shown and described herein will be apparent to those skilled in the art upon reading foregoing description and accompanying figures. Such modifications are intended to fall within the scope of the appended claims.

All references herein are incorporated herein by reference.

What is claimed is:

1. A method for increasing skeletal muscle mass or function in a subject, comprising:
   (a) identifying a subject in which an increase in muscle mass or function is desirable; and
   (b) administering to the subject a safe and effective amount of a VPAC receptor agonist selected from the group consisting of Ro 25-1553, and PACAP-38.

2. The method for increasing skeletal muscle mass or function according to claim 1, wherein the compound is Ro 25-1553.

3. The method for increasing skeletal muscle mass or function according to claim 1, wherein the compound is PACAP-38.

* * * * *

SEQUENCE LISTING

<160> NUMBER OF SEQ ID NOS: 16

<210> SEQ ID NO 1
<211> LENGTH: 457
<212> TYPE: PRT
<213> ORGANISM: homo sapiens;

<400> SEQUENCE: 1

Met Arg Pro Pro Ser Pro Leu Pro Ala Arg Trp Leu Cys Val Leu Ala
1               5                   10                  15

Gly Ala Leu Ala Trp Ala Leu Gly Pro Ala Gly Gly Gln Ala Ala Arg
            20                  25                  30

Leu Gln Glu Glu Cys Asp Tyr Val Gln Met Ile Glu Val Gln His Lys
        35                  40                  45

Gln Cys Leu Glu Glu Ala Gln Leu Glu Asn Glu Thr Ile Gly Cys Ser
    50                  55                  60

Lys Met Trp Asp Asn Leu Thr Cys Trp Pro Ala Thr Pro Arg Gly Gln
65                  70                  75                  80

Val Val Val Leu Ala Cys Pro Leu Ile Phe Lys Leu Phe Ser Ser Ile
            85                  90                  95

Gln Gly Arg Asn Val Ser Arg Ser Cys Thr Asp Glu Gly Trp Thr His
            100                 105                 110

Leu Glu Pro Gly Pro Tyr Pro Ile Ala Cys Gly Leu Asp Asp Lys Ala
        115                 120                 125

Ala Ser Leu Asp Glu Gln Gln Thr Met Phe Tyr Gly Ser Val Lys Thr
    130                 135                 140

Gly Tyr Thr Ile Gly Tyr Gly Leu Ser Leu Ala Thr Leu Leu Val Ala
145                 150                 155                 160

Thr Ala Ile Leu Ser Leu Phe Arg Lys Leu His Cys Thr Arg Asn Tyr
                165                 170                 175

Ile His Met His Leu Phe Ile Ser Phe Ile Leu Arg Ala Ala Ala Val
            180                 185                 190

Phe Ile Lys Asp Leu Ala Leu Phe Asp Ser Gly Glu Ser Asp Gln Cys
        195                 200                 205

Ser Glu Gly Ser Val Gly Cys Lys Ala Ala Met Val Phe Phe Gln Tyr
    210                 215                 220

```
Cys Val Met Ala Asn Phe Phe Trp Leu Leu Val Glu Gly Leu Tyr Leu
225                 230                 235                 240

Tyr Thr Leu Leu Ala Val Ser Phe Phe Ser Glu Arg Lys Tyr Phe Trp
            245                 250                 255

Gly Tyr Ile Leu Ile Gly Trp Gly Val Pro Ser Thr Phe Thr Met Val
            260                 265                 270

Trp Thr Ile Ala Arg Ile His Phe Glu Asp Tyr Gly Cys Trp Asp Thr
            275                 280                 285

Ile Asn Ser Ser Leu Trp Trp Ile Ile Lys Gly Pro Ile Leu Thr Ser
            290                 295                 300

Ile Leu Val Asn Phe Ile Leu Phe Ile Cys Ile Ile Arg Ile Leu Leu
305                 310                 315                 320

Gln Lys Leu Arg Pro Pro Asp Ile Arg Lys Ser Asp Ser Ser Pro Tyr
                325                 330                 335

Ser Arg Leu Ala Arg Ser Thr Leu Leu Leu Ile Pro Leu Phe Gly Val
            340                 345                 350

His Tyr Ile Met Phe Ala Phe Phe Pro Asp Asn Phe Lys Pro Glu Val
            355                 360                 365

Lys Met Val Phe Glu Leu Val Val Gly Ser Phe Gln Gly Phe Val Val
370                 375                 380

Ala Ile Leu Tyr Cys Phe Leu Asn Gly Glu Val Gln Ala Glu Leu Arg
385                 390                 395                 400

Arg Lys Trp Arg Arg Trp His Leu Gln Gly Val Leu Gly Trp Asn Pro
            405                 410                 415

Lys Tyr Arg His Pro Ser Gly Gly Ser Asn Gly Ala Thr Cys Ser Thr
            420                 425                 430

Gln Val Ser Met Leu Thr Arg Val Ser Pro Gly Ala Arg Arg Ser Ser
            435                 440                 445

Ser Phe Gln Ala Glu Val Ser Leu Val
    450                 455

<210> SEQ ID NO 2
<211> LENGTH: 460
<212> TYPE: PRT
<213> ORGANISM: homo sapiens;

<400> SEQUENCE: 2

Met Arg Pro Pro Ser Pro Leu Pro Ala Arg Trp Leu Cys Val Leu Ala
1               5                   10                  15

Gly Ala Leu Ala Trp Ala Leu Gly Pro Ala Gly Gly Gln Ala Ala Arg
            20                  25                  30

Leu Gln Glu Glu Cys Asp Tyr Val Gln Met Ile Glu Val Gln His Lys
        35                  40                  45

Gln Cys Leu Glu Glu Ala Gln Leu Glu Asn Glu Thr Ile Gly Cys Ser
    50                  55                  60

Lys Met Trp Asp Asn Leu Thr Cys Trp Pro Ala Thr Pro Arg Gly Gln
65                  70                  75                  80

Val Val Val Leu Ala Cys Pro Leu Ile Phe Lys Leu Phe Ser Ser Ile
                85                  90                  95

Gln Gly Arg Asn Val Ser Arg Ser Cys Thr Asp Glu Gly Trp Thr His
            100                 105                 110

Leu Glu Pro Gly Pro Tyr Pro Ile Ala Cys Gly Leu Asp Asp Lys Ala
        115                 120                 125

Ala Ser Leu Asp Glu Gln Gln Thr Met Phe Tyr Gly Ser Val Lys Thr
```

-continued

Gly Tyr Thr Ile Gly Tyr Gly Leu Ser Leu Ala Thr Leu Leu Val Ala
145                 150                 155                 160

Thr Ala Ile Leu Ser Leu Phe Arg Lys Leu His Cys Thr Arg Asn Tyr
            165                 170                 175

Ile His Met His Leu Phe Ile Ser Phe Ile Leu Arg Ala Ala Ala Val
            180                 185                 190

Phe Ile Lys Asp Leu Ala Leu Phe Asp Ser Gly Glu Ser Asp Gln Cys
            195                 200                 205

Ser Glu Gly Ser Val Gly Cys Lys Ala Ala Met Val Phe Phe Gln Tyr
            210                 215                 220

Cys Val Met Ala Asn Phe Phe Trp Leu Leu Val Glu Gly Leu Tyr Leu
225                 230                 235                 240

Tyr Thr Leu Leu Ala Val Ser Phe Phe Ser Glu Arg Lys Tyr Phe Trp
            245                 250                 255

Gly Tyr Ile Leu Ile Gly Trp Gly Val Pro Ser Thr Phe Thr Met Val
            260                 265                 270

Trp Thr Ile Ala Arg Ile His Phe Glu Asp Tyr Gly Leu Leu Arg Cys
275                 280                 285

Trp Asp Thr Ile Asn Ser Ser Leu Trp Trp Ile Ile Lys Gly Pro Ile
290                 295                 300

Leu Thr Ser Ile Leu Val Asn Phe Ile Leu Phe Ile Cys Ile Ile Arg
305                 310                 315                 320

Ile Leu Leu Gln Lys Leu Arg Pro Pro Asp Ile Arg Lys Ser Asp Ser
            325                 330                 335

Ser Pro Tyr Ser Arg Leu Ala Arg Ser Thr Leu Leu Leu Ile Pro Leu
            340                 345                 350

Phe Gly Val His Tyr Ile Met Phe Ala Phe Phe Pro Asp Asn Phe Lys
            355                 360                 365

Pro Glu Val Lys Met Val Phe Glu Leu Val Val Gly Ser Phe Gln Gly
            370                 375                 380

Phe Val Val Ala Ile Leu Tyr Cys Phe Leu Asn Gly Glu Val Gln Ala
385                 390                 395                 400

Glu Leu Arg Arg Lys Trp Arg Arg Trp His Leu Gln Gly Val Leu Gly
            405                 410                 415

Trp Asn Pro Lys Tyr Arg His Pro Ser Gly Gly Ser Asn Gly Ala Thr
            420                 425                 430

Cys Ser Thr Gln Val Ser Met Leu Thr Arg Val Ser Pro Gly Ala Arg
            435                 440                 445

Arg Ser Ser Ser Phe Gln Ala Glu Val Ser Leu Val
            450                 455                 460

<210> SEQ ID NO 3
<211> LENGTH: 459
<212> TYPE: PRT
<213> ORGANISM: rattus norvegicus;

<400> SEQUENCE: 3

Met Arg Pro Pro Ser Pro Pro His Val Arg Trp Leu Cys Val Leu Ala
1               5                   10                  15

Gly Ala Leu Ala Cys Ala Leu Arg Pro Ala Gly Ser Gln Ala Ala Ser
            20                  25                  30

Pro Gln His Glu Cys Glu Tyr Leu Gln Leu Ile Glu Ile Gln Arg Gln
            35                  40                  45

-continued

```
Gln Cys Leu Glu Glu Ala Gln Leu Glu Asn Glu Thr Thr Gly Cys Ser
 50                  55                  60

Lys Met Trp Asp Asn Leu Thr Cys Trp Pro Thr Pro Arg Gly Gln
 65                  70                  75                  80

Ala Val Val Leu Asp Cys Pro Leu Ile Phe Gln Leu Phe Ala Pro Ile
                 85                  90                  95

His Gly Tyr Asn Ile Ser Arg Ser Cys Thr Glu Gly Trp Ser Gln
            100                 105                 110

Leu Glu Pro Gly Pro Tyr His Ile Ala Cys Gly Leu Asn Asp Arg Ala
            115                 120                 125

Ser Ser Leu Asp Glu Gln Gln Thr Lys Phe Tyr Asn Thr Val Lys
130                 135                 140

Thr Gly Tyr Thr Ile Gly Tyr Ser Leu Ser Leu Ala Ser Leu Leu Val
145                 150                 155                 160

Ala Met Ala Ile Leu Ser Leu Phe Arg Lys Leu His Cys Thr Arg Asn
                165                 170                 175

Tyr Ile His Met His Leu Phe Met Ser Phe Ile Leu Arg Ala Thr Ala
            180                 185                 190

Val Phe Ile Lys Asp Met Ala Leu Phe Asn Ser Gly Glu Ile Asp His
            195                 200                 205

Cys Ser Glu Ala Ser Val Gly Cys Lys Ala Ala Val Phe Phe Gln
210                 215                 220

Tyr Cys Val Met Ala Asn Phe Phe Trp Leu Leu Val Glu Gly Leu Tyr
225                 230                 235                 240

Leu Tyr Thr Leu Leu Ala Val Ser Phe Phe Ser Glu Arg Lys Tyr Phe
                245                 250                 255

Trp Gly Tyr Ile Leu Ile Gly Trp Gly Val Pro Ser Val Phe Ile Thr
            260                 265                 270

Ile Trp Thr Val Val Arg Ile Tyr Phe Glu Asp Phe Gly Cys Trp Asp
            275                 280                 285

Thr Ile Ile Asn Ser Ser Leu Trp Trp Ile Ile Lys Ala Pro Ile Leu
290                 295                 300

Leu Ser Ile Leu Val Asn Phe Val Leu Phe Ile Cys Ile Ile Arg Ile
305                 310                 315                 320

Leu Val Gln Lys Leu Arg Pro Pro Asp Ile Gly Lys Asn Asp Ser Ser
                325                 330                 335

Pro Tyr Ser Arg Leu Ala Lys Ser Thr Leu Leu Leu Ile Pro Leu Phe
            340                 345                 350

Gly Ile His Tyr Val Met Phe Ala Phe Phe Pro Asp Asn Phe Lys Ala
            355                 360                 365

Gln Val Lys Met Val Phe Glu Leu Val Val Gly Ser Phe Gln Gly Phe
            370                 375                 380

Val Val Ala Ile Leu Tyr Cys Phe Leu Asn Gly Glu Val Gln Ala Glu
385                 390                 395                 400

Leu Arg Arg Lys Trp Arg Arg Trp His Leu Gln Gly Val Leu Gly Trp
                405                 410                 415

Ser Ser Lys Ser Gln His Pro Trp Gly Gly Ser Asn Gly Ala Thr Cys
            420                 425                 430

Ser Thr Gln Val Ser Met Leu Thr Arg Val Ser Pro Ser Ala Arg Arg
            435                 440                 445

Ser Ser Ser Phe Gln Ala Glu Val Ser Leu Val
450                 455
```

-continued

```
<210> SEQ ID NO 4
<211> LENGTH: 459
<212> TYPE: PRT
<213> ORGANISM: mus musculus;

<400> SEQUENCE: 4

Met Arg Pro Pro Ser Leu Pro Pro Ala Arg Trp Leu Cys Val Leu Ala
1               5                   10                  15

Gly Ala Leu Ala Cys Ala Leu Gly Pro Ala Gly Ser Arg Ala Ala Ser
            20                  25                  30

Pro His Gln Glu Cys Glu Tyr Leu Gln Met Ile Glu Lys Gln Arg Gln
        35                  40                  45

Gln Cys Leu Glu Glu Ala Gln Leu Glu Asn Lys Thr Thr Gly Cys Ser
    50                  55                  60

Lys Met Trp Asp Asn Leu Thr Cys Trp Pro Thr Thr Pro Trp Gly Gln
65                  70                  75                  80

Val Val Val Leu Asp Cys Pro Leu Ile Phe Gln Leu Phe Ser Pro Ile
                85                  90                  95

His Gly Tyr Asn Ile Ser Arg Asn Cys Thr Glu Glu Gly Trp Ser Gln
            100                 105                 110

Leu Glu Pro Gly Pro Tyr His Ile Ala Cys Gly Leu Asn Asp Arg Ala
        115                 120                 125

Ser Ser Met Asp Glu Gln Gln Gln Thr Glu Phe Tyr Asp Ala Val Lys
    130                 135                 140

Thr Gly Tyr Thr Ile Gly Tyr Ser Leu Ser Leu Ala Ser Leu Leu Val
145                 150                 155                 160

Ala Met Ala Ile Leu Ser Leu Phe Arg Lys Leu His Cys Thr Arg Asn
                165                 170                 175

Tyr Ile His Met His Leu Phe Met Ser Phe Ile Leu Arg Ala Thr Ala
            180                 185                 190

Val Phe Ile Lys Asp Met Ala Leu Phe Asn Asn Gly Glu Thr Asp His
        195                 200                 205

Cys Ser Glu Ala Ser Val Ser Cys Lys Ala Ala Val Phe Phe Gln
    210                 215                 220

Tyr Cys Val Met Ala Asn Phe Phe Trp Leu Leu Val Glu Gly Leu Tyr
225                 230                 235                 240

Leu His Thr Leu Leu Ala Val Ser Phe Phe Ser Glu Arg Lys Tyr Phe
                245                 250                 255

Trp Gly Tyr Ile Leu Ile Gly Trp Gly Val Pro Ser Val Phe Ile Met
            260                 265                 270

Ile Trp Thr Ile Val Arg Ile His Phe Glu Asp Phe Gly Cys Trp Asp
        275                 280                 285

Thr Ile Ile Asn Ser Ser Leu Trp Trp Ile Ile Lys Gly Pro Ile Leu
    290                 295                 300

Ile Ser Ile Leu Val Asn Phe Ile Leu Phe Ile Cys Ile Ile Arg Ile
305                 310                 315                 320

Leu Val Gln Lys Leu Arg Pro Pro Asp Ile Gly Lys Asn Asp Ser Ser
                325                 330                 335

Pro Tyr Ser Arg Leu Ala Lys Ser Thr Leu Leu Ile Pro Leu Phe
            340                 345                 350

Gly Val His Tyr Val Met Phe Ala Phe Phe Pro Asp Asn Phe Lys Ala
        355                 360                 365

Gln Val Lys Met Val Phe Glu Leu Val Val Gly Ser Phe Gln Gly Phe
    370                 375                 380
```

```
Val Val Ala Ile Leu Tyr Cys Phe Leu Asn Gly Glu Val Gln Ala Glu
385                 390                 395                 400

Leu Arg Arg Lys Trp Arg Arg Trp His Leu Gln Gly Val Leu Gly Trp
            405                 410                 415

Ser Ser Lys Ser Gln His Pro Trp Gly Gly Ser Asn Gly Val Ser Cys
            420                 425                 430

Ser Thr Gln Val Ser Met Leu Thr Arg Val Ser Pro Ser Ala Arg Arg
            435                 440                 445

Ser Ser Ser Phe Gln Ala Glu Val Ser Leu Val
            450                 455

<210> SEQ ID NO 5
<211> LENGTH: 458
<212> TYPE: PRT
<213> ORGANISM: sus scrofa;

<400> SEQUENCE: 5

Met Arg Pro Leu Ser Pro Pro Ala Gly Trp Phe Cys Val Leu Ala
1               5                   10                  15

Gly Val Leu Ala Cys Val Leu Gly Pro Val Gly Ser Trp Ala Val Gly
                20                  25                  30

Leu Gln Gln Glu Glu Cys Asp Tyr Leu Gln Met Ile Lys Val Gln His
                35                  40                  45

Lys Gln Cys Leu Glu Glu Ala Gln Leu Glu Asn Glu Thr Ser Gly Cys
    50                  55                  60

Ser Lys Met Trp Asp Asn Leu Thr Cys Trp Pro Ala Thr Pro Arg Gly
65                  70                  75                  80

Gln Val Val Leu Ala Cys Pro Leu Ile Phe Lys Leu Phe Ser Pro
                85                  90                  95

Thr Gln Gly Leu Asn Val Ser Arg Asn Cys Thr Asp Glu Gly Trp Thr
                100                 105                 110

Pro Leu Glu Pro Gly Pro Tyr Pro Ile Ala Cys Gly Met Asp Asp Lys
            115                 120                 125

Ala Ser Gly Leu Asp Glu Gln Gln Thr Val Phe Tyr Asn Ser Val Lys
    130                 135                 140

Thr Gly Tyr Thr Ile Gly Tyr Ser Leu Ser Leu Ala Ala Leu Leu Val
145                 150                 155                 160

Ala Thr Ala Ile Leu Ser Leu Phe Arg Lys Leu His Cys Thr Arg Asn
                165                 170                 175

Tyr Ile His Met His Leu Phe Ile Ser Phe Ile Leu Arg Ala Thr Ala
                180                 185                 190

Val Phe Ile Lys Asp Leu Ala Leu Phe Asp Ser Glu Glu Ser Asp His
                195                 200                 205

Cys Ser Lys Gly Ser Val Gly Cys Lys Ala Ala Val Val Leu Phe Gln
    210                 215                 220

Tyr Cys Val Met Ala Asn Phe Phe Trp Leu Leu Val Glu Gly Leu Tyr
225                 230                 235                 240

Leu His Thr Leu Leu Ala Val Ser Phe Phe Ser Glu Arg Lys Tyr Phe
                245                 250                 255

Trp Gly Tyr Ile Phe Val Gly Trp Gly Val Pro Ser Thr Phe Ile Met
                260                 265                 270

Val Trp Thr Val Val Arg Ile His Phe Glu Asp Tyr Gly Cys Trp Asp
            275                 280                 285

Thr Ile His Ser Ser Leu Trp Trp Ile Ile Lys Ala Pro Ile Leu Ala
    290                 295                 300
```

```
Ser Ile Leu Val Asn Phe Ile Leu Phe Ile Arg Ile Gly Ile Leu
305                 310                 315                 320

Val Gln Lys Leu Arg Pro Pro Asp Val Gly Lys Ser Asp Asn Ser Pro
            325                 330                 335

Tyr Ser Arg Leu Ala Lys Ser Thr Leu Leu Ile Pro Leu Phe Gly
        340                 345                 350

Val His Tyr Ile Met Phe Ala Phe Pro Asp Asn Phe Lys Ala Glu
        355                 360                 365

Val Lys Met Val Phe Glu Leu Ile Val Gly Ser Phe Gln Gly Cys Val
370                 375                 380

Val Ala Ile Leu Tyr Cys Phe Leu Asn Gly Glu Val Gln Ala Glu Leu
385                 390                 395                 400

Arg Arg Lys Trp Arg Arg Trp His Gln Gln Gly Val Leu Gly Trp Asp
                405                 410                 415

Ser Lys Tyr Gln His Pro Ser Gly Gly Ser Asn Gly Asp Thr Cys Ser
                420                 425                 430

Thr Gln Val Ser Met Leu Thr Arg Val Ser Pro Ser Ala Arg Arg Ser
            435                 440                 445

Ser Ser Phe Gln Ala Glu Val Ser Leu Val
    450                 455

<210> SEQ ID NO 6
<211> LENGTH: 444
<212> TYPE: PRT
<213> ORGANISM: rana ridibunda;

<400> SEQUENCE: 6

Met Glu Phe Leu Pro Leu Leu Leu Cys Leu Thr Gly Leu Phe Ser Pro
1               5                   10                  15

Ile Leu Cys Val Pro Glu Glu Cys Ser Ile Met Tyr Gln Ile Glu Leu
            20                  25                  30

Lys His Glu Glu Cys Val Asn His Glu Asp Tyr Phe Asn Asp Thr Ala
        35                  40                  45

Val Cys Lys Arg Thr Trp Asp Asn Ile Thr Cys Trp Pro Ser Ala Ser
50                  55                  60

Ile Gly Glu Val Val Leu Gln Cys Pro Gly Tyr Phe Ser Met Phe
65                  70                  75                  80

Thr Thr Gly Thr Val Asn Gly Asn Val Ser Lys Asn Cys Thr Ser Glu
                85                  90                  95

Gly Trp Ser Glu Met Tyr Pro Ala Thr Tyr Ala Ala Cys Gly Phe
            100                 105                 110

Ser Thr Asn Asp Thr Pro Thr Glu Gln Gln Thr Val Phe Phe Gly Ala
        115                 120                 125

Ile Lys Thr Gly Tyr Thr Ile Gly His Ser Leu Ser Leu Ile Ser Leu
    130                 135                 140

Thr Ala Ala Met Ile Ile Leu Cys Ile Phe Arg Lys Leu His Cys Thr
145                 150                 155                 160

Arg Asn Tyr Ile His Met His Leu Phe Met Ser Phe Ile Met Arg Ala
                165                 170                 175

Ile Ala Val Phe Ile Lys Asp Ile Val Leu Phe Glu Ser Gly Glu Ser
            180                 185                 190

Asp His Cys His Val Gly Ser Val Gly Cys Lys Ala Ala Met Val Phe
        195                 200                 205

Phe Gln Tyr Cys Ile Met Ala Asn Phe Phe Trp Leu Leu Val Glu Gly
```

-continued

```
            210                 215                 220
Leu Tyr Leu His Asn Leu Leu Val Ile Ser Phe Ser Glu Lys Lys
225                 230                 235                 240

Tyr Phe Trp Trp Tyr Ile Leu Ile Gly Trp Gly Ala Pro Ser Val Phe
                245                 250                 255

Ile Thr Ala Trp Ser Leu Ala Arg Val Tyr Phe Glu Asp Thr Gly Cys
                260                 265                 270

Trp Asp Thr Ile Glu Ser His Leu Trp Trp Ile Ile Lys Thr Pro Ile
            275                 280                 285

Leu Val Ser Ile Leu Val Asn Phe Ile Leu Phe Ile Cys Ile Ile Arg
290                 295                 300

Ile Leu Val Gln Lys Leu His Ser Pro Asp Val Gly Arg Asn Glu Asn
305                 310                 315                 320

Ser Gln Tyr Thr Arg Leu Ala Lys Ser Thr Leu Leu Ile Pro Leu
                325                 330                 335

Phe Gly Val His Tyr Ile Met Phe Ala Phe Phe Pro Asp Asn Phe Lys
                340                 345                 350

Val Glu Val Lys Leu Val Phe Glu Leu Ile Leu Gly Ser Phe Gln Gly
                355                 360                 365

Phe Val Val Ala Val Leu Tyr Cys Phe Leu Asn Gly Glu Val Gln Ala
                370                 375                 380

Glu Leu Lys Arg Lys Trp Arg Arg Trp Asn Leu Glu Arg Phe Met Gly
385                 390                 395                 400

Lys Asp Met Lys Tyr His His Pro Ser Leu Gly Ser Asn Gly Thr Asn
                405                 410                 415

Phe Ser Thr Gln Ile Ser Met Leu Thr Lys Cys Ser Pro Lys Thr Arg
                420                 425                 430

Arg Cys Ser Ser Phe Gln Ala Glu Phe Ser Leu Val
            435                 440
```

<210> SEQ ID NO 7
<211> LENGTH: 458
<212> TYPE: PRT
<213> ORGANISM: porcine;

<400> SEQUENCE: 7

```
Met Arg Pro Leu Ser Pro Pro Ala Gly Trp Phe Cys Val Leu Ala
1               5                   10                  15

Gly Val Leu Ala Cys Val Leu Gly Pro Val Gly Ser Trp Ala Val Gly
                20                  25                  30

Leu Gln Gln Glu Glu Cys Asp Tyr Leu Gln Met Ile Lys Val Gln His
                35                  40                  45

Lys Gln Cys Leu Glu Glu Ala Gln Leu Glu Asn Glu Thr Ser Gly Cys
            50                  55                  60

Ser Lys Met Trp Asp Asn Leu Thr Cys Trp Pro Ala Thr Pro Arg Gly
65                  70                  75                  80

Gln Val Val Leu Ala Cys Pro Leu Ile Phe Lys Leu Phe Ser Pro
                85                  90                  95

Thr Gln Gly Leu Asn Val Ser Arg Asn Cys Thr Asp Glu Gly Trp Thr
                100                 105                 110

Pro Leu Glu Pro Gly Pro Tyr Pro Ile Ala Cys Gly Met Asp Asp Lys
            115                 120                 125

Ala Ser Gly Leu Asp Glu Gln Gln Thr Val Phe Tyr Asn Ser Val Lys
130                 135                 140
```

```
Thr Gly Tyr Thr Ile Gly Tyr Ser Leu Ser Leu Ala Leu Leu Val
145                 150                 155                 160

Ala Thr Ala Ile Leu Ser Leu Phe Arg Lys Leu His Cys Thr Arg Asn
            165                 170                 175

Tyr Ile His Met His Leu Phe Ile Ser Phe Ile Leu Arg Ala Thr Ala
                180                 185                 190

Val Phe Ile Lys Asp Leu Ala Leu Phe Asp Ser Glu Glu Ser Asp His
            195                 200                 205

Cys Ser Lys Gly Ser Val Gly Cys Lys Ala Ala Val Leu Phe Gln
210                 215                 220

Tyr Cys Val Met Ala Asn Phe Phe Trp Leu Leu Val Glu Gly Leu Tyr
225                 230                 235                 240

Leu His Thr Leu Leu Ala Val Ser Phe Phe Ser Glu Arg Lys Tyr Phe
                245                 250                 255

Trp Gly Tyr Ile Phe Val Gly Trp Gly Val Pro Ser Thr Phe Ile Met
                260                 265                 270

Val Trp Thr Val Val Arg Ile His Phe Glu Asp Tyr Gly Cys Trp Asp
            275                 280                 285

Thr Ile His Ser Ser Leu Trp Trp Ile Ile Lys Ala Pro Ile Leu Ala
290                 295                 300

Ser Ile Leu Val Asn Phe Ile Leu Phe Ile Arg Ile Ile Gly Ile Leu
305                 310                 315                 320

Val Gln Lys Leu Arg Pro Pro Asp Val Gly Lys Ser Asp Asn Ser Pro
            325                 330                 335

Tyr Ser Arg Leu Ala Lys Ser Thr Leu Leu Leu Ile Pro Leu Phe Gly
            340                 345                 350

Val His Tyr Ile Met Phe Ala Phe Phe Pro Asp Asn Phe Lys Ala Glu
            355                 360                 365

Val Lys Met Val Phe Glu Leu Ile Val Gly Ser Phe Gln Gly Cys Val
            370                 375                 380

Val Ala Ile Leu Tyr Cys Phe Leu Asn Gly Glu Val Gln Ala Glu Leu
385                 390                 395                 400

Arg Arg Lys Trp Arg Arg Trp His Gln Gln Gly Val Leu Gly Trp Asp
                405                 410                 415

Ser Lys Tyr Gln His Pro Ser Gly Gly Ser Asn Gly Asp Thr Cys Ser
            420                 425                 430

Thr Gln Val Ser Met Leu Thr Arg Val Ser Pro Ser Ala Arg Arg Ser
            435                 440                 445

Ser Ser Phe Gln Ala Glu Val Ser Leu Val
    450                 455

<210> SEQ ID NO 8
<211> LENGTH: 459
<212> TYPE: PRT
<213> ORGANISM: rattus sp;

<400> SEQUENCE: 8

Met Arg Pro Pro Ser Pro Pro His Val Arg Trp Leu Cys Val Leu Ala
1               5                   10                  15

Gly Ala Leu Ala Cys Ala Leu Arg Pro Ala Gly Ser Gln Ala Ala Ser
            20                  25                  30

Pro Gln His Glu Cys Glu Tyr Leu Gln Leu Ile Glu Ile Gln Arg Gln
        35                  40                  45

Gln Cys Leu Glu Glu Ala Gln Leu Glu Asn Glu Thr Thr Gly Cys Ser
50                  55                  60
```

```
Lys Met Trp Asp Asn Leu Thr Cys Trp Pro Thr Thr Pro Arg Gly Gln
 65                  70                  75                  80

Ala Val Val Leu Asp Cys Pro Leu Ile Phe Gln Leu Phe Ala Pro Ile
                 85                  90                  95

His Gly Tyr Asn Ile Ser Arg Ser Cys Thr Glu Glu Gly Trp Ser Gln
            100                 105                 110

Leu Glu Pro Gly Pro Tyr His Ile Ala Cys Gly Leu Asn Asp Arg Ala
        115                 120                 125

Ser Ser Leu Asp Glu Gln Gln Thr Lys Phe Tyr Asn Thr Val Lys
130                 135                 140

Thr Gly Tyr Thr Ile Gly Tyr Ser Leu Ser Leu Ala Ser Leu Leu Val
145                 150                 155                 160

Ala Met Ala Ile Leu Ser Leu Phe Arg Lys Leu His Cys Thr Arg Asn
                165                 170                 175

Tyr Ile His Met His Leu Phe Met Ser Phe Ile Leu Arg Ala Thr Ala
            180                 185                 190

Val Phe Ile Lys Asp Met Ala Leu Phe Asn Ser Gly Glu Ile Asp His
        195                 200                 205

Cys Ser Glu Ala Ser Val Gly Cys Lys Ala Ala Val Val Phe Phe Gln
    210                 215                 220

Tyr Cys Val Met Ala Asn Phe Phe Trp Leu Leu Val Glu Gly Leu Tyr
225                 230                 235                 240

Leu Tyr Thr Leu Leu Ala Val Ser Phe Ser Glu Arg Lys Tyr Phe
                245                 250                 255

Trp Gly Tyr Ile Leu Ile Gly Trp Gly Val Pro Ser Val Phe Ile Thr
                260                 265                 270

Ile Trp Thr Val Val Arg Ile Tyr Phe Glu Asp Phe Gly Cys Trp Asp
            275                 280                 285

Thr Ile Ile Asn Ser Ser Leu Trp Trp Ile Ile Lys Ala Pro Ile Leu
        290                 295                 300

Leu Ser Ile Leu Val Asn Phe Val Leu Phe Ile Cys Ile Ile Arg Ile
305                 310                 315                 320

Leu Val Gln Lys Leu Arg Pro Pro Asp Ile Gly Lys Asn Asp Ser Ser
                325                 330                 335

Pro Tyr Ser Arg Leu Ala Lys Ser Thr Leu Leu Leu Ile Pro Leu Phe
            340                 345                 350

Gly Ile His Tyr Val Met Phe Ala Phe Phe Pro Asp Asn Phe Lys Ala
        355                 360                 365

Gln Val Lys Met Val Phe Glu Leu Val Val Gly Ser Phe Gln Gly Phe
    370                 375                 380

Val Val Ala Ile Leu Tyr Cys Phe Leu Asn Gly Glu Val Gln Ala Glu
385                 390                 395                 400

Leu Arg Arg Lys Trp Arg Arg Trp His Leu Gln Gly Val Leu Gly Trp
                405                 410                 415

Ser Ser Lys Ser Gln His Pro Trp Gly Gly Ser Asn Gly Ala Thr Cys
            420                 425                 430

Ser Thr Gln Val Ser Met Leu Thr Arg Val Ser Pro Ser Ala Arg Arg
        435                 440                 445

Ser Ser Ser Phe Gln Ala Glu Val Ser Leu Val
450                 455

<210> SEQ ID NO 9
<211> LENGTH: 447
```

-continued

```
<212> TYPE: PRT
<213> ORGANISM: Carassius auratus;

<400> SEQUENCE: 9

Met Cys Asp Val Val Asn Glu Ile Glu Leu Ala Arg Ala Arg Cys Glu
1               5                   10                  15

Asn Lys Thr Ala Gly Asn Val Thr Ser Gly Cys Lys Gly Met Trp Asp
            20                  25                  30

Ile Ile Ala Cys Trp Pro Ser Ala Lys Val Gly Glu His Val Val Ile
        35                  40                  45

Pro Cys Pro Asn Tyr Phe Arg His Phe Ser Asp His His Glu Gly Asn
    50                  55                  60

Leu Ser Lys Thr Cys Thr Ala Asp Gly Trp Thr Glu Met Asp Pro Met
65                  70                  75                  80

Glu Ile Ala Val Tyr Cys Gly Tyr Asn Leu Asn Gly Thr Val Asp Asp
                85                  90                  95

Asp Ser Phe Phe Arg Ser Val Lys Ile Gly Tyr Thr Ile Gly His Ser
            100                 105                 110

Val Ser Leu Ile Ser Leu Thr Thr Ala Ile Val Ile Leu Cys Met Ser
        115                 120                 125

Arg Lys Leu His Cys Thr Arg Asn Tyr Ile His Met His Leu Phe Val
130                 135                 140

Ser Phe Ile Leu Lys Ala Ile Ala Val Phe Val Lys Asp Ala Val Leu
145                 150                 155                 160

Tyr Asp Val Ile Gln Glu Ser Asp Asn Cys Ser Thr Ala Ser Val Gly
                165                 170                 175

Cys Lys Ala Val Ile Val Phe Phe Gln Tyr Cys Ile Met Ala Ser Phe
            180                 185                 190

Phe Trp Leu Leu Val Glu Gly Leu Tyr Leu His Ala Leu Leu Ala Val
        195                 200                 205

Ser Phe Phe Ser Glu Arg Lys Tyr Phe Trp Trp Tyr Ile Leu Ile Gly
210                 215                 220

Trp Gly Gly Pro Thr Ile Phe Ile Met Ala Trp Ser Phe Ala Lys Ala
225                 230                 235                 240

Tyr Phe Asn Asp Val Gly Cys Trp Asp Ile Ile Glu Asn Ser Asp Leu
                245                 250                 255

Phe Trp Trp Ile Ile Lys Thr Pro Ile Leu Ala Ser Ile Leu Met Asn
            260                 265                 270

Phe Ile Leu Phe Ile Cys Ile Ile Arg Ile Leu Arg Gln Lys Ile Asn
        275                 280                 285

Cys Pro Asp Ile Gly Arg Asn Glu Ser Asn Gln Tyr Ser Arg Leu Ala
290                 295                 300

Lys Ser Thr Leu Leu Leu Ile Pro Leu Phe Gly Ile Asn Phe Ile Ile
305                 310                 315                 320

Phe Ala Phe Ile Pro Glu Asn Ile Lys Thr Glu Leu Arg Leu Val Phe
                325                 330                 335

Asp Leu Ile Leu Gly Ser Phe Gln Gly Phe Val Val Ala Val Leu Tyr
            340                 345                 350

Cys Phe Leu Asn Gly Glu Val Gln Ala Glu Ile Lys Arg Lys Trp Arg
        355                 360                 365

Arg Trp His Leu Glu Arg Phe Leu Gly Pro Asp Thr Lys Tyr Gln His
370                 375                 380

Pro Ser Met Gly Ser Asn Gly Asn Asn Phe Ser Thr Gln Ile Ser Met
385                 390                 395                 400
```

```
Leu Thr Arg Cys Ser Pro Lys Thr Arg Arg Ala Ser Thr Cys Gln Asp
                405                 410                 415

Glu Thr Ser Ile Thr Val Leu Gly Ser Thr Thr Met Gly Tyr Gly His
            420                 425                 430

Gln Asn Glu Thr Val Lys Gly His Glu Asp Val Arg Glu Val Ser
        435                 440                 445

<210> SEQ ID NO 10
<211> LENGTH: 438
<212> TYPE: PRT
<213> ORGANISM: homo sapiens;

<400> SEQUENCE: 10

Met Arg Thr Leu Leu Pro Pro Ala Leu Leu Thr Cys Trp Leu Leu Ala
1               5                   10                  15

Pro Val Asn Ser Ile His Pro Glu Cys Arg Phe His Leu Glu Ile Gln
            20                  25                  30

Glu Glu Glu Thr Lys Cys Ala Glu Leu Leu Arg Ser Gln Thr Glu Lys
        35                  40                  45

His Lys Ala Cys Ser Gly Val Trp Asp Asn Ile Thr Cys Trp Arg Pro
    50                  55                  60

Ala Asn Val Gly Glu Thr Val Thr Val Pro Cys Pro Lys Val Phe Ser
65                  70                  75                  80

Asn Phe Tyr Ser Lys Ala Gly Asn Ile Ser Lys Asn Cys Thr Ser Asp
                85                  90                  95

Gly Trp Ser Glu Thr Phe Pro Asp Phe Val Asp Ala Cys Gly Tyr Ser
            100                 105                 110

Asp Pro Glu Asp Glu Ser Lys Ile Thr Phe Tyr Ile Leu Val Lys Ala
        115                 120                 125

Ile Tyr Thr Leu Gly Tyr Ser Val Ser Leu Met Ser Leu Ala Thr Gly
    130                 135                 140

Ser Ile Ile Leu Cys Leu Phe Arg Lys Leu His Cys Thr Arg Asn Tyr
145                 150                 155                 160

Ile His Leu Asn Leu Phe Leu Ser Phe Ile Leu Arg Ala Ile Ser Val
                165                 170                 175

Leu Val Lys Asp Asp Val Leu Tyr Ser Ser Gly Thr Leu His Cys
            180                 185                 190

Pro Asp Gln Pro Ser Ser Trp Val Gly Cys Lys Leu Ser Leu Val Phe
        195                 200                 205

Leu Gln Tyr Cys Ile Met Ala Asn Phe Phe Trp Leu Leu Val Glu Gly
    210                 215                 220

Leu Tyr Leu His Thr Leu Leu Val Ala Met Leu Pro Pro Arg Arg Cys
225                 230                 235                 240

Phe Leu Ala Tyr Leu Leu Ile Gly Trp Gly Leu Pro Thr Val Cys Ile
                245                 250                 255

Gly Ala Trp Thr Ala Ala Arg Leu Tyr Leu Glu Asp Thr Gly Cys Trp
            260                 265                 270

Asp Thr Asn Asp His Ser Val Pro Trp Trp Val Ile Arg Ile Pro Ile
        275                 280                 285

Leu Ile Ser Ile Ile Val Asn Phe Val Leu Phe Ile Ser Ile Ile Arg
    290                 295                 300

Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Leu Ile Pro Leu
```

```
                        325                 330                 335
Phe Gly Val His Tyr Met Val Phe Ala Val Phe Pro Ile Ser Ile Ser
                340                 345                 350
Ser Lys Tyr Gln Ile Leu Phe Glu Leu Cys Leu Gly Ser Phe Gln Gly
            355                 360                 365
Leu Val Val Ala Val Leu Tyr Cys Phe Leu Asn Ser Glu Val Gln Cys
        370                 375                 380
Glu Leu Lys Arg Lys Trp Arg Ser Arg Cys Pro Thr Pro Ser Ala Ser
385                 390                 395                 400
Arg Asp Tyr Arg Val Cys Gly Ser Ser Phe Ser Arg Asn Gly Ser Glu
                405                 410                 415
Gly Ala Leu Gln Phe His Arg Gly Ser Arg Ala Gln Ser Phe Leu Gln
                420                 425                 430
Thr Glu Thr Ser Val Ile
            435

<210> SEQ ID NO 11
<211> LENGTH: 438
<212> TYPE: PRT
<213> ORGANISM: homo sapiens;

<400> SEQUENCE: 11

Met Arg Thr Leu Leu Pro Pro Ala Leu Leu Thr Cys Trp Leu Leu Ala
1               5                   10                  15
Pro Val Asn Ser Ile His Pro Glu Cys Arg Phe His Leu Glu Ile Gln
                20                  25                  30
Glu Glu Glu Thr Lys Cys Thr Glu Leu Leu Arg Ser Gln Thr Glu Lys
            35                  40                  45
His Lys Ala Cys Ser Gly Val Trp Asp Asn Ile Thr Cys Trp Arg Pro
        50                  55                  60
Ala Asn Val Gly Glu Thr Val Thr Val Pro Cys Pro Lys Val Phe Ser
65                  70                  75                  80
Asn Phe Tyr Ser Lys Ala Gly Asn Ile Ser Lys Asn Cys Thr Ser Asp
                85                  90                  95
Gly Trp Ser Glu Thr Phe Pro Asp Phe Val Asp Ala Cys Gly Tyr Ser
                100                 105                 110
Asp Pro Glu Asp Glu Ser Lys Ile Thr Phe Tyr Ile Leu Val Lys Ala
            115                 120                 125
Ile Tyr Thr Leu Gly Tyr Ser Val Ser Leu Met Ser Leu Ala Thr Gly
        130                 135                 140
Ser Ile Ile Leu Cys Leu Phe Arg Lys Leu His Cys Thr Arg Asn Tyr
145                 150                 155                 160
Ile His Leu Asn Leu Phe Leu Ser Phe Ile Leu Arg Ala Ile Ser Val
                165                 170                 175
Leu Val Lys Asp Asp Val Leu Tyr Ser Ser Gly Thr Leu His Cys
                180                 185                 190
Pro Asp Gln Pro Ser Ser Trp Val Gly Cys Lys Leu Ser Leu Val Phe
            195                 200                 205
Leu Gln Tyr Cys Ile Met Ala Asn Phe Phe Trp Leu Leu Val Glu Gly
        210                 215                 220
Leu Tyr Leu His Thr Leu Leu Val Ala Met Leu Pro Pro Arg Arg Cys
225                 230                 235                 240
Phe Leu Ala Tyr Leu Leu Ile Gly Trp Gly Leu Pro Thr Val Cys Ile
                245                 250                 255
```

```
Gly Ala Trp Thr Ala Ala Arg Leu Tyr Leu Glu Asp Thr Gly Cys Trp
            260                 265                 270

Asp Thr Asn Asp His Ser Val Pro Trp Trp Val Ile Arg Ile Pro Ile
            275                 280                 285

Leu Ile Ser Ile Ile Val Asn Phe Val Leu Phe Ile Ser Ile Ile Arg
            290                 295                 300

Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Leu Ile Pro Leu
            325                 330                 335

Phe Gly Val His Tyr Met Val Phe Ala Val Phe Pro Ile Ser Ile Ser
            340                 345                 350

Ser Lys Tyr Gln Ile Leu Phe Glu Leu Cys Leu Gly Ser Phe Gln Gly
            355                 360                 365

Leu Val Val Ala Val Leu Tyr Cys Phe Leu Asn Ser Glu Val Gln Cys
            370                 375                 380

Glu Leu Lys Arg Lys Trp Arg Ser Arg Cys Pro Thr Pro Ser Ala Ser
385                 390                 395                 400

Arg Asp Tyr Arg Val Cys Gly Ser Ser Phe Ser His Asn Gly Ser Glu
            405                 410                 415

Gly Ala Leu Gln Phe His Arg Ala Ser Arg Ala Gln Ser Phe Leu Gln
            420                 425                 430

Thr Glu Thr Ser Val Ile
            435

<210> SEQ ID NO 12
<211> LENGTH: 438
<212> TYPE: PRT
<213> ORGANISM: homo sapiens

<400> SEQUENCE: 12

Met Arg Thr Leu Leu Pro Pro Ala Leu Leu Thr Cys Trp Leu Leu Ala
1               5                   10                  15

Pro Val Asn Ser Ile His Pro Glu Cys Arg Phe His Leu Glu Ile Gln
            20                  25                  30

Glu Glu Glu Thr Lys Cys Ala Glu Leu Leu Arg Ser Gln Thr Glu Lys
            35                  40                  45

His Lys Ala Cys Ser Gly Val Trp Asp Asn Ile Thr Cys Trp Arg Pro
    50                  55                  60

Ala Asn Val Gly Glu Thr Val Thr Val Pro Cys Pro Lys Val Phe Ser
65                  70                  75                  80

Asn Phe Tyr Ser Lys Ala Gly Asn Ile Ser Lys Asn Cys Thr Ser Asp
            85                  90                  95

Gly Trp Ser Glu Thr Phe Pro Asp Phe Val Asp Ala Cys Gly Tyr Ser
            100                 105                 110

Asp Pro Glu Asp Glu Ser Lys Ile Thr Phe Tyr Ile Leu Val Lys Ala
            115                 120                 125

Ile Tyr Thr Leu Gly Tyr Ser Val Ser Leu Met Ser Leu Ala Thr Gly
            130                 135                 140

Ser Ile Ile Leu Cys Leu Phe Arg Lys Leu His Cys Thr Arg Asn Tyr
145                 150                 155                 160

Ile His Leu Asn Leu Phe Leu Ser Phe Ile Leu Arg Ala Ile Ser Val
            165                 170                 175

Leu Val Lys Asp Asp Val Leu Tyr Ser Ser Ser Gly Thr Leu His Cys
            180                 185                 190
```

```
Pro Asp Gln Pro Ser Ser Trp Val Gly Cys Lys Leu Ser Leu Val Phe
        195                 200                 205

Leu Gln Tyr Cys Ile Met Ala Asn Phe Phe Trp Leu Leu Val Glu Gly
        210                 215                 220

Leu Tyr Leu His Thr Leu Leu Val Ala Met Leu Pro Pro Arg Arg Cys
225                 230                 235                 240

Phe Leu Ala Tyr Leu Leu Ile Gly Trp Gly Leu Pro Thr Val Cys Ile
            245                 250                 255

Gly Ala Trp Thr Ala Ala Arg Leu Tyr Leu Glu Asp Thr Gly Cys Trp
        260                 265                 270

Asp Thr Asn Asp His Ser Val Pro Trp Trp Val Ile Arg Ile Pro Ile
        275                 280                 285

Leu Ile Ser Ile Ile Val Asn Phe Val Leu Phe Ile Ser Ile Arg
290                 295                 300

Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Ile Pro Leu
            325                 330                 335

Phe Gly Val His Tyr Met Val Phe Ala Val Phe Pro Ile Ser Ile Ser
            340                 345                 350

Ser Lys Tyr Gln Ile Leu Phe Glu Leu Cys Leu Gly Ser Phe Gln Gly
        355                 360                 365

Leu Val Val Ala Val Leu Tyr Cys Phe Leu Asn Ser Glu Val Gln Cys
        370                 375                 380

Glu Leu Lys Arg Lys Trp Arg Ser Arg Cys Pro Thr Pro Ser Ala Ser
385                 390                 395                 400

Arg Asp Tyr Arg Val Cys Gly Ser Ser Phe Ser His Asn Gly Ser Glu
            405                 410                 415

Gly Ala Leu Gln Phe His Arg Ala Ser Arg Ala Gln Ser Phe Leu Gln
            420                 425                 430

Thr Glu Thr Ser Val Ile
            435

<210> SEQ ID NO 13
<211> LENGTH: 437
<212> TYPE: PRT
<213> ORGANISM: mus musculus;

<400> SEQUENCE: 13

Met Arg Ala Ser Val Val Leu Thr Cys Tyr Cys Trp Leu Leu Val Arg
1               5                   10                  15

Val Ser Ser Ile His Pro Glu Cys Arg Phe His Leu Glu Ile Gln Glu
            20                  25                  30

Glu Glu Thr Lys Cys Ala Glu Leu Leu Ser Ser Gln Thr Glu Asn Gln
        35                  40                  45

Arg Ala Cys Ser Gly Val Trp Asp Asn Ile Thr Cys Trp Arg Pro Ala
    50                  55                  60

Asp Val Gly Glu Thr Val Thr Val Pro Cys Pro Lys Val Phe Ser Asn
65                  70                  75                  80

Phe Tyr Ser Arg Pro Gly Asn Ile Ser Lys Asn Cys Thr Ser Asp Gly
            85                  90                  95

Trp Ser Glu Thr Phe Pro Asp Phe Ile Asp Ala Cys Gly Tyr Asn Asp
            100                 105                 110

Pro Glu Asp Glu Ser Lys Ile Ser Phe Tyr Ile Leu Val Lys Ala Ile
```

-continued

```
                115                 120                 125
Tyr Thr Leu Gly Tyr Ser Val Ser Leu Met Ser Leu Thr Gly Ser
        130                 135                 140

Ile Ile Ile Cys Leu Phe Arg Lys Leu His Cys Thr Arg Asn Tyr Ile
145                 150                 155                 160

His Leu Asn Leu Phe Leu Ser Phe Met Leu Arg Ala Ile Ser Val Leu
                165                 170                 175

Val Lys Asp Ser Val Leu Tyr Ser Ser Gly Leu Leu Arg Cys His
        180                 185                 190

Asp Gln Pro Ala Ser Trp Val Gly Cys Lys Leu Ser Leu Val Phe Phe
                195                 200                 205

Gln Tyr Cys Ile Met Ala Asn Phe Tyr Trp Leu Leu Val Glu Gly Leu
        210                 215                 220

Tyr Leu His Thr Leu Leu Val Ala Ile Leu Pro Pro Ser Arg Cys Phe
225                 230                 235                 240

Leu Ala Tyr Leu Leu Ile Gly Trp Gly Ile Pro Ser Val Cys Ile Gly
                245                 250                 255

Ala Trp Thr Ala Thr Arg Leu Ser Leu Glu Asp Thr Gly Cys Trp Asp
        260                 265                 270

Thr Asn Asp His Ser Ile Pro Trp Trp Val Ile Arg Met Pro Ile Leu
        275                 280                 285

Ile Ser Ile Val Val Asn Phe Ala Leu Phe Ile Ser Ile Val Arg Ile
290                 295                 300

Leu Leu Gln Lys Leu Thr Ser Pro Asp Val Gly Gly Asn Asp Gln Ser
305                 310                 315                 320

Gln Tyr Lys Arg Leu Ala Lys Ser Thr Leu Leu Leu Ile Pro Leu Phe
                325                 330                 335

Gly Val His Tyr Met Val Phe Ala Ala Phe Pro Ile Gly Ile Ser Ser
                340                 345                 350

Thr Tyr Gln Ile Leu Phe Glu Leu Cys Val Gly Ser Phe Gln Gly Leu
        355                 360                 365

Val Val Ala Val Leu Tyr Cys Phe Leu Asn Ser Glu Val Gln Cys Glu
        370                 375                 380

Leu Lys Arg Arg Trp Arg Gly Leu Cys Leu Thr Gln Ala Gly Ser Arg
385                 390                 395                 400

Asp Tyr Arg Leu His Ser Trp Ser Met Ser Arg Asn Gly Ser Glu Ser
                405                 410                 415

Ala Leu Gln Ile His Arg Gly Ser Arg Thr Gln Ser Phe Leu Gln Ser
        420                 425                 430

Glu Thr Ser Val Ile
        435

<210> SEQ ID NO 14
<211> LENGTH: 437
<212> TYPE: PRT
<213> ORGANISM: rattus norvegicus;

<400> SEQUENCE: 14

Met Arg Ala Ser Val Val Leu Thr Cys Tyr Cys Trp Leu Leu Val Arg
1               5                   10                  15

Val Ser Ser Ile His Pro Glu Cys Arg Phe His Leu Glu Ile Gln Glu
                20                  25                  30

Glu Glu Thr Lys Cys Ala Glu Leu Leu Ser Ser Gln Met Glu Asn His
        35                  40                  45
```

```
Arg Ala Cys Ser Gly Val Trp Asp Asn Ile Thr Cys Trp Arg Pro Ala
    50                  55                  60

Asp Ile Gly Glu Thr Val Thr Val Pro Cys Pro Lys Val Phe Ser Asn
65                  70                  75                  80

Phe Tyr Ser Arg Pro Gly Asn Ile Ser Lys Asn Cys Thr Ser Asp Gly
                85                  90                  95

Trp Ser Glu Thr Phe Pro Asp Phe Ile Asp Ala Cys Gly Tyr Asn Asp
            100                 105                 110

Pro Glu Asp Glu Ser Lys Ile Thr Phe Tyr Ile Leu Val Lys Ala Ile
        115                 120                 125

Tyr Thr Leu Gly Tyr Ser Val Ser Leu Met Ser Leu Thr Thr Gly Ser
    130                 135                 140

Ile Ile Ile Cys Leu Phe Arg Lys Leu His Cys Thr Arg Asn Tyr Ile
145                 150                 155                 160

His Leu Asn Leu Phe Leu Ser Phe Met Leu Arg Ala Ile Ser Val Leu
                165                 170                 175

Val Lys Asp Ser Val Leu Tyr Ser Ser Ser Gly Thr Leu Arg Cys His
            180                 185                 190

Asp Gln Pro Gly Ser Trp Val Gly Cys Lys Leu Ser Leu Val Phe Phe
        195                 200                 205

Gln Tyr Cys Ile Met Ala Asn Phe Tyr Trp Leu Leu Val Glu Gly Leu
    210                 215                 220

Tyr Leu His Thr Leu Leu Val Ala Ile Leu Pro Pro Ser Arg Cys Phe
225                 230                 235                 240

Leu Ala Tyr Leu Leu Ile Gly Trp Gly Ile Pro Ser Val Cys Ile Gly
                245                 250                 255

Ala Trp Ile Ala Thr Arg Leu Ser Leu Glu Asp Thr Gly Cys Trp Asp
            260                 265                 270

Thr Asn Asp His Ser Ile Pro Trp Trp Val Ile Arg Met Pro Ile Leu
        275                 280                 285

Ile Ser Ile Val Val Asn Phe Ala Leu Phe Ile Ser Ile Val Arg Ile
    290                 295                 300

Leu Leu Gln Lys Leu Thr Ser Pro Asp Val Gly Gly Asn Asp Gln Ser
305                 310                 315                 320

Gln Tyr Lys Arg Leu Ala Lys Ser Thr Leu Leu Leu Ile Pro Leu Phe
                325                 330                 335

Gly Val His Tyr Met Val Phe Ala Ala Phe Pro Ile Gly Ile Ser Ser
            340                 345                 350

Thr Tyr Gln Ile Leu Phe Glu Leu Cys Val Gly Ser Phe Gln Gly Leu
        355                 360                 365

Val Val Ala Val Leu Tyr Cys Phe Leu Asn Ser Glu Val Gln Cys Glu
    370                 375                 380

Leu Lys Arg Arg Trp Arg Gly Leu Cys Leu Thr Gln Pro Gly Ser Arg
385                 390                 395                 400

Asp Tyr Arg Leu His Ser Trp Ser Met Ser Arg Asn Gly Ser Glu Ser
                405                 410                 415

Ala Leu Gln Ile His Arg Gly Ser Arg Thr Gln Ser Phe Leu Gln Ser
            420                 425                 430

Glu Thr Ser Val Ile
        435

<210> SEQ ID NO 15
<211> LENGTH: 437
<212> TYPE: PRT
```

-continued

```
<213> ORGANISM: rattus norvegicus;

<400> SEQUENCE: 15

Met Arg Ala Ser Val Val Leu Thr Cys Tyr Cys Trp Leu Leu Val Arg
1               5                   10                  15

Val Ser Ser Ile His Pro Glu Cys Arg Phe His Leu Glu Ile Gln Glu
            20                  25                  30

Glu Glu Thr Lys Cys Ala Glu Leu Leu Ser Ser Gln Met Glu Asn His
        35                  40                  45

Arg Ala Cys Ser Gly Val Trp Asp Asn Ile Thr Cys Trp Arg Pro Ala
    50                  55                  60

Asp Ile Gly Glu Thr Val Thr Val Pro Cys Pro Lys Val Phe Ser Asn
65                  70                  75                  80

Phe Tyr Ser Arg Pro Gly Asn Ile Ser Lys Asn Cys Thr Ser Asp Gly
                85                  90                  95

Trp Ser Glu Thr Phe Pro Asp Phe Ile Asp Ala Cys Gly Tyr Asn Asp
            100                 105                 110

Pro Glu Asp Glu Ser Lys Ile Thr Phe Tyr Ile Leu Val Lys Ala Ile
        115                 120                 125

Tyr Thr Leu Gly Tyr Ser Val Ser Leu Met Ser Leu Thr Thr Gly Ser
130                 135                 140

Ile Ile Ile Cys Leu Phe Arg Lys Leu His Cys Thr Arg Asn Tyr Ile
145                 150                 155                 160

His Leu Asn Leu Phe Leu Ser Phe Met Leu Arg Ala Ile Ser Val Leu
                165                 170                 175

Val Lys Asp Ser Val Leu Tyr Ser Ser Ser Gly Thr Leu Arg Cys His
            180                 185                 190

Asp Gln Pro Gly Ser Trp Val Gly Cys Lys Leu Ser Leu Val Phe Phe
        195                 200                 205

Gln Tyr Cys Ile Met Ala Asn Phe Tyr Trp Leu Leu Val Glu Gly Leu
    210                 215                 220

Tyr Leu His Thr Leu Leu Val Ala Ile Leu Pro Pro Ser Arg Cys Phe
225                 230                 235                 240

Leu Ala Tyr Leu Leu Ile Gly Trp Gly Ile Pro Ser Val Cys Ile Gly
                245                 250                 255

Ala Trp Ile Ala Thr Arg Leu Ser Leu Glu Asp Thr Gly Cys Trp Asp
            260                 265                 270

Thr Asn Asp His Ser Ile Pro Trp Trp Val Ile Arg Met Pro Ile Leu
        275                 280                 285

Ile Ser Ile Val Val Asn Phe Ala Leu Phe Ile Ser Ile Val Arg Ile
    290                 295                 300

Leu Leu Gln Lys Leu Thr Ser Pro Asp Val Gly Gly Asn Asp Gln Ser
305                 310                 315                 320

Gln Tyr Lys Arg Leu Ala Lys Ser Thr Leu Leu Ile Pro Leu Phe
                325                 330                 335

Gly Val His Tyr Met Val Phe Ala Ala Phe Pro Ile Gly Ile Ser Ser
            340                 345                 350

Thr Tyr Gln Ile Leu Phe Glu Leu Cys Val Gly Ser Phe Gln Gly Leu
        355                 360                 365

Val Val Ala Val Leu Tyr Cys Phe Leu Asn Ser Glu Val Gln Arg Glu
370                 375                 380

Leu Lys Arg Arg Trp Arg Gly Leu Cys Leu Thr Gln Pro Gly Ser Arg
385                 390                 395                 400
```

-continued

```
Asp Tyr Arg Leu His Ser Trp Ser Met Ser Arg Asn Gly Ser Glu Ser
            405                 410                 415

Ala Leu Gln Ile His Arg Gly Ser Arg Thr Gln Ser Phe Leu Gln Ser
            420                 425                 430

Glu Thr Ser Val Ile
            435

<210> SEQ ID NO 16
<211> LENGTH: 437
<212> TYPE: PRT
<213> ORGANISM: rat;

<400> SEQUENCE: 16

Met Arg Ala Ser Val Val Leu Thr Cys Tyr Cys Trp Leu Leu Val Arg
1               5                   10                  15

Val Ser Ser Ile His Pro Glu Cys Arg Phe His Leu Glu Ile Gln Glu
            20                  25                  30

Glu Glu Thr Lys Cys Ala Glu Leu Leu Ser Ser Gln Met Glu Asn His
            35                  40                  45

Arg Ala Cys Ser Gly Val Trp Asp Asn Ile Thr Cys Trp Arg Pro Ala
    50                  55                  60

Asp Ile Gly Glu Thr Val Thr Val Pro Cys Pro Lys Val Phe Ser Asn
65                  70                  75                  80

Phe Tyr Ser Arg Pro Gly Asn Ile Ser Lys Asn Cys Thr Ser Asp Gly
                85                  90                  95

Trp Ser Glu Thr Phe Pro Asp Phe Ile Asp Ala Cys Gly Tyr Asn Asp
            100                 105                 110

Pro Glu Asp Glu Ser Lys Ile Thr Phe Tyr Ile Leu Val Lys Ala Ile
            115                 120                 125

Tyr Thr Leu Gly Tyr Ser Val Ser Leu Met Ser Leu Thr Thr Gly Ser
130                 135                 140

Ile Ile Ile Cys Leu Phe Arg Lys Leu His Cys Thr Arg Asn Tyr Ile
145                 150                 155                 160

His Leu Asn Leu Phe Leu Ser Phe Met Leu Arg Ala Ile Ser Val Leu
                165                 170                 175

Val Lys Asp Ser Val Leu Tyr Ser Ser Ser Gly Thr Leu Arg Cys His
            180                 185                 190

Asp Gln Pro Gly Ser Trp Val Gly Cys Lys Leu Ser Leu Val Phe Phe
            195                 200                 205

Gln Tyr Cys Ile Met Ala Asn Phe Tyr Trp Leu Leu Val Glu Gly Leu
    210                 215                 220

Tyr Leu His Thr Leu Leu Val Ala Ile Leu Pro Pro Ser Arg Cys Phe
225                 230                 235                 240

Leu Ala Tyr Leu Leu Ile Gly Trp Gly Ile Pro Ser Val Cys Ile Gly
                245                 250                 255

Ala Trp Ile Ala Thr Arg Leu Ser Leu Glu Asp Thr Gly Cys Trp Asp
            260                 265                 270

Thr Asn Asp His Ser Ile Pro Trp Trp Val Ile Arg Met Pro Ile Leu
            275                 280                 285

Ile Ser Ile Val Val Asn Phe Ala Leu Phe Ile Ser Ile Val Arg Ile
    290                 295                 300

Leu Leu Gln Lys Leu Thr Ser Pro Asp Val Gly Gly Asn Asp Gln Ser
305                 310                 315                 320

Gln Tyr Lys Arg Leu Ala Lys Ser Thr Leu Leu Leu Ile Pro Leu Phe
                325                 330                 335
```

-continued

```
Gly Val His Tyr Met Val Phe Ala Ala Phe Pro Ile Gly Ile Ser Ser
            340                 345                 350

Thr Tyr Gln Ile Leu Phe Glu Leu Cys Val Gly Ser Phe Gln Gly Leu
            355                 360                 365

Val Val Ala Val Leu Tyr Cys Phe Leu Asn Ser Glu Val Gln Cys Glu
            370                 375                 380

Leu Lys Arg Arg Trp Arg Gly Leu Cys Leu Thr Gln Pro Gly Ser Arg
385                         390                 395                 400

Asp Tyr Arg Leu His Ser Trp Ser Met Ser Arg Asn Gly Ser Glu Ser
                405                 410                 415

Ala Leu Gln Ile His Arg Gly Ser Arg Thr Gln Ser Phe Leu Gln Ser
            420                 425                 430

Glu Thr Ser Val Ile
            435
```